（12）United States Patent
Andersen et al.

(10) Patent No.: US 9,173,939 B2
(45) Date of Patent: Nov. 3, 2015

(54) ESTER DERIVATIVES OF ANDROGEN RECEPTOR MODULATORS AND METHODS FOR THEIR USE

(71) Applicants: The University of British Columbia, Vancouver (CA); British Columbia Cancer Agency Branch, Vancouver (CA)

(72) Inventors: Raymond J. Andersen, Vancouver (CA); Marianne D. Sadar, Vancouver (CA); Javier Garcia Fernandez, Gijon (CA); Nasrin R. Mawji, Burnaby (CA); Jun Wang, New Westminster (CA); Carmen Adriana Banuelos, Vancouver (CA)

(73) Assignees: The University of British Columbia, Vancouver, BC (CA); British Columbia Cancer Agency Branch, Vancouver, BC (CA)

( * ) Notice: Subject to any disclaimer, the term of this patent is extended or adjusted under 35 U.S.C. 154(b) by 0 days.

(21) Appl. No.: 14/274,528

(22) Filed: May 9, 2014

(65) Prior Publication Data

US 2014/0335080 A1   Nov. 13, 2014

Related U.S. Application Data

(60) Provisional application No. 61/822,186, filed on May 10, 2013.

(51) Int. Cl.
*A61K 31/075*   (2006.01)
*C07C 43/164*   (2006.01)
(Continued)

(52) U.S. Cl.
CPC ............... *A61K 45/06* (2013.01); *A61K 31/222* (2013.01); *C07C 69/63* (2013.01)

(58) Field of Classification Search
CPC ........................... C07C 43/2055; A61K 31/09
USPC .................................. 568/610, 663; 514/718
See application file for complete search history.

(56) References Cited

U.S. PATENT DOCUMENTS 2,571,217 A   10/1951   Davis et al.
4,284,574 A   8/1981   Bagga
(Continued)

FOREIGN PATENT DOCUMENTS

CA   2 339 775 A1   3/2000
CA   2 606 262 A1   11/2006
(Continued)

OTHER PUBLICATIONS

English Translation of description of JP-09176240-A, 1997.*
(Continued)

*Primary Examiner* — Kamal Saeed
*Assistant Examiner* — Janet L Coppins
(74) *Attorney, Agent, or Firm* — Cooley LLP

(57) ABSTRACT

Compounds having a structure of Structure I:

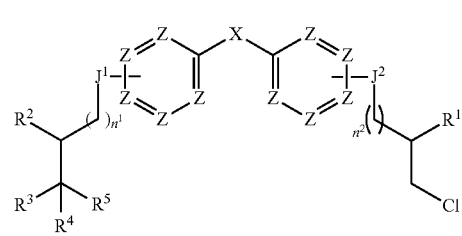

or a pharmaceutically acceptable salt, tautomer, or stereoisomer thereof, wherein $R^1$, $R^2$, $R^3$, $R^4$, $R^5$, $J^1$, $J^2$, X, Z, $n^1$ and $n^2$ are as defined herein, and wherein at least one of $R^1$, $R^2$ or $R^3$ is an alkyl, alkenyl, aryl or aralkyl ester, are provided. Uses of such compounds for treatment of various indications, including prostate cancer, as well as methods of treatment involving such compounds are also provided.

29 Claims, 36 Drawing Sheets

(51) Int. Cl.
*A61K 45/06* (2006.01)
*A61K 31/222* (2006.01)
*C07C 69/63* (2006.01)

(56) References Cited

U.S. PATENT DOCUMENTS

| | | | |
|---|---|---|---|
| 4,369,298 | A | 1/1983 | Kida et al. |
| 4,855,184 | A | 8/1989 | Klun et al. |
| 4,904,760 | A | 2/1990 | Gaku et al. |
| 5,043,375 | A | 8/1991 | Henning et al. |
| 5,155,196 | A | 10/1992 | Kolb et al. |
| 5,362,615 | A | 11/1994 | Hagemann et al. |
| 5,403,697 | A | 4/1995 | Doessel et al. |
| 5,753,730 | A | 5/1998 | Nagata et al. |
| 5,998,674 | A | 12/1999 | Taketani et al. |
| 6,218,430 | B1 | 4/2001 | Allegretto et al. |
| 7,183,323 | B2 | 2/2007 | Chinn et al. |
| 7,674,795 | B2 | 3/2010 | Mailliet et al. |
| 8,686,050 | B2 | 4/2014 | Sadar et al. |
| 2003/0105268 | A1 | 6/2003 | Boriack et al. |
| 2004/0049004 | A1 | 3/2004 | Boriak et al. |
| 2004/0243316 | A1 | 12/2004 | Weinmann et al. |
| 2008/0153837 | A1 | 6/2008 | Mailliet et al. |
| 2008/0193380 | A1 | 8/2008 | Dalton et al. |
| 2008/0255395 | A1 | 10/2008 | Dai et al. |
| 2011/0230556 | A1 | 9/2011 | Sadar et al. |
| 2013/0045204 | A1 | 2/2013 | Andersen et al. |
| 2013/0109758 | A1 | 5/2013 | Sadar et al. |
| 2013/0131167 | A1 | 5/2013 | Sadar et al. |
| 2013/0245129 | A1 | 9/2013 | Sadar et al. |
| 2013/0336962 | A1 | 12/2013 | Andersen et al. |
| 2014/0248263 | A1 | 9/2014 | Andersen et al. |
| 2015/0010469 | A1 | 1/2015 | Andersen et al. |

FOREIGN PATENT DOCUMENTS

| | | | | |
|---|---|---|---|---|
| EP | 0056175 | A1 | 7/1982 | |
| EP | 0 293 768 | A1 | 12/1988 | |
| EP | 0515128 | A1 | 11/1992 | |
| JP | B-S45-008432 | | 3/1970 | |
| JP | H01-503541 | | 11/1989 | |
| JP | H02-4815 | | 1/1990 | |
| JP | 6-049473 | A2 | 4/1994 | |
| JP | 09176240 | A * | 9/1997 | ............ C08F 20/22 |
| JP | 11-166087 | A2 | 6/1999 | |
| JP | A-H10-316803 | | 12/1999 | |
| JP | 2000-072705 | A2 | 3/2000 | |
| JP | 2006-208607 | A | 8/2006 | |
| JP | 2006-265351 | A2 | 10/2006 | |
| JP | 2007-290980 | | 11/2007 | |
| PL | 135932 | | 9/1984 | |
| WO | WO 88/09782 | A1 | 12/1988 | |
| WO | WO 00/01813 | A2 | 1/2000 | |
| WO | WO 00/10958 | A1 | 3/2000 | |
| WO | WO 01/88013 | A2 | 11/2001 | |
| WO | WO 02/05813 | A2 | 1/2002 | |
| WO | WO 03/004481 | A1 | 1/2003 | |
| WO | WO 2005/077967 | A1 | 8/2005 | |
| WO | WO 2010/000066 | A1 | 1/2010 | |
| WO | WO 2011/082487 | A1 | 7/2011 | |
| WO | WO 2011/082488 | A1 | 7/2011 | |
| WO | WO 2012/139039 | A2 | 10/2012 | |
| WO | WO 2012/145328 | A1 | 10/2012 | |
| WO | WO 2012/145330 | A1 | 10/2012 | |
| WO | WO 2013/028572 | A1 | 2/2013 | |
| WO | WO 2013/028791 | A1 | 2/2013 | |
| WO | WO 2014/179867 | A1 | 11/2014 | |

OTHER PUBLICATIONS

Anderson, R. et al., "Regression of Castrate-Recurrent Prostate Cancer by a Small-Molecule Inhibitor of the Amino-Terminus Domain of the Androgen Receptor", *Cancer Cell*, 17:535-546 (2010).
Anton, R. et al., "Opinion of the scientific panel on food additives, flavourings, processing aids and materials in contact with food (AFC) on a request from the commission related to 2,2-bis(4-hydroxyphenyl)propane bis(2,3-epoxypropyl)ether (bisphenol A diglycidyl ether, BADGE), REF. No. 13510 and 39700 (EFSA-Q-2003178)", *The EFSA Journal*, 86:1-40 (2004).
Auzou et al., *European Journal of Medicinal Chemistry*, 9(5):548-554 (1974) (with English Abstract).
Balbay, M.D. et al., "Highly Metastatic Human Prostate Cancer Growing within the Prostate of Athymic Mice Overexpresses Vascular Endothelial Growth Factor", *Clinical Cancer Research*, 5:783-789 (1999).
Bao, B. et al., "Androgen signaling is required for the vitamin D-mediated growth inhibition in human prostate cancer cells", *Oncogene*, 23:3350-3360 (2004).
Berge, S.M. et al., "Pharmaceutical Salts", *Pharmaceutical Sciences*, 66(1):1-19 (1977).
Berger, U. et al., "Identification of Derivatives of Bisphenol A Diglycidyl Ether and Novolac Glycidyl Ether in Can Coatings by Liquid Chromatography/Ion Trap Mass Spectrometry," Journal of AOAC International, *Food Chemical Contaminants*, 83(6):1367-1376 (2000).
Biles, J.E. et al., "Determination of the Diglycidyl Ether of Bisphenol A and its Derivatives in Canned Foods", *J. Agric. Food Chem.*, 47:1965-1969 (1999).
Bisson, W.H. et al., "Discovery of antiandrogen activity of nonsteroidal scaffolds of marketed drugs", *PNAS*, 104(29):11927-11932 (2007).
Blaszczyk, N. et al., "Osteoblast-Derived factors Induce Androgen-Independent Proliferation and Expression of Prostate-Specific Antigen in Human Prostate Cancer Cells", *Clin. Cancer Res.*, 10:1860-1869 (2004).
Bohler, Paul et al., "Identification of Migrants from Coatings of Food Cans and Tubes: Reaction Products of Bisphenol-A-Diglycidyl Ether (BADGE) with Phenols and Solvents," *Mitt. Gebiete Lebensm. Hyg.*, 89:529-547 (1998).
Bruckheimer, E.M. et al., "Apoptosis in prostate carcinogenesis a growth regulator and a therapeutic target", *Cell Tissue Res*, 301:153-162 (2000).
Chang, C. et al., "Development of Peptide Antagonists for the Androgen Receptor Using Combinatorial Peptide Phage Display," *Molecular Endocrinology*, 19(10): 2478-2490 (2005).
Clinton, G.M. et al., "Estrogen action in human ovarian cancer", *Critical Reviews in Oncology/Hematology*, 25:1-9 (1997).
Culig, Zoran et al., "Androgen Receptor Activation in Prostatic Tumor Cell Lines by Insulin-like Growth Factor-I, Keratinocyte Growth Factor, and Epidermal Growth Factor", *Cancer Research*, 54:5474-5478 (1994).
Danquah, M. et al., "Micellar Delivery of Bicalutamide and Embelin for Treating Prostate Cancer", *Pharmaceutical Research*, 26:2081-2092 (2009).
Das, Debasish et al., "Sulfonic acid functionalized mesoporous MCM-41 silica as a convenient catalyst for Bisphenol-A synthesis", *Chemical Communications*, pp. 2178-2179 (2001).
Dehm, S. et al., "Ligand-independent Androgen Receptor Activity is Activation Function-2-independent and Resistant to Antiandrogens in Androgen Refractory Prostate Cancer Cells", *The Journal of Biological Chemistry*, 281(38):27882-27893 (2006).
Dehm, S. et al., "Splicing of a Novel Androgen Receptor Exon Generates a Constitutively Active Androgen Receptor that Mediates Prostate Cancer Therapy Resistance", *Cancer Research*, 68:5469-5477 (2008).
Edmondson, J.M. et al., "The human ovarian surface epithelium is an androgen responsive tissue", *British Journal of Cancer*, 86:879-885 (2002).
Estebanez-Perpiñá, E. et al., "A surface on the androgen receptor that allosterically regulates coactivator binding", *PNAS*, 104(41):16074-16079 (2007).
Estebanez-Perpiñá, E. et al., "The Molecular Mechanisms of Coactivator Utilization in Ligand-dependent Transactivation by the Androgen Receptor", *The Journal of Biological Chemistry*, 280(9):8060-8068 (2005).

(56) References Cited

OTHER PUBLICATIONS

Fehlberg S. et al., "Bisphenol A diglycidyl ether induces apoptosis in tumor cells independently of peroxisome proliferator-activated receptor-y, in caspase-dependent and -independent manners", *Biochem. J.,* 362:573-578 (2002).

Gallart-Ayala, H. et al., "The analysis of bisphenol A-diglycidyl ether (BADGE), bisphenol F-diglycidyl ether (BFDGE) and their derivatives in canned food and beverages by LC-MS/MS", *Thermo Fisher Scientific Inc.,* 4 pages (2011).

Garuti, L., et al., "Irreversible Protein Kinase Inhibitors", *Current Medicinal Chemistry,* 18:2981-2994 (2011).

Gleave, Martin et al., "Acceleration of Human Prostate Cancer Growth in Vivo by Factors Produced by Prostate and Bone Fibroblasts", *Cancer Research,* 51:3753-3761 (1991).

Gregory, Christopher et al., "Epidermal Growth Factor Increases Coactivation of the Androgen Receptor in Recurrent Prostate Cancer", *The Journal of Biological Chemistry,* 279(8):7119-7130 (2004).

Guinan, P.D. et al., "Impotence Therapy and Cancer of the Prostate", *The American Journal of Surgery,* 131:599-600 (1976).

Guo, Zhiyong et al., "A Novel Androgen Receptor Splice Variant Is Up-regulated during Prostate Cancer Progression and Promotes Androgen Depletion-Resistant Growth", *Cancer Research,* 69:2305-13 (2009).

Haggstrom, Stina et al., "Testosterone Induces Vascular Endothelial Growth Factor Synthesis in the Ventral Prostate in Castrated Rats", *The Journal of Urology,* 161:1620-1625 (1999).

Harper et al., "Expression of Androgen Receptor and Growth Factors in Premalignant Lesions of the Prostate", *Journal of Pathology,* 186:169-177 (1998).

He, B. et al., "Activation Function 2 in the Human Androgen Receptor Ligand Binding Domain Mediates Interdomain Communication with the $NH_2$-terminal Domain", *The Journal of Biological Chemistry,* 274(52):37219-37225 (1999).

He, B. et al., "Structural Basis for Androgen Receptor Interdomain and Coactivator Interactions Suggests a Transition in Nuclear Receptor Activation Function Dominance," Molecular Cell, 16:425-438 (2004).

Heinlein, Cynthia A., et al., "Androgen Receptor in Prostate Cancer", *Endocrine Reviews,* 25(2):276-308 (2004).

Helzlsouer, Kathy J., et al., "Serum Gonadotropins and Steroid Hormones and the Development of Ovarian Cancer", *JAMA,* 274(24):1926-1930 (1995).

Horoszewicz, J.S. et al., "LNCaP Model of Human Prostatic Carcinoma", *Cancer Research,* 43:1809-1818 (1983).

Hu, R. et al., "Ligand-Independent Androgen Receptor Variants Derived from Splicing of Cryptic Exons Signify Hormone-Refractory Prostate Cancer", *Cancer Research,* 69:16-22 (2009).

Huber, P.R. et al., "Prostate Specific Antigen. Experimental and Clinical Observations", *Scand J. Urol. Nephroi.,* 104:33-39 (1987).

Hur, E. et al., "Recognition and Accommodation at the Androgen Receptor Coactivator Binding Interface," PLoS Biology, 2(9):1303-1312 (2004).

Isaacs, J.T., et al., "New Biochemical Methods to Determine Androgen Sensitivity of Prostatic Cancer: The Relative Enzymatic Index (REI)", *Prostate Cancer and Hormone Receptors,* pp. 133-144 (1979).

Isaacs, J.T., "Antagonistic Effect of Androgen on Prostatic Cell Death", *The Prostate,* 5:545-557 (1984).

Jackson, J. A. et al., "Prostatic Complications of Testosterone Replacement Therapy", *Arch. Intern. Med.,* 149:2365-2366 (1989).

Jenster, G. et al., "Domains of the Human Androgen Receptor Involved in Steroid Binding, Transcriptional Activation, and Subcellular Localization", *Molecular Endocrinology,* 5:1396-404 (1991).

Jia, L. et al., "Androgen Receptor Signaling: Mechanism of Interleukin-6 Inhibition", *Cancer Research,* 64:2619-2626 (2004).

Jia, L. et al., "Androgen Receptor-Dependent PSA Expression in Androgen-Independent Prostate Cancer Cells Does Not Involve Androgen Receptor Occupancy of the PSA Locus", *Cancer Research,* 65:8003-8008 (2005).

Kaighn, M.E. et al., "Prostate Carcinoma: Tissue Culture Cell Lines", *National Cancer Institute Monograph* No. 49, pp. 17-21 (1978).

Kemppainen, J. A. et al., "Distinguishing Androgen Receptor Agonists and Antagonists: Distinct Mechanisms of Activation by Medroxyprogesterone Acetate and Dihydrotestosterone", *Mol. Endocrinol.,* 13:440-454 (1999).

Kim, D. et al., "Androgen Receptor Expression and Cellular Proliferation During Transition from Androgen-Dependent to Recurrent Growth after Castration in the CWR22 Prostate Cancer Xenograft", *American Journal of Pathology,* 160(1):219-226 (2002).

Kolbel, M. et al., "Design of Liquid Crystalline Block Molecules with Nonconventional Mesophase Morphologies: Calamitic Bolaamphiphiles with Lateral Alkyl Chains", *J. Am. Chem. Soc.* ,123:6809-6818 (2001).

Kumar, S. et al., "Synthesis of new crown analogs derived from bisphenol," *Indian Journal Chemistry,* 36B:656-661 (1997).

L'Heureux, A. et al., "Aminodifluorosulfinium Salts: Selective Fluorination Reagents with Enhanced Thermal Stability and Ease of Handling", *J. Org. Chem,* 75:3401-3411 (2010).

Langley, E. et al., "Evidence for an Anti-parallel Orientation of the Ligand-activated Human Androgen Receptor Dimer", *The Journal of Biological Chemistry,* 270(50):29983-29990 (1995).

Lannoye, G.S. et al., "N-Fluoroalkylated and N-alkylated analogs of the dopaminergic D-2 receptor antagonist raclopride", *J. Med. Chem.,* 33(9):2430-2437 (1990).

Loren, J.C. et al., "Synthesis of achiral and racemic catenanes based on terpyridine and a directionalized terpyridine mimic, pyridylphenanthroline", *Org. Biomol. Chem.,* 3(17):3105-3116 (2005).

Louie, M.C. et al., "Androgen-induced recruitment of RNA polymerase II to a nuclear receptor-p160 coactivator complex", *PNAS,* 100(5)2226-2230 (2003).

Martin, S.J. et al., "A new precursor for the radiosynthesis of [$^{18}$F]FLT", Nuclear Medicine and Biology, 29:263-273 (2002).

Masiello, D. et al., "Bicalutamide Functions as an Androgen Receptor Antagonist by Assembly of a Transcriptionally Inactive Receptor", *The Journal of Biological Chemistry,* 277(29):26321-26326 (2002).

Melnyk, O. et al., "Neutralizing Ant-Vascular Endothelial Growth Factor Antibody Inhibits Further Growth of Established Prostate Cancer and Metastases in a Pre-Clinical Model", *The Journal of Urology,* 161:960-963 (1999).

Miller, J.I. et al., "The Clinical Usefulness of Serum Prostate Specific Antigen After Hormonal Therapy of Metastatic Prostate Cancer", *The Journal of Urology,* 147:956-961 (1992).

Mitsiades, C.S. et al., "Molecular biology and cellular physiology of refractoriness to androgen ablation therapy in advanced prostate cancer", *Expert Opin. Investig. Drugs,*10(6):1099-1115 (2001).

Myung, J-K et al., "An androgen receptor N-terminal domain antagonist for treating prostate cancer," *The Journal of Clinical Investigation,* 123(7):2948-2960 (2013).

Nakazawa, H. et al., "In vitro assay of hydrolysis and chlorohydroxy derivatives of bisphenol a diglycidyl ether for estrogenic activity", *Food and Chemical Toxicology,* 40:1827-1832 (2002).

Nazareth, L.V. et al, "Activation of the Human Androgen Receptor through a Protein Kinase A Signaling Pathway", *The Journal of Biological Chemistry,* 271(33):19900-19907 (1996).

Noble, R. L., "The development of prostatic adenocarcinoma in Nb Rats following prolonged sex hormone administration", *Cancer Research,* 37:1929-1933 (1977).

Noble, R. L., "Sex steroids as a cause of adenocarcinoma of the dorsal prostate in Nb Rats, and their influence on the growth of transplants", *Oncology,* 34:138-141 (1977).

Ogawa, Y. et al., "Estrogenic activities of chemicals related to food contact plastics and rubbers tested by the yeast two-hybrid assay," *Food Additives and Contaminants,* 23:4, 422-430 (2006).

Poustka, J. et al., "Determination and occurrence of bisphenol A, bisphenol A diglycidyl ether, and bisphenol F diglycidyl ether, including their derivatives, in canned foodstuffs' from the Czech retail market," *Czech J. Food Sci.,* 25(4):221-229 (2006).

Quayle, S. et al., "Androgen receptor decoy molecules block the growth of prostate cancer", *PNAS,* 104(4): 1331-1336 (2007).

Rao, B.R. et al., "Endocrine Factors in Common Epithelial Ovarian Cancer", *Endocrine Reviews,* 12(1):14-26 (1991).

(56) References Cited

OTHER PUBLICATIONS

Reid, J. et al., "Conformational Analysis of the Androgen Receptor Amino-terminal Domain Involved in Transactivation," *The Journal of Biological Chemistry*, 277:20079-20086 (2002).
Risch, H.A., "Hormonal Etiology of Epithelial Ovarian Cancer, With a Hypothesis Concerning the Role of Androgens and Progesterone", *Journal of the National Cancer Institute*, 90(23):1774-1786 (1998).
Roberts, J. T. et al., "Adenocarcinoma of Prostate in 40-Year-Old Body-Builder", *Lancet*, 2:742 (1986).
Rokicki, G. et al., "Reactions of 4-chloromethyl-1,3-dioxolan-2-one with phenols as a new route to polyols and cyclic carbonates", *Journal f. prakt. Chemie.*, 327:718-722 (1985).
Ross, R.K. et al., "Androgen Metabolism and Prostate Cancer: Establishing a Model of Genetic Susceptibility", *European Urology*, 35:355-361 (1999).
Sadar, M., "Androgen-independent Induction of Prostate-specific Antigen Gene Expression via Cross-talk between the Androgen Receptor and Protein Kinase A signal Transduction Pathways," *The Journal of Biological Chemistry*, 274(12):7777-7783 (1999).
Sadar, M. et al., "Prostate cancer: molecular biology of early progression to androgen independence", *Endocrine-Related Cancer*, 6:487-502 (1999).
Sadar, M.D. et al., "Characterization of a New in Vivo Hollow Fiber Model for the Study of Progression of Prostate Cancer to Androgen Independence", *Molecular Cancer Therapeutics*, 1:629-637 (2002).
Sato, N. et al., "Intermittent Androgen Suppression Delays Progression to Androgen-independent Regulation of Prostate-specific Antigen Gene in the LNCaP Prostate Tumour Model", *J. Steroid Biochem. Mol. Biol.*, 58:139-146 (1996).
Sato, N. et al., "A Metastatic and Androgen-sensitive Human Prostate Cancer Model Using Intraprostatic Inoculation of LNCaP Cells in SCID Mice", *Cancer Research*, 57:1584-1589 (1997).
Satoh, K. et al., "Study on Anti-Androgenic Effects of Bisphenol a Diglycidyl Ether (BADGE), Bisphenol F Diglycidyl Ether (BFDGE) and Their Derivatives Using Cells Stably Transfected with Human Androgen Receptor, AR-EcoScreen", *Food and Chemical Toxicology*, 42:983-993 (2004).
Schaefer, A. et al, "Migration from can coatings: Part 3. Synthesis, identification and quantification of migrating epoxy-based substances below 1000 Da", *Food Additives and Contaminants*, 21(4):390-405 (2004).
Snoek, R. et al., "Induction of Cell-free, In Vitro Transcription by Recombinant Androgen Receptor Peptides", *J. Steroid Biochem. Mol. Biol.*, 59:243-250 (1996).
Still, W. C. et al., "Rapid Chromatographic Technique for Preparative Separations with Moderate Resolution", *J. Org. Chem.*, 43(14):2923-2925 (1978).
Sun, S. et al., "Castration resistance in human prostate cancer is conferred by a frequently occurring androgen receptor splice variant", *The Journal of Clinical Investigation*, 120(8):2715-30 (2010).
Tanji, N. et al., "Growth Factors: Rules in Andrology", *Archives of Andrology*, 47:1-7 (2001).
Taplin, M.E. et al., "Selection for Androgen Receptor Mutations in Prostate cancers Treated with Androgen Antagonist", *Cancer Research*, 59:2511-2515 (1999).
Taskeen, A. et al., "Analysis of bisphenol a in canned food: A mini review", *Asian Journal of Chemistry*, 22(5):4133-4135 (2010).
Thomson, A.A., "Role of androgens and fibroblast growth factors in prostatic development", *Reproduction*, 121:187-195 (2001).
Ueda, T. et al., "Activation of the Androgen Receptor N-terminal Domain by Interleukin-6 via MAPK and STAT3 Signal Transduction Pathways," *The Journal of Biological Chemistry*, 277(9):7076-7085 (2002).
Ueda, T. et al., "Ligand-independent Activation of the Androgen Receptor by Interleukin-6 and the Role of Steroid Receptor Coactivator-1 in Prostate cancer Cells," The Journal of Biological Chemistry, 277(41): 38087-38094 (2002).
Uematsu, Y. et al., "Chlorohydrins of bisphenol A diglycidyl ether (BADGE) and bisphenol F diglycidyl ether (BFDGE) in canned foods and ready-to-drink coffees from the Japanese marker", *Food Additives and Contaminants*, 18(2):177-185 (2001).
Van Der Kwast, T.H. et al., "Androgen Receptors in Endocrine-Therapy-Resistant Human Prostate Cancer", *Inter. J. Cancer*, 48:189-193 (1991).
Van Scherpenzeel, M. et al., "Nanomolar affinity, iminosugar-based chemical probes for specific labeling of lysosomal glucocerebrosidase", *Bioorganic & Medicinal Chemistry*, 18:267-273 (2010).
Wang, G. et al., "Identification of genes targeted by the androgen and PKA signaling pathways in prostate cancer cells", *Oncogene*, 25:7311-7323 (2006).
Wang, Q. et al., "Spatial and Temporal Recruitment of Androgen Receptor and Its Coactivators Involves Chromosomal Looping and Polymerase Tracking", *Molecular Cell*, 19:631-642 (2005).
Wetherill, Y. B. et al., "In vitro molecular mechanisms of bisphenol A action," Reproductive Toxicology, 24:178-198 (2007).
Wilding, G., "The Importance of Steroid Hormones in Prostate Cancer", *Cancer Surveys*, 14:113-130 (1992).
Wilson, J.D. et al., "Long-Term Consequences of Castration in Men: Lessons from the Skoptzy and the Eunuchs of the Chinese and Ottoman Courts", *The Journal of Clinical Endocrinology & Metabolism*, 84:4324-4331 (1999).
Wong, C. et al., "Steroid Requirement for Androgen Receptor Dimerization and DNA Binding", *J. Biol. Chem.*, 268(25):19004-19012 (1993).
Xu, X. et al, "Synthesis and Stability Study of Dental Monomers Containing Methacrylamidoethyl Phosphonic Acids", *Journal of Polymer Science: Part A Polymer Chemistry*, 45:99-110 (2007).
Ye, Deyong, An Introduction to Computer-Aided Drug Design, pp. 13-14, Jan. 31, 2004.
Zuhayra, M. et al., "New approach for the synthesis of [$^{18}$F]fluoroethyltyrosine for cancer imaging: Simple, fast, and high yielding automated synthesis", *Bioorganic & Medicinal Chemistry*, 17, 7441-7448 (2009).
Supplementary European Search Report in EP Application No. 09771876.1 dated Jun. 20, 2011, 5 pages.
Supplementary European Search Report in EP Application No. 11731645.5 dated mailed Jun. 20, 2013, 11 pages.
International Preliminary Report on Patentability for PCT/CA2009/000902 issued Jan. 5, 2011, 7 pages.
International Search Report for PCT/CA2009/000902 mailed Sep. 1, 2009, 4 pages.
Written Opinion for PCT/CA2009/000902 mailed Sep. 1, 2009, 6 pages.
International Preliminary Report on Patentability for PCT/US2012/032584 issued Oct. 8, 2013, 6 pages.
International Search Report for PCT/US2012/032584 mailed Jul. 31, 2012, 3 pages.
Written Opinion for PCT/US2012/032584 mailed Jul. 31, 2012, 5 pages.
International Preliminary Report on Patentability for PCT/US2012/033959 dated Oct. 22, 2013, 8 pages.
International Search Report for PCT/US2012/033959 mailed Jul. 18, 2012, 3 pages.
Written Opinion for PCT/US2012/033959 mailed Jul. 18, 2012, 7 pages.
International Preliminary Report on Patentability for PCT/US2012/033957 dated Oct. 22, 2013, 6 pages.
International Search Report for PCT/US2012/033957 mailed Jul. 18, 2012, 3 pages.
Written Opinion for PCT/US2012/033957 mailed Jul. 18, 2012, 5 pages.
International Preliminary Report on Patentability for PCT/CA2011/000019 dated Jul. 10, 2012, 8 pages.
International Search Report for PCT/CA2011/000019 mailed Mar. 21, 2011, 7 pages.
Written Opinion for PCT/CA2011/000019 mailed Mar. 21, 2011, 7 pages.
International Preliminary Report on Patentability for PCT/CA2011/000021 dated Jul. 10, 2012, 8 pages.
International Search Report for PCT/CA2011/000021 mailed Apr. 11, 2011, 8 pages.

(56) References Cited

OTHER PUBLICATIONS

Written Opinion for PCT/CA2011/000021 mailed Apr. 11, 2011, 7 pages.
International Preliminary Report on Patentability for PCT/US2012/051481 dated Feb. 25, 2014, 8 pages.
International Search Report for PCT/US2012/051481 mailed Nov. 26, 2012, 4 pages.
Written Opinion for PCT/US2012/051481 mailed Nov. 26, 2012, 7 pages.
International Preliminary Report on Patentability for PCT/US2012/051923 dated Feb. 25, 2014, 9 pages.
International Search Report for PCT/US2012/051923 mailed Jan. 28, 2013, 4 pages.
Written Opinion for PCT/US2012/051923 mailed Jan. 28, 2013, 8 pages.
Brzozowski, Z. et al., "Precursors for bisphenolic resins", CAPLUS Database Accession No. 1990:36690, Document No. 112:33690, (1987), 1 page (Abstract).
Choi, K. M. et al., "New Families of Photocurable Oligomeric Fluoromonomers for Use in Dental Composites", *Chemistry of Materials*, 8(12):2704-2707 (1996).
Crivello, J. V. et al., "Synthesis and photopolymerization of multifunctional propenyl ether monomers," Database CAPLUS [online], Chemical Abstracts Service, Columbus, Ohio, US, XP002729292, retrieved from STN CA Caesar Accession No. 1994-606067 (1994), 3 pages.
Crivello, J. V. et al., "Synthesis and photopolymerization of multifunctional propenyl ether monomers", *Journal of Macromolecular Science, Pure and Applied Chemistry*, A31(9):1105-1119 (1994).
Cook, W. D., "Fracture and Structure of Highly Crosslinked Polymer Composites", *Journal of Applied Polymer Science*, 42:1259-1269 (1991).
Nedolya, N. A. et al., Zhurnal Organicheskoi Khimii, 30(8):1163-1166 (1994).

Paris, F. et al., "Phenylphenols, biphenols, bisphenol-A and 4-tert-octyphenol exhibit $\alpha$ and $\beta$ estrogen activities and antiandrogen activity in reporter cell lines," *Molecular and Cellular Endocrinology*, 193:43-49 (2002).
Penczek, P. et al., "Synthesis and cyclotrimerization of dipropargyl derivatives of diepoxides," Database CAPLUS [Online] Chemical Abstracts Service, Columbus, Ohio, retrieved from STN CA Caesar Accession No. 1995:741510 (1995), 2 pages.
Penczek, P. et al., "Synthesis and cyclotrimerization of dipropargyl derivatives of diepoxides," *Polimery*, (Warsaw), 40(5):274-2777 (1995).
Petersen, H. et al., "Determination of bisphenol A diglycidyl ether (BADGE) and its derivatives in food: identification and quantification by internal Standard", *Eur. Food Res. Technol.*, 216:355-364 (2003).
Poouthree, K. et al., "Comparison of resolution in microemulsion EKC and MEKC employing suppressed electroosmosis: Application to bisphenol-A-diglycidyl ether and its derivatives", *Electrophoresis*, 28(20):3705-3711 (2007).
Reader, C. E. L., "Epoxy Resin Derivatives for Stoving Systems", *Surface Coatings Australia*, 25(10):6-9 (1988).
Rusu, E. et al.: "Photosensitive compounds with chloromethyl groups", *Revue Roumaine de Chimie*, 45(5):451-456 (2000).
Silverman, R. B., "The Organic Chemistry of Drug Design and Drug Action", Academic Press, Inc., Harcourt Brace Jovanovich, pp. 15-20, 9 pages (1992).
Decision of Refusal for Japanese Application No. 2011-515039, mailed Dec. 2, 2014, 18 pages (English translation).
Extended European Search Report in Application No. EP 12768410.8 dated Sep. 22, 2014, 10 pages.
International Search Report and Written Opinion for PCT/CA2014/000414 mailed Dec. 4, 2014, 6 pages.
International Search Report and Written Opinion for PCT/CA2014/000685 mailed Dec. 4, 2014, 13 pages.

\* cited by examiner

ESTER DERIVATIVES OF ANDROGEN RECEPTOR MODULATORS AND METHODS FOR THEIR USE

CROSS REFERENCE TO RELATED APPLICATIONS

This application claims the benefit of U.S. Provisional Application No. 61/822,186, filed on May 10, 2013, the entire contents of which are hereby incorporated by reference in their entirety for all purposes.

STATEMENT OF GOVERNMENT INTEREST

This disclosure was made in part with government support under Grant No. 2R01 CA105304 awarded by the National Cancer Institute. The United States Government has certain rights in this disclosure.

BACKGROUND

1. Technical Field

This disclosure generally relates to ester derivatives of bisphenol-related compounds and their use for treatment of various indications. In particular the disclosure relates to ester derivatives of bisphenol-related compounds and their use for treatment of various cancers, for example, all stages of prostate cancer, including androgen dependent, androgen-sensitive and castration-resistant prostate cancers.

2. Description of the Art

Androgens mediate their effects through the androgen receptor (AR). Androgens play a role in a wide range of developmental and physiological responses and are involved in male sexual differentiation, maintenance of spermatogenesis, and male gonadotropin regulation (R. K. Ross, G. A. Coetzee, C. L. Pearce, J. K. Reichardt, P. Bretsky, L. N. Kolonel, B. E. Henderson, E. Lander, D. Altshuler & G. Daley, *Eur Urol* 35, 355-361 (1999); A. A. Thomson, *Reproduction* 121, 187-195 (2001); N. Tanji, K. Aoki & M. Yokoyama, *Arch Androl* 47, 1-7 (2001)). Several lines of evidence show that androgens are associated with the development of prostate carcinogenesis. Firstly, androgens induce prostatic carcinogenesis in rodent models (R. L. Noble, *Cancer Res* 37, 1929-1933 (1977); R. L. Noble, *Oncology* 34, 138-141 (1977)) and men receiving androgens in the form of anabolic steroids have a higher incidence of prostate cancer (J. T. Roberts & D. M. Essenhigh, *Lancet* 2, 742 (1986); J. A. Jackson, J. Waxman & A. M. Spiekerman, *Arch Intern Med* 149, 2365-2366 (1989); P. D. Guinan, W. Sadoughi, H. Alsheik, R. J. Ablin, D. Alrenga & I. M. Bush, *Am J Surg* 131, 599-600 (1976)). Secondly, prostate cancer does not develop if humans or dogs are castrated before puberty (J. D. Wilson & C. Roehrborn, *J Clin Endocrinol Metab* 84, 4324-4331 (1999); G. Wilding, *Cancer Surv* 14, 113-130 (1992)). Castration of adult males causes involution of the prostate and apoptosis of prostatic epithelium while eliciting no effect on other male external genitalia (E. M. Bruckheimer & N. Kyprianou, *Cell Tissue Res* 301, 153-162 (2000); J. T. Isaacs, *Prostate* 5, 545-557 (1984)). This dependency on androgens provides the underlying rationale for treating prostate cancer with chemical or surgical castration (androgen ablation).

Androgens also play a role in female cancers. One example is ovarian cancer where elevated levels of androgens are associated with an increased risk of developing ovarian cancer (K. J. Helzlsouer, A. J. Alberg, G. B. Gordon, C. Longcope, T. L. Bush, S. C. Hoffman & G. W. Comstock, *JAMA* 274, 1926-1930 (1995); R. J. Edmondson, J. M. Monaghan & B. R. Davies, *Br J Cancer* 86, 879-885 (2002)). The androgen receptor has been detected in a majority of ovarian cancers (H. A. Risch, *J Natl Cancer Inst* 90, 1774-1786 (1998); B. R. Rao & B. J. Slotman, *Endocr Rev* 12, 14-26 (1991); G. M. Clinton & W. Hua, *Crit. Rev Oncol Hematol* 25, 1-9 (1997)), whereas estrogen receptor-alpha (ERa) and the progesterone receptor are detected in less than 50% of ovarian tumors.

An effective treatment available for advanced prostate cancer is the withdrawal of androgens which are essential for the survival of prostate epithelial cells. Androgen ablation therapy causes a temporary reduction in tumor burden concomitant with a decrease in serum prostate-specific antigen (PSA). Unfortunately prostate cancer can eventually grow again in the absence of testicular androgens (castration-resistant disease) (Huber et al 1987 *Scand J. Urol Nephrol.* 104, 33-39). Castration-resistant prostate cancer is biochemically characterized before the onset of symptoms by a rising titre of serum PSA (Miller et al 1992 *J. Urol.* 147, 956-961). Once the disease becomes castration-resistant most patients succumb to their disease within two years.

The androgen receptor has distinct functional domains that include the carboxy-terminal ligand-binding domain (LBD), a DNA-binding domain (DBD) comprising two zinc finger motifs, and an N-terminus domain (NTD) that contains one or more transcriptional activation domains. Binding of androgen (ligand) to the LBD of the androgen receptor results in its activation such that the receptor can effectively bind to its specific DNA consensus site, termed the androgen response element (ARE), on the promoter and enhancer regions of "normally" androgen regulated genes, such as PSA, to initiate transcription. The androgen receptor can be activated in the absence of androgen by stimulation of the cAMP-dependent protein kinase (PKA) pathway, with interleukin-6 (IL-6) and by various growth factors (Culig et al 1994 *Cancer Res.* 54, 5474-5478; Nazareth et al 1996 *J. Biol. Chem.* 271, 19900-19907; Sadar 1999 *J. Biol. Chem.* 274, 7777-7783; Ueda et al 2002A *J. Biol. Chem.* 277, 7076-7085; and Ueda et al 2002 B *J. Biol. Chem.* 277, 38087-38094). The mechanism of ligand-independent transformation of the androgen receptor AR has been shown to involve: 1) increased nuclear androgen receptor protein suggesting nuclear translocation; 2) increased androgen receptor/ARE complex formation; and 3) the AR-NTD (Sadar 1999 *J. Biol. Chem.* 274, 7777-7783; Ueda et al 2002A *J. Biol. Chem.* 277, 7076-7085; and Ueda et al 2002 B *J. Biol. Chem.* 277, 38087-38094). The androgen receptor may be activated in the absence of testicular androgens by alternative signal transduction pathways in castration-resistant disease, which is consistent with the finding that nuclear androgen receptor protein is present in secondary prostate cancer tumors (Kim et al 2002 *Am. J. Pathol.* 160, 219-226; and van der Kwast et al 1991 *Inter. J. Cancer* 48, 189-193).

Available inhibitors of the androgen receptor include non-steroidal antiandrogens such as bicalutamide, nilutamide, flutamide, enzalutamide, and investigational drug ARN-509, and the steroidal antiandrogen, cyproterone acetate. These antiandrogens target the LBD of the androgen receptor and predominantly fail presumably due to poor affinity and mutations that lead to activation of the androgen receptor by these same antiandrogens (Taplin, M. E., Bubley, G. J., Kom Y. J., Small E. J., Uptonm M., Rajeshkumarm B., Balkm S. P., *Cancer Res.,* 59, 2511-2515 (1999)). These antiandrogens would also have no effect on the recently discovered androgen receptor splice variants that lack the ligand-binding domain (LBD) to result in a constitutively active receptor which promotes progression of androgen-independent prostate cancer (Dehm S M, Schmidt L J, Heemers H V, Vessella R L, Tindall D J., *Cancer Res* 68, 5469-77, 2008; Guo Z, Yang X, Sun F, Jiang R, Linn D E, Chen H, Chen H, Kong X, Melamed J, Tepper C G, Kung H J, Brodie A M, Edwards J, Qiu Y., *Cancer Res.* 69, 2305-13, 2009; Hu et al 2009 Cancer Res. 69, 16-22; Sun et al 2010 J Clin Invest. 2010 120, 2715-30).

Conventional therapy has concentrated on androgen-dependent activation of the androgen receptor through its C-terminal domain. Recent studies developing antagonists to the androgen receptor have concentrated on the C-terminus and specifically: 1) the allosteric pocket and AF-2 activity (Estebanez-Perpiñá et al 2007, *PNAS* 104, 16074-16079); 2) in silico "drug repurposing" procedure for identification of non-steroidal antagonists (Bisson et al 2007, *PNAS* 104, 11927-11932); and coactivator or corepressor interactions (Chang et al 2005, *Mol Endocrinology* 19, 2478-2490; Hur et al 2004, *PLoS Biol* 2, E274; Estebanez-Perpiñá et al 2005, *JBC* 280, 8060-8068; He et al 2004, *Mol Cell* 16, 425-438).

The AR-NTD is also a target for drug development (e.g. WO 2000/001813), since the NTD contains Activation-Function-1 (AF-1) which is the essential region required for androgen receptor transcriptional activity (Jenster et al 1991. Mol. Endocrinol. 5, 1396-404). The AR-NTD importantly plays a role in activation of the androgen receptor in the absence of androgens (Sadar, M. D. 1999 *J. Biol. Chem.* 274, 7777-7783; Sadar M D et al 1999 *Endocr Relat Cancer.* 6, 487-502; Ueda et al 2002 *J. Biol. Chem.* 277, 7076-7085; Ueda 2002 *J. Biol. Chem.* 277, 38087-38094; Blaszczyk et al 2004 *Clin Cancer Res.* 10, 1860-9; Dehm et al 2006 *J Biol. Chem.* 28, 27882-93; Gregory et al 2004 *J Biol. Chem.* 279, 7119-30). The AR-NTD is important in hormonal progression of prostate cancer as shown by application of decoy molecules (Quayle et al 2007, *Proc Natl Acad Sci USA*. 104, 1331-1336).

While the crystal structure has been resolved for the androgen receptor C-terminus LBD, this has not been the case for the NTD due to its high flexibility and intrinisic disorder in solution (Reid et al 2002 *J. Biol. Chem.* 277, 20079-20086) thereby hampering virtual docking drug discovery approaches.

Although progress has been made, there remains a need in the art for additional and/or improved compounds that modulate the androgen receptor. The present disclosure provides these and related advantages.

BRIEF SUMMARY

This disclosure is based in part on the unexpected discovery that certain esters of bisphenol-related compounds have desirable properties for use as modulators of androgen receptor. In particular, the esters described herein are potent modulators of androgen receptor. Further advantages related to use of the described esters for modulation of androgen receptor (in vitro or in vivo) are also expected.

In accordance with one embodiment, there is provided a compound having a structure of Structure I:

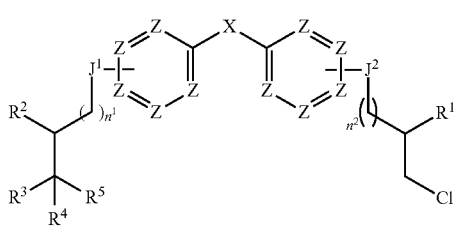

I or a pharmaceutically acceptable salt, tautomer or stereoisomer thereof, wherein $R^1, R^2, R^3, R^4, R^5, J^1, J^2, X, Z, n^1$ and $n^2$ are as defined herein, and wherein at least one of $R^1, R^2$ or $R^3$ is an alkyl, alkenyl, aryl or aralkyl ester. Pharmaceutical compositions comprising a compound of Structure I, a pharmaceutically acceptable carrier and an optional additional therapeutic agent are also provided.

In other embodiments, the present disclosure provides the use of a compound of Structure I or a composition comprising the same, for modulating androgen receptor (AR) activity. Related methods for modulating androgen receptor are also provided.

These and other aspects of the disclosure will be apparent upon reference to the following detailed description. To this end, various references are set forth herein which describe in more detail certain background information, procedures, compounds and/or compositions, and are each hereby incorporated by reference in their entirety.

DETAILED DESCRIPTION

I. Definitions

Figure 1A:
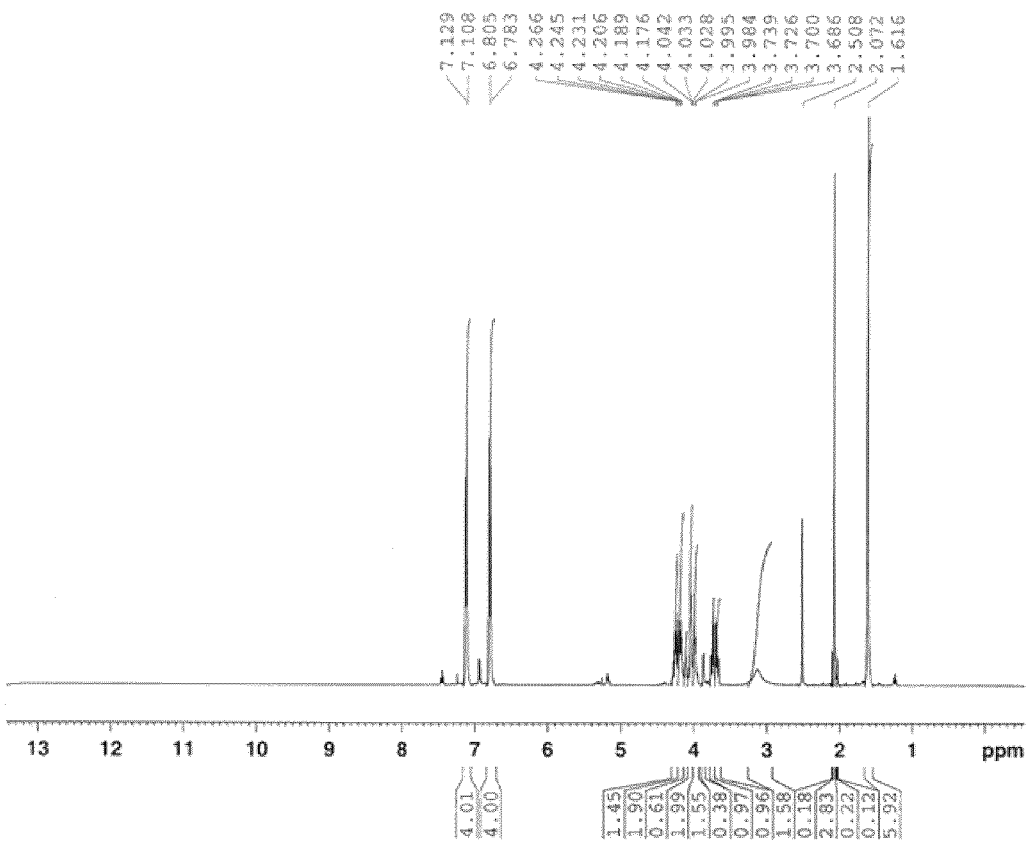
FIG. 1A is a $^1$H NMR spectrum for the compound (S)-3-(4-(2-(4-((S)-3-chloro-2-hydroxypropoxy)phenyl)propan-2-yl)phenoxy)-2-hydroxypropyl acetate.

In the following description, certain specific details are set forth in order to provide a thorough understanding of various embodiments. However, one skilled in the art will understand that the disclosure may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed disclosure.

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. Also, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The terms below, as used herein, have the following meanings, unless indicated otherwise:

"Amino" refers to the —NH$_2$ radical.
"Cyano" refers to the —CN radical.
"Hydroxy" or "hydroxyl" refers to the —OH radical.
"Imino" refers to the =NH substituent.
"Nitro" refers to the —NO$_2$ radical.
"Oxo" refers to the =O substituent.
"Thioxo" refers to the =S substituent.
"Alkyl" refers to a straight, branched or non-aromatic cyclic hydrocarbon ("cycloalkyl") chain radical which is saturated or unsaturated (i.e., contains one or more double and/or triple bonds), having from one to twenty carbon atoms (e.g., one to ten, or one to six carbon atoms), and which is attached to the rest of the molecule by a single bond. Alkyls comprising any number of carbon atoms from 1 to 20 are included. An alkyl comprising up to 10 carbon atoms is a $C_1$-$C_{10}$ alkyl. A $C_1$-$C_{10}$ alkyl includes $C_{10}$ alkyls, $C_9$ alkyls, $C_8$ alkyls, $C_2$ alkyls, $C_6$ alkyls, $C_5$ alkyls, $C_4$ alkyls, $C_3$ alkyls, $C_2$ alkyls and $C_1$ alkyl (i.e., methyl) and includes, for example, and without limitation, saturated $C_1$-$C_{10}$ alkyl, $C_2$-$C_{10}$ alkenyl and $C_2$-$C_{10}$ alkynyl. Non-limiting examples of saturated $C_1$-$C_{10}$ alkyl include methyl, ethyl, n-propyl, i-propyl, sec-propyl, n-butyl, i-butyl, sec-butyl, t-butyl and n-penty, n-hexyl, n-heptane, and the like. Non-limiting examples of $C_2$-$C_{10}$ alkenyl include vinyl, allyl, isopropenyl, 1-propene-2-yl, 1-butene-1-yl, 1-butene-2-yl, 1-butene-3-yl, 2-butene-1-yl, 2-butene-2-yl, penteneyl, hexeneyl, and the like. Non-limiting examples of $C_2$-$C_{10}$ alkynyl include ethynyl, propynyl, butynyl, pentynyl, hexynyl, and the like. Unless stated otherwise specifically in the specification, an alkyl group may be optionally substituted (i.e., a hydrogen atom in the alkyl group may be replaced with an optional substituent). Alkyls include cycloalkyls as defined below.

"Alkylene" or "alkylene chain" refers to a straight or branched divalent hydrocarbon chain linking the rest of the molecule to a radical group, consisting solely of carbon and hydrogen, which is saturated or unsaturated (i.e., contains one or more double and/or triple bonds), and having from one to twenty carbon atoms, e.g., methylene, ethylene, propylene, n-butylene, ethenylene, propenylene, n-butenylene, propynylene, n-butynylene, and the like. The alkylene chain is attached to the rest of the molecule through a single or double bond and to the radical group through a single or double bond. The points of attachment of the alkylene chain to the rest of the molecule and to the radical group can be through one carbon or any two carbons within the chain. Unless stated otherwise specifically in the specification, an alkylene chain may be optionally substituted.

"Aliphatic carbon" refers to a carbon atom which is not aromatic.

"Alkylaminocarbonyl" refers to a radical of the formula —C(=O)NR$_a$R$_b$ where R$_a$ and R$_b$ are each independently an alkyl radical as defined above containing one to twenty carbon atoms. Unless stated otherwise specifically in the specification, an alkylaminocarbonyl group may be optionally substituted.

"Alkylcarbonyl" refers to a radical of the formula —C(=O)R$_a$ where R$_a$ is an alkyl radical as defined above containing one to twenty carbon atoms. Unless stated otherwise specifically in the specification, an alkylcarbonyl group may be optionally substituted.

"Alkoxy" refers to a radical of the formula —OR$_a$ where R$_a$ is an alkyl radical as defined above containing one to twenty carbon atoms. Unless stated otherwise specifically in the specification, an alkoxy group may be optionally substituted.

"Alkylamino" refers to a radical of the formula —NHR$_a$ or —NR$_a$R$_a$ where each R$_a$ is, independently, an alkyl radical as defined above containing one to twenty carbon atoms. Unless stated otherwise specifically in the specification, an alkylamino group may be optionally substituted.

"Aminocarbonyl" refers to a radical of the formula —C(=O)NH$_2$. Unless stated otherwise specifically in the specification, an alkylcarbonyl group may be optionally substituted.

"Aromatic carbon" refers to a carbon atom which is part of an aromatic ring. Aromatic carbons are SP$^2$ hybridzed and from part of a conjugated, unsaturated ring system having 4n+2 electrons in pi orbitals. For example, aromatic carbons may be members on an aryl or heteroaryl ring as defined herein.

"Aryl" refers to a hydrocarbon ring system radical comprising hydrogen, 6 to 18 carbon atoms and at least one aromatic ring. For purposes of this disclosure, the aryl radical may be a monocyclic, bicyclic, tricyclic or tetracyclic ring system, which may include fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" or the prefix "ar-" (such as in "aralkyl") is meant to include aryl radicals that are optionally substituted.

"Aralkyl" refers to a radical of the formula —R$_b$—R$_c$ where R$_b$ is an alkylene chain as defined above and R$_c$ is one or more aryl radicals as defined above, for example, benzyl, diphenylmethyl and the like. Unless stated otherwise specifically in the specification, an aralkyl group may be optionally substituted.

"Carbocycle" refers to a cyclic structure, wherein the bonds that form the ring are each carbon-carbon bonds. Carbocycles generally contain from 3 to 20 carbon atoms within the ring and may be mon, bi or tri-cyclic. Bi and tricyclic carbocycles may be fused (i.e., share two or more common carbon atoms), spiro (i.e., share one common carbon atom) or linked via a linker atom or atoms. Carbocycles, include cycloalkyls and aryls as defined herein. Unless stated otherwise specifically in the specification, carbocycle group may be optionally substituted.

"Cycloalkyl" refers to a stable non-aromatic monocyclic or polycyclic hydrocarbon radical consisting solely of carbon and hydrogen atoms, which may include fused or bridged ring systems, having from three to fifteen carbon atoms, preferably having from three to ten carbon atoms, and which is saturated or unsaturated and attached to the rest of the molecule by a single bond. Monocyclic radicals include, for example, cyclopropyl, cyclobutyl, cyclopentyl, cyclohexyl, cycloheptyl, and cyclooctyl. Polycyclic radicals include, for example, adamantyl, norbornyl, decalinyl, 7,7-dimethyl-bicyclo[2.2.1]heptanyl, and the like. Unless otherwise stated specifically in the specification, a cycloalkyl group may be optionally substituted.

"Deuteroalkyl" refers to an alkyl radical as defined above, wherein at least one of the hydrogen atoms is replaced with a deuterium atom. Unless stated otherwise specifically in the specification, deuteroalkyl group may be optionally substituted.

"Fused" refers to any ring structure described herein which is fused to an existing ring structure in the compounds of the disclosure. When the fused ring is a heterocyclyl ring or a heteroaryl ring, any carbon atom on the existing ring structure which becomes part of the fused heterocyclyl ring or the fused heteroaryl ring may be replaced with a nitrogen atom.

"Halogen" or "halo" refers to fluoro (F), chloro (Cl), bromo (Br) and iodo (I) substituents. Halogen substitutents also include halogen radioisotopes.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group may be optionally substituted.

"Heterocyclyl" or "heterocyclic ring" refers to a stable 3- to 18-membered ring radical which consists of two to twelve carbon atoms and from one to six heteroatoms selected from the group consisting of nitrogen, oxygen and sulfur. Unless stated otherwise specifically in the specification, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, a heterocyclyl group may be optionally substituted. Heterocycles include heteroaryls as defined below.

"Heteroaryl" refers to a 5- to 14-membered ring system radical comprising hydrogen atoms, one to thirteen carbon atoms, one to six heteroatoms selected from the group consisting of nitrogen, oxygen and sulfur, and at least one aromatic ring. For purposes of this disclosure, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl(benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e. thienyl). Unless stated otherwise specifically in the specification, a heteroaryl group may be optionally substituted.

The term "substituted" used herein means any of the above groups (i.e., alkyl, alkylene, alkylaminocarbonyl, alkylcarbonyl, alkoxy, alkylamino, aminocarbonyl, cycloalkyl, aryl, aralkyl, carbocycle, deuteroalkyl, haloalkyl, heterocyclyl, and/or heteroaryl) wherein at least one hydrogen atom is replaced by a bond to a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, glycines, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo (i.e., C=O), carbonyl, carboxyl, and ester groups; and nitrogen in groups such as imines, oximes, hydrazones, and nitriles.

For example, "substituted" includes any of the above groups in which one or more hydrogen atoms are replaced with —$NR_gR_h$, —$NR_gC(=O)R_h$, —$NR_gC(=O)NR_gR_h$, —$NR_gC(=O)OR_h$, —$NR_gSO_2R_h$, —$OC(=O)NR_gR_h$, —$OR_g$, —$SR_g$, —$SOR_g$, —$SO_2R_g$, —$OSO_2R_g$, —$SO_2OR_g$, =$NSO_2R_g$, and —$SO_2NR_gR_h$.

"Substituted also means any of the above groups in which one or more hydrogen atoms are replaced with —$C(=O)R_g$, —$C(=O)OR_g$, —$C(=O)NR_gR_h$, —$CH_2SO_2R_g$, —$CH_2SO_2NR_gR_h$. In the foregoing, $R_g$ and $R_h$ are the same or different and independently hydrogen, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl.

"Substituted" further means any of the above groups in which one or more hydrogen atoms are replaced by a bond to an amino, cyano, hydroxyl, imino, nitro, oxo, thioxo, halo, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl group. In addition, each of the foregoing substituents may also be optionally substituted with one or more of the above substituents.

"Prodrug" is meant to indicate a compound that may be converted under physiological conditions or by solvolysis to a biologically active compound. Thus, the term "prodrug" refers to a metabolic precursor of a compound of the disclosure that is pharmaceutically acceptable. A prodrug may be active or inactive when administered to a subject in need thereof, but is converted in vivo to an active (or more active) compound. Prodrugs are typically rapidly transformed in vivo to yield the parent compound, for example, by hydrolysis in blood. The prodrug compound often offers advantages of solubility, tissue compatibility or delayed release in a mammalian organism (see, Bundgard, H., Design of Prodrugs (1985), pp. 7-9, 21-24 (Elsevier, Amsterdam)). A discussion of prodrugs is provided in Higuchi, T., et al., A.C.S. Symposium Series, Vol. 14, and in Bioreversible Carriers in Drug Design, Ed. Edward B. Roche, American Pharmaceutical Association and Pergamon Press, 1987. The present disclosure is meant to ecompass all compounds of structure I, whether acting as a prodrug or the active compound itself, or both.

The disclosure disclosed herein is also meant to encompass all pharmaceutically acceptable compounds of Structure (I) being isotopically-labelled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^2H$, $^3H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. These radiolabelled compounds could be useful to help determine or measure the effectiveness of the compounds, by characterizing, for example, the site or mode of action, or binding affinity to pharmacologically important site of action. Certain isotopically-labelled compounds of Structure (I), for example, those incorporating a radioactive isotope, are useful in drug and/or substrate tissue distribution studies. The radioactive isotopes tritium, i.e. $^3H$, and carbon-14, i.e. $^{14}C$, are particularly useful for this purpose in view of their ease of incorporation and ready means of detection.

Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$, $I^{123}$ and $^{13}N$, can be useful in Positron Emission Topography (PET) or Single Photon Emission Computed Tomography (SPECT) studies for examining substrate receptor occupancy. Isotopically-labeled compounds of Structure (I) can generally be prepared by conventional techniques known to those skilled in the art or by processes analogous to those described in the Preparations and Examples as set out below using an appropriate isotopically-labeled reagent in place of the non-labeled reagent previously employed.

The disclosure disclosed herein is also meant to encompass the in vivo metabolic products of the disclosed compounds. Such products may result from, for example, the oxidation, reduction, hydrolysis, amidation, esterification, and the like of the administered compound, primarily due to enzymatic processes. Accordingly, the disclosure includes compounds produced by a process comprising administering a compound of this disclosure to a mammal for a period of time sufficient to yield a metabolic product thereof. Such products are typically identified by administering a radiolabelled compound of the disclosure in a detectable dose to an animal, such as rat, mouse, guinea pig, monkey, or to human, allowing sufficient time for metabolism to occur, and isolating its conversion products from the urine, blood or other biological samples.

"Stable compound" and "stable structure" are meant to indicate a compound that is sufficiently robust to survive isolation to a useful degree of purity from a reaction mixture, and formulation into an efficacious therapeutic agent.

"Mammal" includes humans and both domestic animals such as laboratory animals and household pets (e.g., cats, dogs, swine, cattle, sheep, goats, horses, rabbits), and non-domestic animals such as wildlife and the like.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Often crystallizations produce a solvate of the compound of the disclosure. As used herein, the term "solvate" refers to an aggregate that comprises one or more molecules of a compound of the disclosure with one or more molecules of solvent. The solvent may be water, in which case the solvate may be a hydrate. Alternatively, the solvent may be an organic solvent. Thus, the compounds of the present disclosure may exist as a hydrate, including a monohydrate, dihydrate, hemihydrate, sesquihydrate, trihydrate, tetrahydrate and the like, as well as the corresponding solvated forms. The compound of the disclosure may be true solvates, while in other cases, the compound of the disclosure may merely retain adventitious water or be a mixture of water plus some adventitious solvent.

A "pharmaceutical composition" refers to a formulation of a compound of the disclosure and a medium generally accepted in the art for the delivery of the biologically active compound to mammals, e.g., humans. Such a medium includes all pharmaceutically acceptable carriers, diluents or excipients therefor.

An "effective amount" refers to a therapeutically effective amount or a prophylactically effective amount. A "therapeutically effective amount" refers to an amount effective, at dosages and for periods of time necessary, to achieve the desired therapeutic result, such as reduced tumor size, increased life span or increased life expectancy. A therapeutically effective amount of a compound may vary according to factors such as the disease state, age, sex, and weight of the subject, and the ability of the compound to elicit a desired response in the subject. Dosage regimens may be adjusted to provide the optimum therapeutic response. A therapeutically effective amount is also one in which any toxic or detrimental effects of the compound are outweighed by the therapeutically beneficial effects.

A "prophylactically effective amount" refers to an amount effective, at dosages and for periods of time necessary, to achieve the desired prophylactic result, such as smaller tumors, increased life span, increased life expectancy or prevention of the progression of prostate cancer to an androgen-independent form. Typically, a prophylactic dose is used in subjects prior to or at an earlier stage of disease, so that a prophylactically effective amount may be less than a therapeutically effective amount.

"Treating" or "treatment" as used herein covers the treatment of the disease or condition of interest in a mammal, preferably a human, having the disease or condition of interest, and includes:

(i) preventing the disease or condition from occurring in a mammal, in particular, when such mammal is predisposed to the condition but has not yet been diagnosed as having it;
(ii) inhibiting the disease or condition, i.e., arresting its development;
(iii) relieving the disease or condition, i.e., causing regression of the disease or condition; or
(iv) relieving the symptoms resulting from the disease or condition, i.e., relieving pain without addressing the underlying disease or condition. As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

The compounds of the disclosure, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present disclosure is meant to include all such possible isomers, as well as their racemic and optically pure forms.

Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centres of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present disclosure contemplates various stereoisomers and mixtures thereof and includes "enantiomers", which refers to two stereoisomers whose molecules are nonsuperimposeable mirror images of one another.

A "tautomer" refers to a proton shift from one atom of a molecule to another atom of the same molecule accompanied by a switch of a single bond and adjacent double bond. The present disclosure includes tautomers of any said compounds.

The chemical naming protocol and structure diagrams used herein are a modified form of the I.U.P.A.C. nomenclature system, using the ACD/Name Version 9.07 software program and/or ChemDraw Ultra Version 11.0.1 software naming program (CambridgeSoft), wherein the compounds of the disclosure are named herein as derivatives of the central core structure. For complex chemical names employed herein, a substituent group is named before the group to which it attaches. For example, cyclopropylethyl comprises an ethyl backbone with cyclopropyl substituent. Except as described below, all bonds are identified in the chemical structure diagrams herein, except for some carbon atoms, which are assumed to be bonded to sufficient hydrogen atoms to complete the valency.

As used herein, the symbol

(hereinafter may be referred to as "a point of attachment bond") denotes a bond that is a point of attachment between two chemical entities, one of which is depicted as being attached to the point of attachment bond and the other of which is not depicted as being attached to the point of attachment bond.

For example,

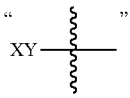

indicates that the chemical entity "XY" is bonded to another chemical entity via the point of attachment bond. Furthermore, the specific point of attachment to the non-depicted chemical entity may be specified by inference.

For example, the compound $CH_3-R^3$, wherein $R^3$ is H or

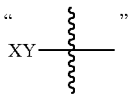

infers that when $R^3$ is "XY", the point of attachment bond is the same bond as the bond by which $R^3$ is depicted as being bonded to $CH_3$.

II. Compounds and Compositions

As noted above, certain embodiments of the present disclosure are directed to compounds useful for modulation of androgen receptor. As such, the compounds find utility for treatment of various cancers, including various types of prostate cancers. The esters derivatives described herein are expected to have improved properties relative to other known androgen receptor modulators which do not contain the described ester moieties.

Accordingly, one embodiment of the present disclosure is directed to a compound having a structure of Structure I:

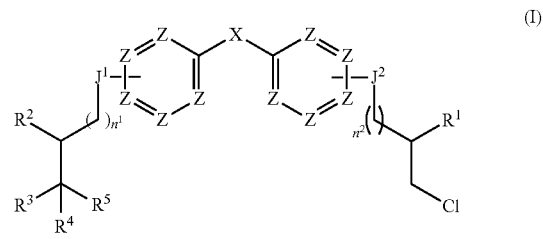

(I)

or a pharmaceutically acceptable salt, tautomer or stereoisomer thereof, wherein:

$J^1$ and $J^2$ are each independently —O—, —S(O)$_m$—, —NR$^6$— or —(CR$^6$R$^7$)—;

X is a direct bond, —C(R$^8$R$^9$)—, —C(=CR$^8$R$^9$)—, —C(R$^8$R$^9$)-aryl-C(R$^8$R$^9$)—, —C(=CR$^8$R$^9$)-aryl-C(=CR$^8$R$^9$)—, —C(=CR$^8$R$^9$)-aryl-C(R$^8$R$^9$)—, —C(R$^8$R$^9$)-aryl-C(=CR$^8$R$^9$)—, —O—, —S(O)$_m$—, —N(R$^6$)—, —CH(NR$^6$R$^7$)—, —C(=NOR$^6$)—, —C(=N—NHR$^{10}$)—, —C(=NR$^6$)— or —C(=O)—;

Z is, at each occurrence, independently —C(R$^{11}$)— or —N—;

$R^1$ is hydroxyl, —OR$^{12}$ or —OC(=O)R$^{13}$;

$R^2$ and $R^3$ are each independently hydroxyl, halo, —OR$^{12}$ or —OC(=O)R$^{13}$;

$R^4$ and $R^5$ are each independently H or halo;

$R^6$ and $R^7$ are, at each occurrence, independently H or $C_{1-10}$ alkyl;

$R^8$ and $R^9$ are, at each occurrence, independently, H, hydroxyl, halo, $C_1$-$C_{10}$ alkyl, $C_1$-$C_{10}$ haloalkyl, $C_1$-$C_{10}$ deuteroalkyl, $C_1$-$C_{10}$ alkoxy, aryl, aralkyl, —S(O)$_r$—R$^{14}$ or —NR$^6$R$^7$, or $R^8$ and $R^9$ may join to form a mono-, bi- or tri-cyclic carbocycle or heterocycle containing from 3 to 20 carbon atoms;

$R^{10}$ is H, $C_1$-$C_{10}$ alkyl, aryl, aminocarbonyl, $C_1$-$C_{10}$ alkylcarbonyl or $C_1$-$C_{10}$ alkylaminocarbonyl;

$R^{11}$ is, at each occurrence, independently H, halo or $C_1$-$C_{10}$ alkyl;

$R^{12}$ is, at each occurrence, independently $C_1$-$C_{20}$ alkyl or $C_2$-$C_{20}$ alkenyl;

$R^{13}$ is, at each occurrence, independently $C_1$-$C_{20}$ alkyl, $C_2$-$C_{20}$ alkenyl, aryl or aralkyl, wherein the $C_1$-$C_{20}$ alkyl does not include optional amino or alkylamino substituents and each aliphatic carbon of the $C_1$-$C_{20}$ alkyl, $C_2$-$C_{20}$ alkenyl or aralkyl groups may optionally be replaced with —O— or —S(O)$_m$—;

$R^{14}$ is H, $C_1$-$C_{10}$ alkyl or aryl;

m is, at each occurrence, independently 0, 1 or 2;

$n^1$ and $n^2$ are each independently 0, 1, 2, 3, 4 or 5, wherein at least one of $R^1$, $R^2$ or $R^3$ is —OC(=O)R$^{13}$.

In other embodiments, the compound has the following structure (Ia):

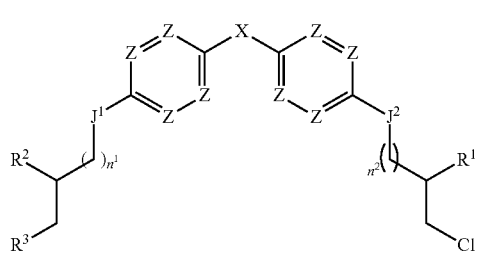

(Ia)

In still other embodiments, the compound has the following structure (Ib):

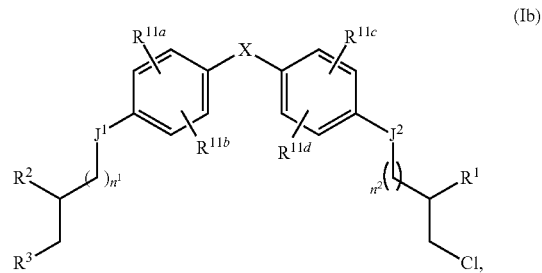

(Ib)

wherein $R^{11a}$, $R^{11b}$, $R^{11c}$ and $R^{11d}$ are each independently H, halo or $C_1$-$C_{10}$ alkyl.

In any of the foregoing embodiments, $J^1$ and $J^2$ are each —O—.

In other of any of the foregoing embodiments, X is —C(R$^8$R$^9$)—.

In still other of the foregoing embodiments, the compound has the following structure (Ic):

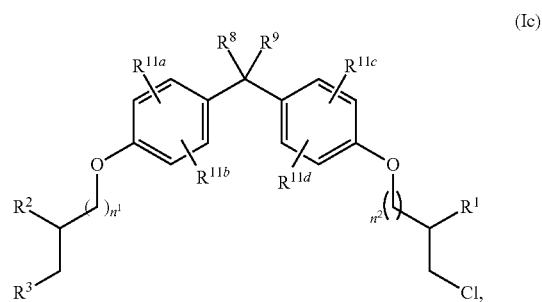

(Ic)

wherein $R^{11a}$, $R^{11b}$, $R^{11c}$ and $R^{11d}$ are each independently H, halo or $C_1$-$C_{10}$ alkyl.

In yet other of the foregoing embodiments, the compound has one of the following structures (Id), (Ie), (If), (Ig), (Ih), (Ii) or (Ij):

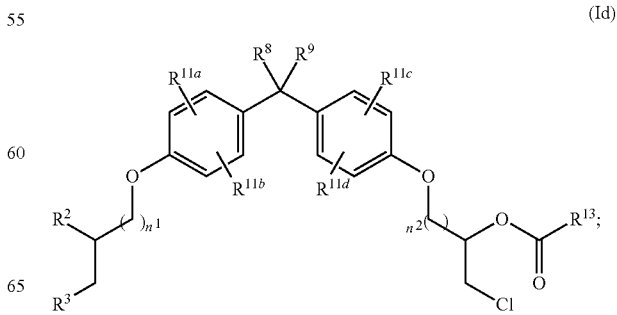

(Id)

wherein $R^{11a}$, $R^{11b}$, $R^{11c}$ and $R^{11d}$ are each independently H, halo or $C_1$-$C_{10}$ alkyl.

In still more of the foregoing embodiments, the compound has one of the following structures (Ik), (Il), (Im), (In), (Io) or (Ip):

(In)

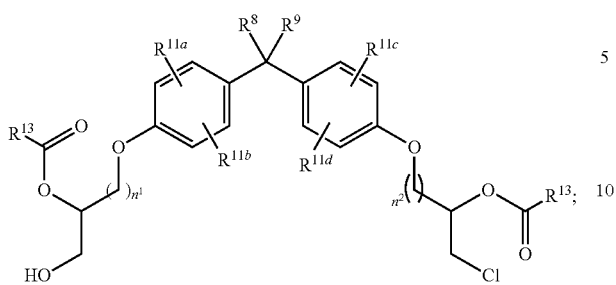

(Io)

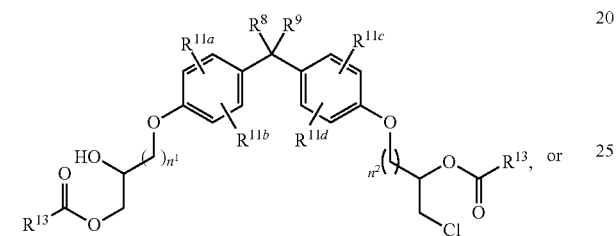

(Ip)

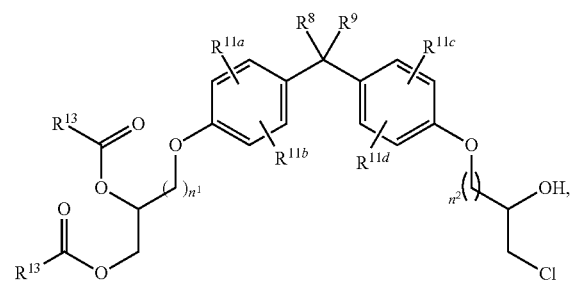

wherein $R^{11a}$, $R^{11b}$, $R^{11c}$ and $R^{11d}$ are each independently H, halo or $C_1$-$C_{10}$ alkyl.

In other embodiments of any of the foregoing, the compound has one of the following structures (Iq), (Ir) or (Is):

(Iq)

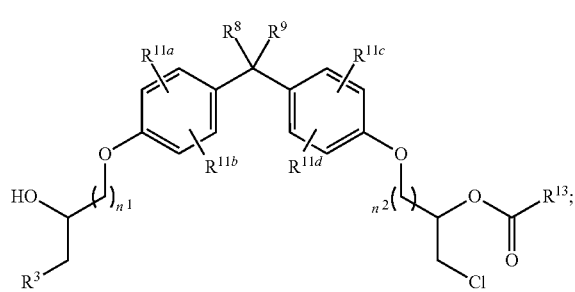

(Ir)

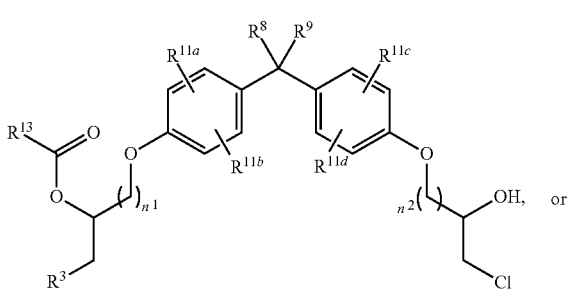

(Is)

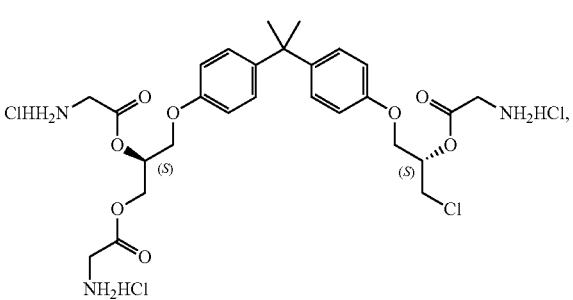

In some embodiments of the foregoing $R^3$ is $-OR^{12}$. For example, in some embodiments $R^{12}$ is $C_1$-$C_6$ alkyl. In other embodiments, $R^{12}$ is methyl, isopropyl or n-butyl.

In still other embodiments of any of the foregoing, $R^3$ is halo. For example, in some embodiments $R^3$ is fluoro.

In certain embodiments, the compounds include at least one alkyl ester. Accordingly, in some embodiments each $R^{13}$ is independently $C_1$-$C_{20}$ alkyl, for example $C_1$-$C_6$ alkyl. In some of these embodiments, the $C_1$-$C_{20}$ or $C_1$-$C_6$ alkyl is unsubstituted. In some further embodiments, each $R^{13}$ is independently methyl, ethyl or propyl. In even further embodiments, each $R^{13}$ is methyl.

In yet other embodiments, the $R^{13}$ is substituted. For example, in certain embodiments, the $R^{13}$ is a substituted $C_1$-$C_{20}$ alkyl or a substituted $C_1$-$C_6$ alkyl. In particular embodiments, the $R^{13}$ substituted alkyl comprises a Nitrogen substituent. In an aspect, the Nitrogen substituted $R^{13}$ alkyl is methyl, which together with the adjacent carbonyl group forms a glycine substituent. In a particular aspect, the $R^{13}$ substituted alkyl is a methyl with a Nitrogen and a terminal Chlorine, i.e. $NH_2HCl$.

In particular embodiments, the glycince substituted compounds with a terminal Chlorine are as follows:

-continued

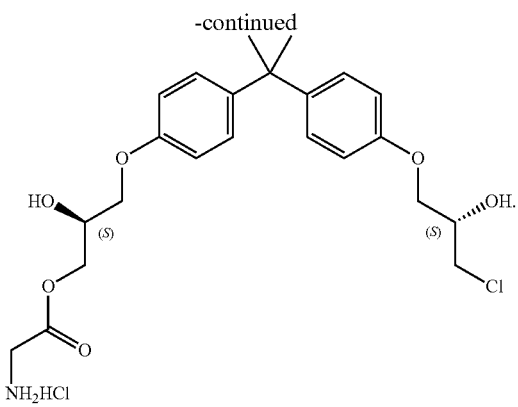

In more embodiments of any of the foregoing compounds of Structure I, $R^8$ and $R^9$ are each independently $C_1$-$C_6$ alkyl. For example, in some embodiments $R^8$ and $R^9$ are each methyl.

In still other embodiments of any of the foregoing compounds of Structure I, at least one $R^{11}$ is H or at least one of $R^{11a}$, $R^{11b}$, $R^{11c}$ or $R^{11d}$ is H. For example, in some embodiments each $R^{11}$ is H or each of $R^{11a}$, $R^{11b}$, $R^{11c}$ and $R^{11d}$ is H.

In more embodiments of the foregoing, at least one of $n^1$ or $n^2$ is 1. In other embodiments of the foregoing, $n^1$ and $n^2$ are each 1. In some embodiments, $n^1$ is 2. In some embodiments, $n^1$ is 3. In some embodiments, $n^1$ is 4. In some embodiments, $n^1$ is 2, $n^2$ is 2. In some embodiments, $n^1$ is 3. In some embodiments, $n^1$ is 4. In some embodiments, $n^1$ is 5.

In other embodiments, $R^4$ and $R^5$ are each H. In some different embodiments, at least one of $R^4$ or $R^5$ is halo. For example, in some embodiments $R^4$ and $R^5$ are each halo. In some of these foregoing embodiments, halo is fluoro.

In some of the forgoing embodiments, $R^{13}$ is $C_1$-$C_{20}$ alkyl, $C_2$-$C_{20}$ alkenyl or aralkyl, and at least one of the aliphatic carbons of the $C_1$-$C_{20}$ alkyl, $C_2$-$C_{20}$ alkenyl or aralkyl group is substituted with a substituent. For example, the substituent may be selected from hydroxyl, halo, oxo and alkoxy. In other embodiments, the $C_1$-$C_{20}$ alkyl, $C_2$-$C_{20}$ alkenyl or aralkyl is unsubstituted.

In some other embodiments, $R^{13}$ is aryl or aralkyl, and at least one of the aromatic carbons of the aryl or aralkyl group is substituted with a substituent For example, in some embodiments the substituent is selected from hydroxyl, halo and alkoxy. In other embodiments, the aryl or aralkyl is unsubstituted.

The compounds described herein are meant to include all racemic mixtures and all individual enantiomers or combinations thereof, whether or not they are specifically depicted herein. Accordingly, the compounds include racemic mixtures, enantiomers and diastereomers of any of the compounds described herein. Tautomers of any of the compounds of Structure I are also included within the scope of the disclosure.

As noted above, the compounds of the present disclosure (i.e., compounds of Structure 1) may contain one or more asymmetric centers. Accordingly, in some embodiments the compounds are mixtures of different enantiomers (e.g., R and S) or different diastereomers. In other embodiments, the compounds are pure (or enriched) enantiomers or diastereomers. For purpose of clarity, the chiral carbons are not always depicted in the compounds; however, the present disclosure includes all stereoisomers (pure and mixtures) of all compounds of Structure I.

By way of example, compounds of Structure I contain at least two stereocenters marked with an * below:

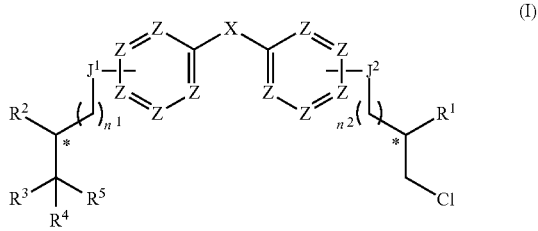

Although the compounds are generally depicted as above, the scope of the disclosure includes all possible stereoisomers. For example, with respect to Structure I, the disclosure also includes the following stereoisomers (I'), (I"), (I'") and (I""):

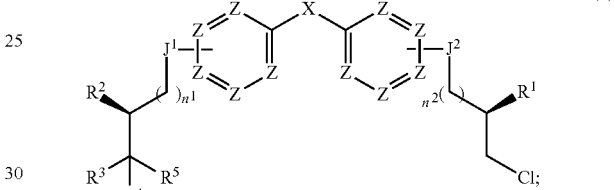

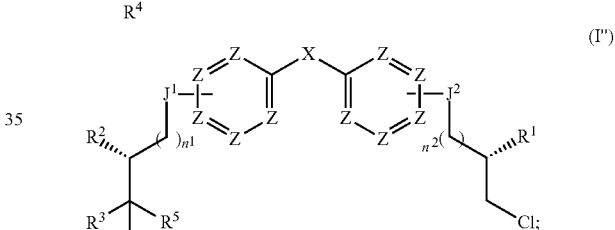

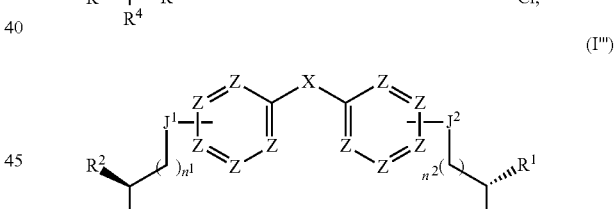

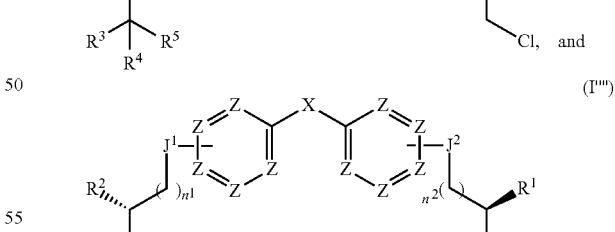

In an analogous fashion, the disclosure includes all possible stereoisomers of all compounds of Structure I (e.g., Ia, Ib, Ic, Id, Ie, If, Ig, Ih, Ii, Ij, Ik, Il, Im, In, Io, Ip, Iq, Ir and Is), including the compounds provided in Table 1. One of ordinary skill in the art will readily understand how to derive all possible stereoisomers, especially in reference to the above example.

In other particular embodiments of the compounds, as described anywhere herein, the following compounds in Table 1 are provided.

TABLE 1

Representative Compounds

| No. | Structure |
|---|---|
| 1 | 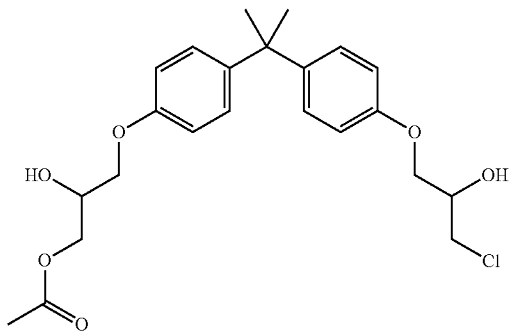 [SMILES: CC(=O)OCC(O)COc1ccc(C(C)(C)c2ccc(OCC(O)CCl)cc2)cc1] |
| 1a | 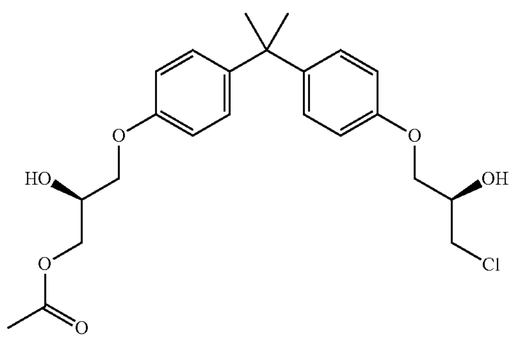 [SMILES: CC(=O)OC[C@@H](O)COc1ccc(C(C)(C)c2ccc(OC[C@@H](O)CCl)cc2)cc1] |
| 1b | 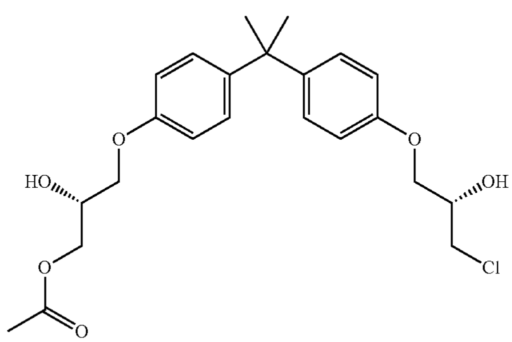 [SMILES: CC(=O)OC[C@H](O)COc1ccc(C(C)(C)c2ccc(OC[C@H](O)CCl)cc2)cc1] |
| 1c | 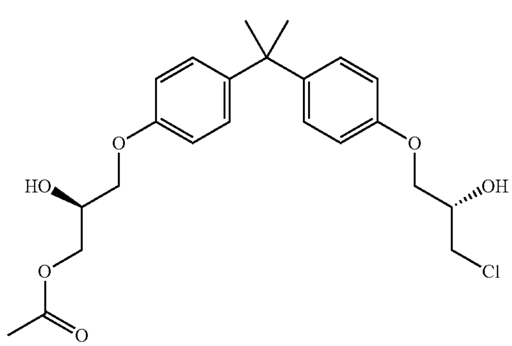 [SMILES: CC(=O)OC[C@@H](O)COc1ccc(C(C)(C)c2ccc(OC[C@H](O)CCl)cc2)cc1] |

TABLE 1-continued

Representative Compounds

| No. | Structure |
|---|---|
| 1d | 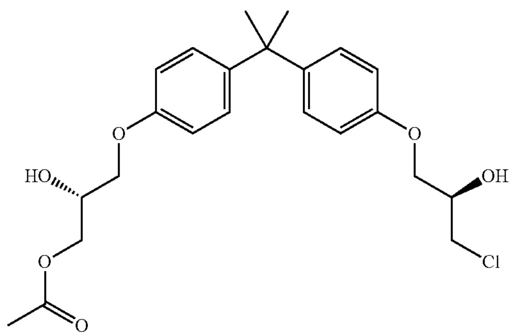 [SMILES: CC(=O)OC[C@H](O)COc1ccc(C(C)(C)c2ccc(OC[C@@H](O)CCl)cc2)cc1] |
| 2 | 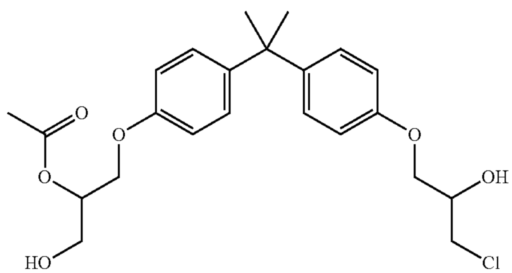 |
| 2a | 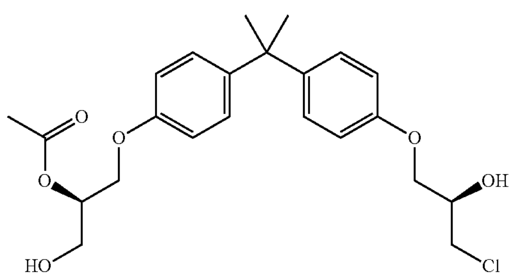 [SMILES: CC(=O)O[C@H](CO)COc1ccc(C(C)(C)c2ccc(OC[C@@H](O)CCl)cc2)cc1] |
| 2b | 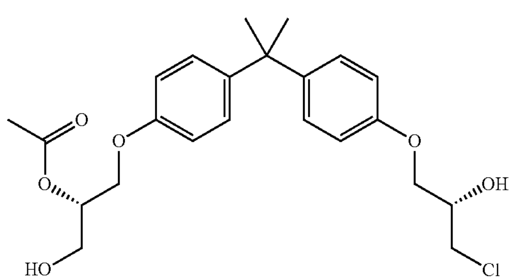 [SMILES: CC(=O)O[C@@H](CO)COc1ccc(C(C)(C)c2ccc(OC[C@H](O)CCl)cc2)cc1] |
| 2c | 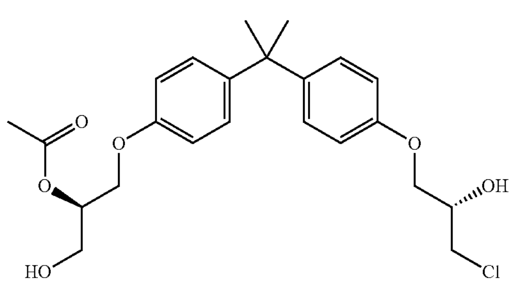 [SMILES: CC(=O)O[C@H](CO)COc1ccc(C(C)(C)c2ccc(OC[C@H](O)CCl)cc2)cc1] |

TABLE 1-continued

Representative Compounds

| No. | Structure |
|---|---|
| 2d | 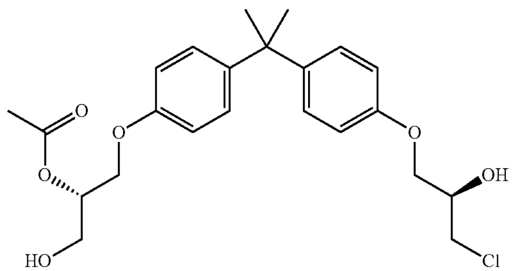 [SMILES: CC(=O)O[C@@H](CO)COc1ccc(C(C)(C)c2ccc(OC[C@@H](O)CCl)cc2)cc1] |
| 3 | 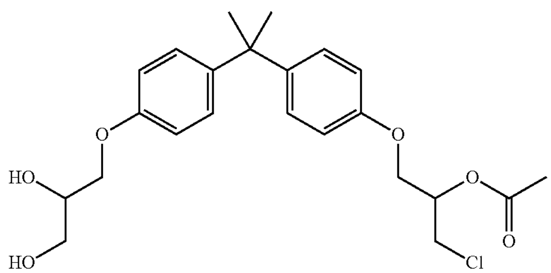 [SMILES: CC(=O)OC(CCl)COc1ccc(C(C)(C)c2ccc(OCC(O)CO)cc2)cc1] |
| 3a | 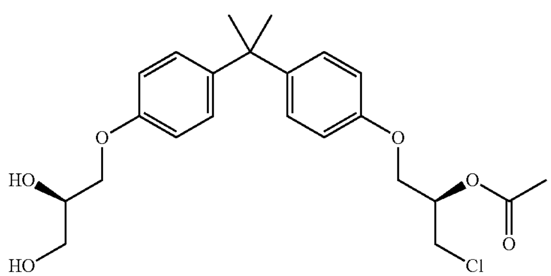 [SMILES: CC(=O)O[C@@H](CCl)COc1ccc(C(C)(C)c2ccc(OC[C@H](O)CO)cc2)cc1] |
| 3b | 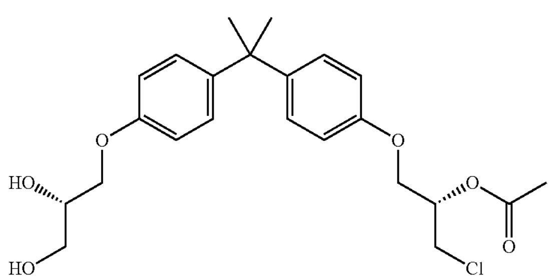 [SMILES: CC(=O)O[C@H](CCl)COc1ccc(C(C)(C)c2ccc(OC[C@@H](O)CO)cc2)cc1] |
| 3c | 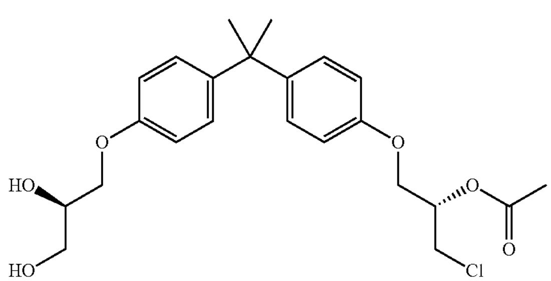 [SMILES: CC(=O)O[C@H](CCl)COc1ccc(C(C)(C)c2ccc(OC[C@H](O)CO)cc2)cc1] |

TABLE 1-continued
Representative Compounds
| No. | Structure |
|---|---|
| 3d | 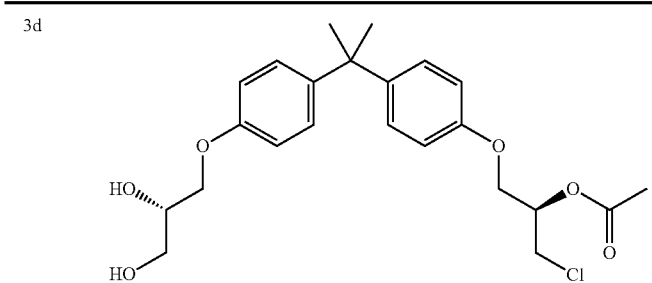 |
| 4 | 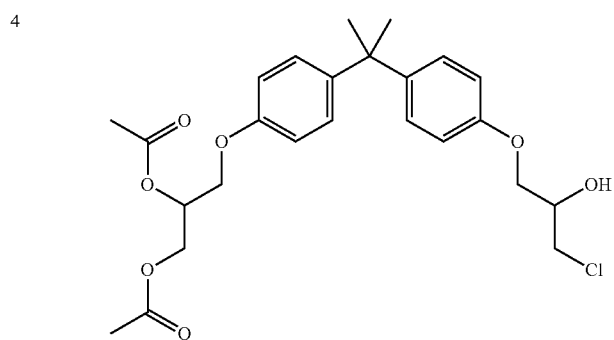 |
| 4a | 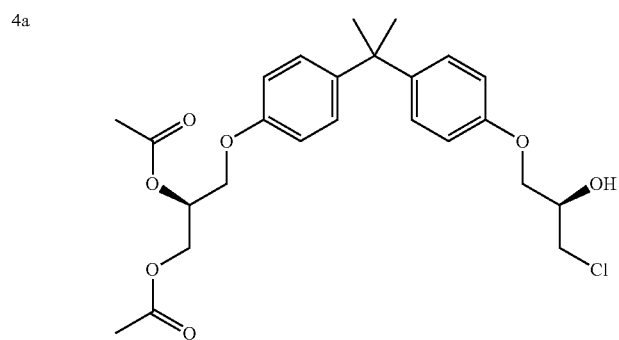 |
| 4b | 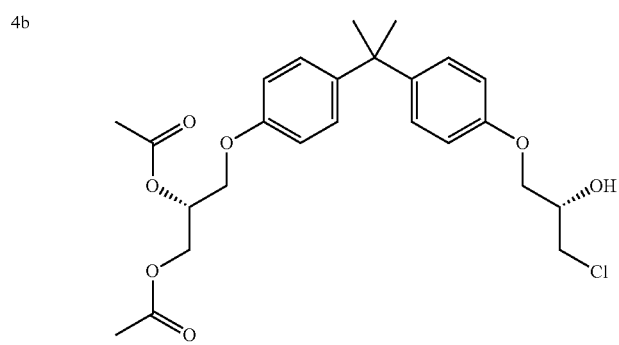 |

TABLE 1-continued

Representative Compounds

| No. | Structure |
|-----|-----------|
| 4c  | 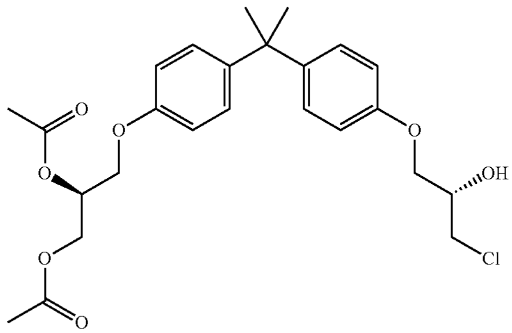 [SMILES: CC(=O)OC[C@H](COc1ccc(C(C)(C)c2ccc(OC[C@H](O)CCl)cc2)cc1)OC(C)=O]          |
| 4d  | 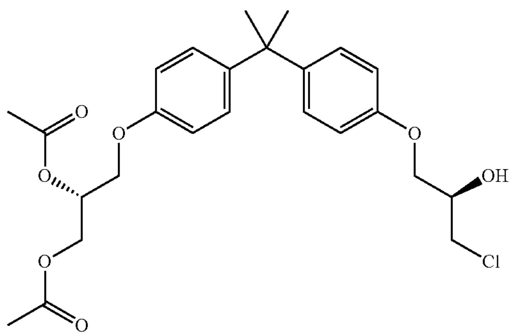 [SMILES: CC(=O)OC[C@@H](COc1ccc(C(C)(C)c2ccc(OC[C@@H](O)CCl)cc2)cc1)OC(C)=O]          |
| 5   | 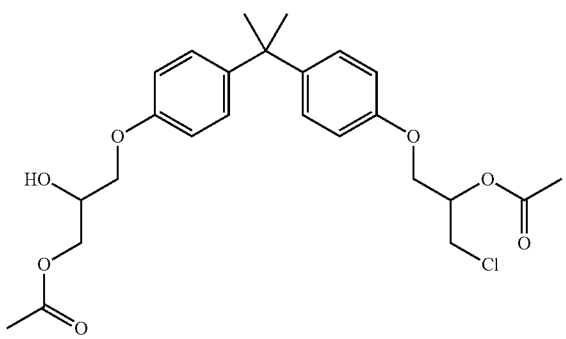 [SMILES: CC(=O)OCC(O)COc1ccc(C(C)(C)c2ccc(OCC(CCl)OC(C)=O)cc2)cc1]          |
| 5a  | 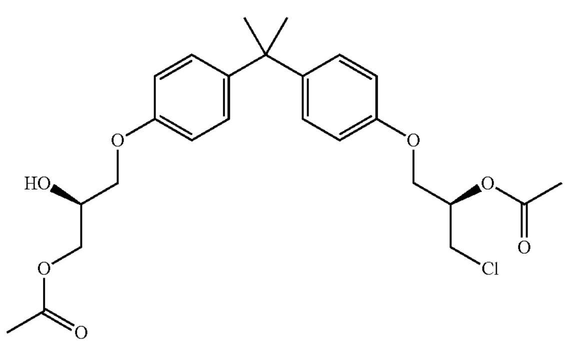 [SMILES: CC(=O)OC[C@@H](O)COc1ccc(C(C)(C)c2ccc(OC[C@H](CCl)OC(C)=O)cc2)cc1]          |

TABLE 1-continued

Representative Compounds

| No. | Structure |
|---|---|
| 5b | 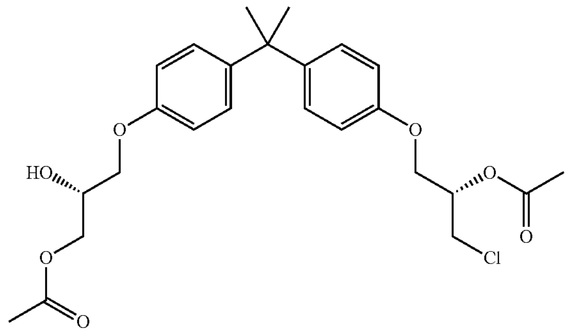 [SMILES: CC(=O)OC[C@H](O)COc1ccc(C(C)(C)c2ccc(OC[C@@H](CCl)OC(C)=O)cc2)cc1] |
| 5c | 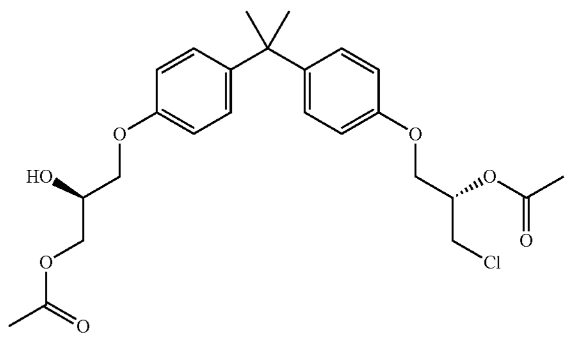 [SMILES: CC(=O)OC[C@@H](O)COc1ccc(C(C)(C)c2ccc(OC[C@@H](CCl)OC(C)=O)cc2)cc1] |
| 5d | 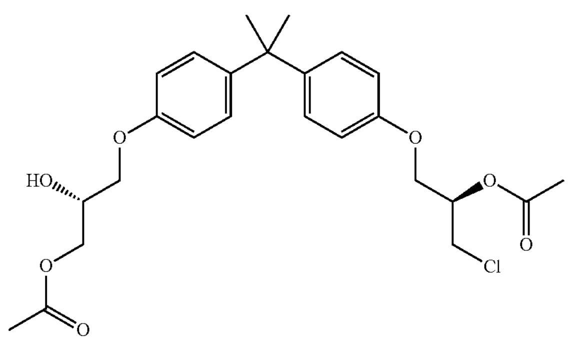 [SMILES: CC(=O)OC[C@H](O)COc1ccc(C(C)(C)c2ccc(OC[C@H](CCl)OC(C)=O)cc2)cc1] |
| 6 | 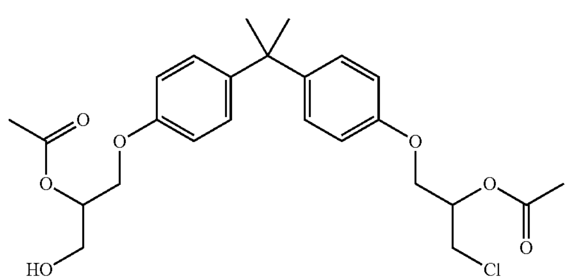 [SMILES: CC(=O)OC(CO)COc1ccc(C(C)(C)c2ccc(OCC(CCl)OC(C)=O)cc2)cc1] |

TABLE 1-continued

Representative Compounds

| No. | Structure |
|---|---|
| 6a | 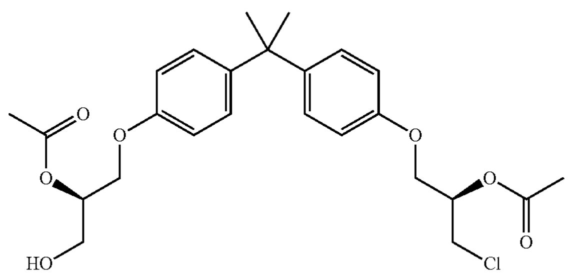 |
| 6b | 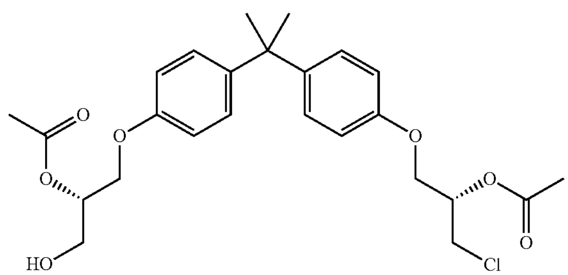 [SMILES: CC(=O)O[C@H](CCl)COc1ccc(C(C)(C)c2ccc(OC[C@H](CO)OC(C)=O)cc2)cc1] |
| 6c | 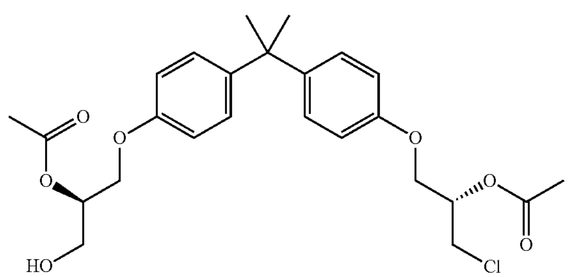 |
| 6d | 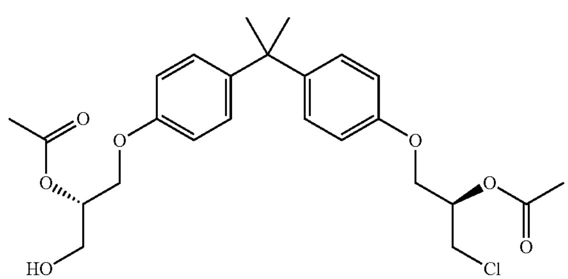 [SMILES: CC(=O)O[C@@H](CO)COc1ccc(C(C)(C)c2ccc(OC[C@H](CCl)OC(C)=O)cc2)cc1] |
| 7 | 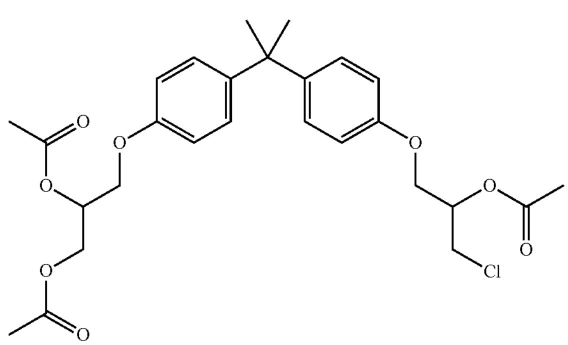 [SMILES: CC(=O)OCC(COc1ccc(C(C)(C)c2ccc(OCC(CCl)OC(C)=O)cc2)cc1)OC(C)=O] |

TABLE 1-continued

Representative Compounds

| No. | Structure |
|---|---|
| 7a | 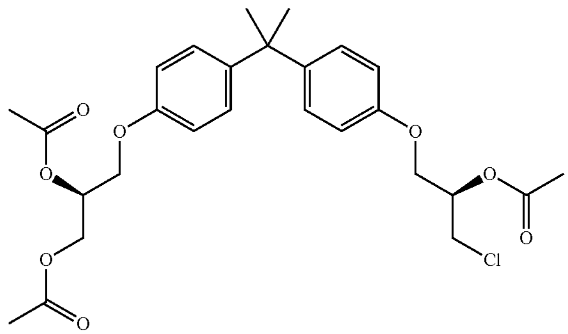 [SMILES: CC(=O)OC[C@H](COc1ccc(C(C)(C)c2ccc(OC[C@H](CCl)OC(C)=O)cc2)cc1)OC(C)=O] |
| 7b | 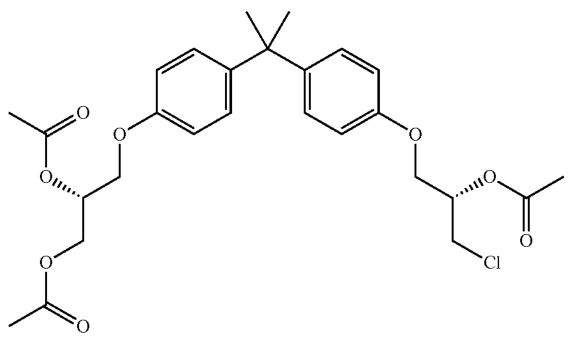 [SMILES: CC(=O)OC[C@@H](COc1ccc(C(C)(C)c2ccc(OC[C@@H](CCl)OC(C)=O)cc2)cc1)OC(C)=O] |
| 7c | 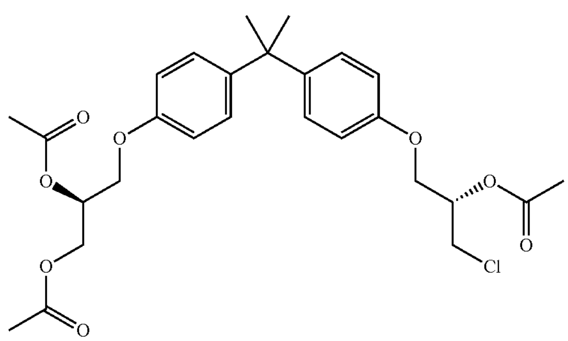 [SMILES: CC(=O)OC[C@H](COc1ccc(C(C)(C)c2ccc(OC[C@@H](CCl)OC(C)=O)cc2)cc1)OC(C)=O] |
| 7d | 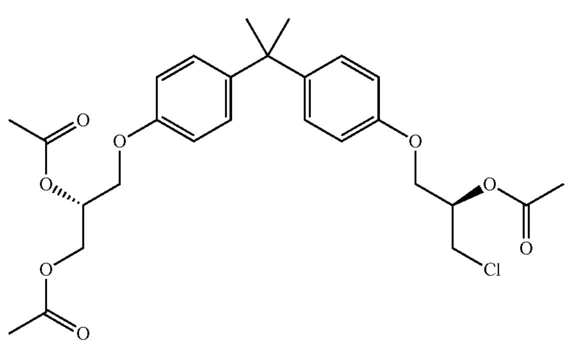 [SMILES: CC(=O)OC[C@@H](COc1ccc(C(C)(C)c2ccc(OC[C@H](CCl)OC(C)=O)cc2)cc1)OC(C)=O] |

TABLE 1-continued

Representative Compounds

| No. | Structure |
|---|---|
| 8 | 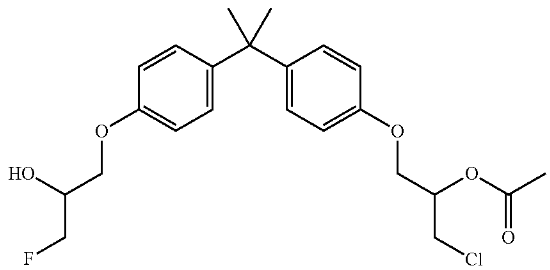 [SMILES: CC(=O)OC(CCl)COc1ccc(C(C)(C)c2ccc(OCC(O)CF)cc2)cc1] |
| 8a | 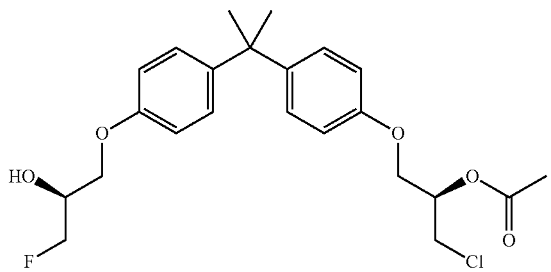 [SMILES: CC(=O)O[C@@H](CCl)COc1ccc(C(C)(C)c2ccc(OC[C@H](O)CF)cc2)cc1] |
| 8b | 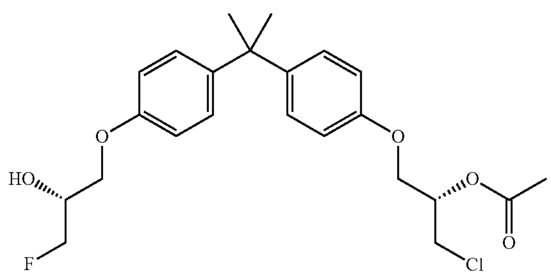 [SMILES: CC(=O)O[C@H](CCl)COc1ccc(C(C)(C)c2ccc(OC[C@@H](O)CF)cc2)cc1] |
| 8c | 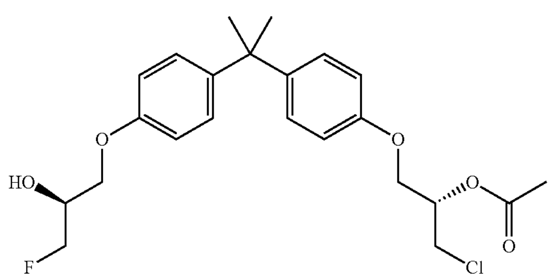 [SMILES: CC(=O)O[C@H](CCl)COc1ccc(C(C)(C)c2ccc(OC[C@H](O)CF)cc2)cc1] |
| 8d | 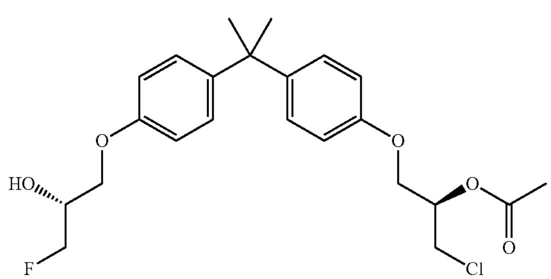 [SMILES: CC(=O)O[C@@H](CCl)COc1ccc(C(C)(C)c2ccc(OC[C@@H](O)CF)cc2)cc1] |

TABLE 1-continued

Representative Compounds

| No. | Structure |
|---|---|
| 9 | 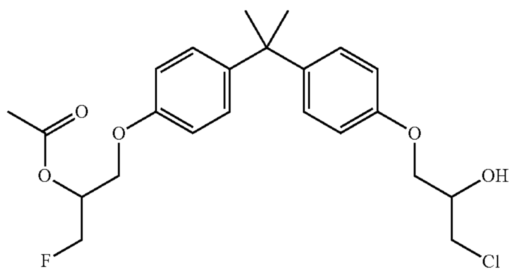 [SMILES: CC(=O)OC(CF)COc1ccc(C(C)(C)c2ccc(OCC(O)CCl)cc2)cc1] |
| 9a | 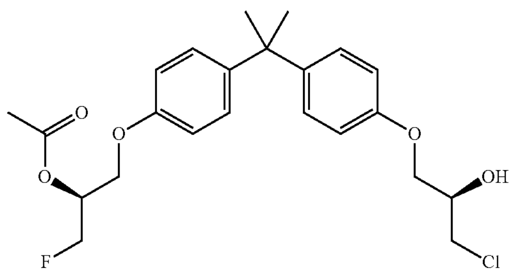 |
| 9b | 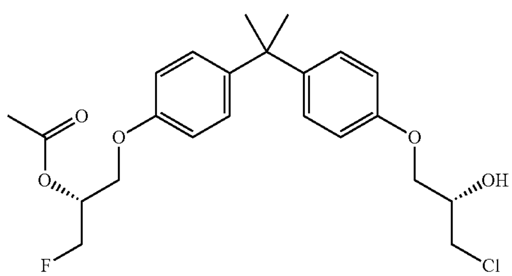 [SMILES: CC(=O)O[C@@H](CF)COc1ccc(C(C)(C)c2ccc(OC[C@H](O)CCl)cc2)cc1] |
| 9c | 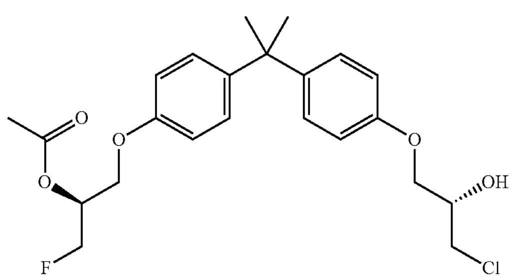 [SMILES: CC(=O)O[C@H](CF)COc1ccc(C(C)(C)c2ccc(OC[C@H](O)CCl)cc2)cc1] |
| 9d | 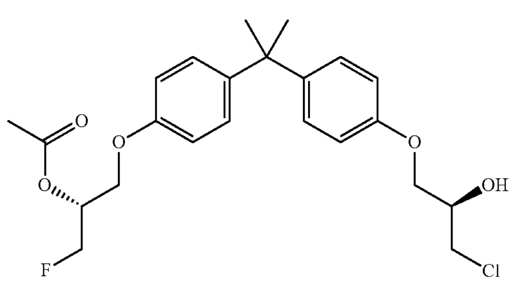 [SMILES: CC(=O)O[C@@H](CF)COc1ccc(C(C)(C)c2ccc(OC[C@@H](O)CCl)cc2)cc1] |

TABLE 1-continued

| Representative Compounds | |
|---|---|
| No. | Structure |

10

10a

10b

10c

10d

TABLE 1-continued

Representative Compounds

| No. | Structure |
|---|---|
| 11 | 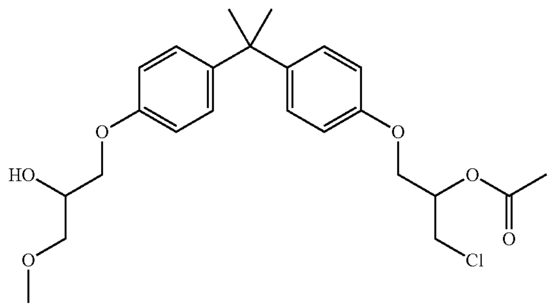 [SMILES: COCC(O)COc1ccc(C(C)(C)c2ccc(OCC(CCl)OC(C)=O)cc2)cc1] |
| 11a | 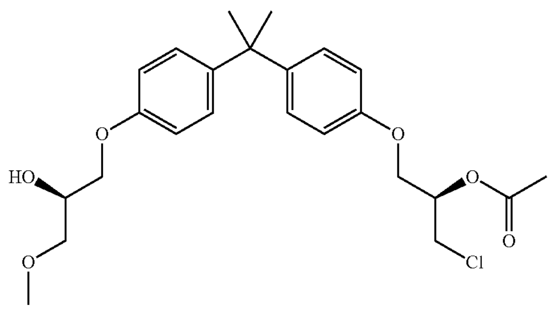 [SMILES: COC[C@@H](O)COc1ccc(C(C)(C)c2ccc(OC[C@H](CCl)OC(C)=O)cc2)cc1] |
| 11b | 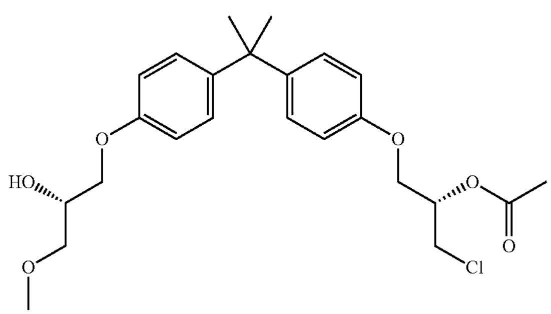 [SMILES: COC[C@H](O)COc1ccc(C(C)(C)c2ccc(OC[C@@H](CCl)OC(C)=O)cc2)cc1] |
| 11c | 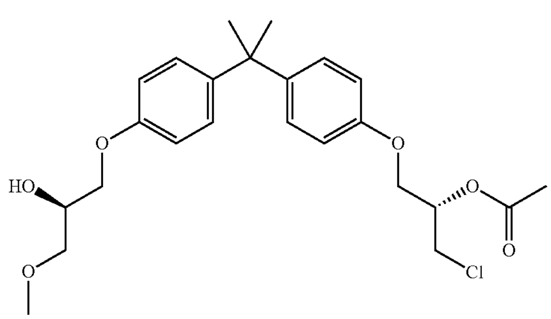 [SMILES: COC[C@@H](O)COc1ccc(C(C)(C)c2ccc(OC[C@@H](CCl)OC(C)=O)cc2)cc1] |

TABLE 1-continued

Representative Compounds

| No. | Structure |
|---|---|
| 11d | 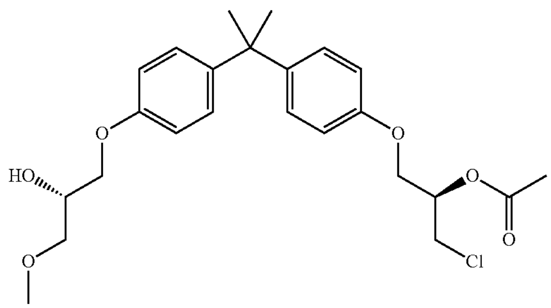 [SMILES: COC[C@H](O)COc1ccc(C(C)(C)c2ccc(OC[C@H](CCl)OC(C)=O)cc2)cc1] |
| 12 | 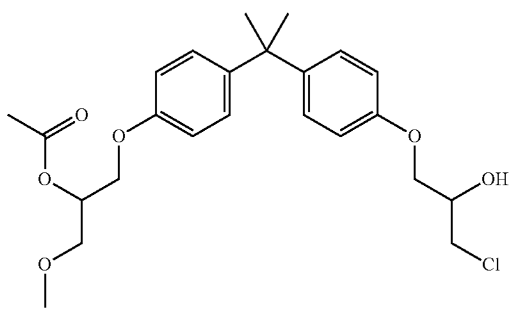 [SMILES: COCC(COc1ccc(C(C)(C)c2ccc(OCC(O)CCl)cc2)cc1)OC(C)=O] |
| 12a | 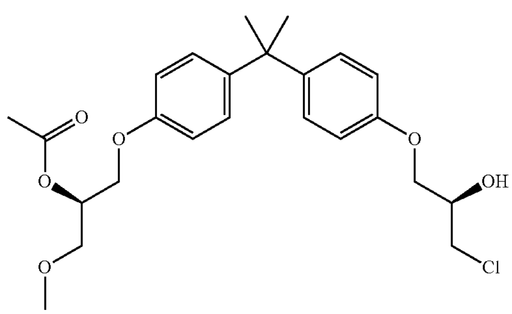 [SMILES: COC[C@H](COc1ccc(C(C)(C)c2ccc(OC[C@@H](O)CCl)cc2)cc1)OC(C)=O] |
| 12b | 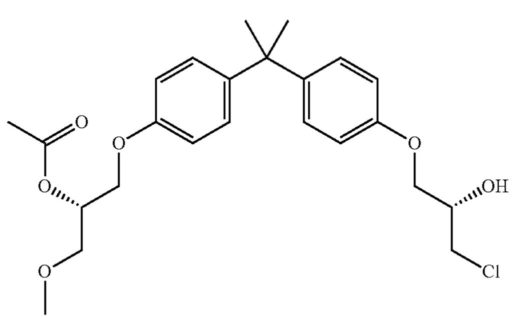 [SMILES: COC[C@@H](COc1ccc(C(C)(C)c2ccc(OC[C@H](O)CCl)cc2)cc1)OC(C)=O] |

TABLE 1-continued
Representative Compounds
| No. | Structure |
|---|---|
| 12c | 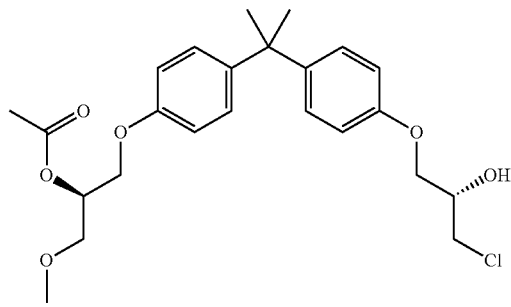 [SMILES: COC[C@H](COc1ccc(C(C)(C)c2ccc(OC[C@H](O)CCl)cc2)cc1)OC(C)=O] |
| 12d | 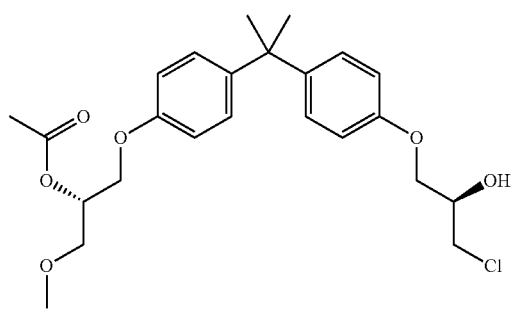 [SMILES: COC[C@@H](COc1ccc(C(C)(C)c2ccc(OC[C@@H](O)CCl)cc2)cc1)OC(C)=O] |
| 13 | 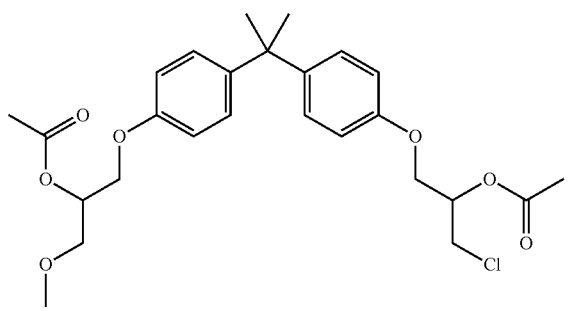 [SMILES: COCC(COc1ccc(C(C)(C)c2ccc(OCC(CCl)OC(C)=O)cc2)cc1)OC(C)=O] |
| 13a | 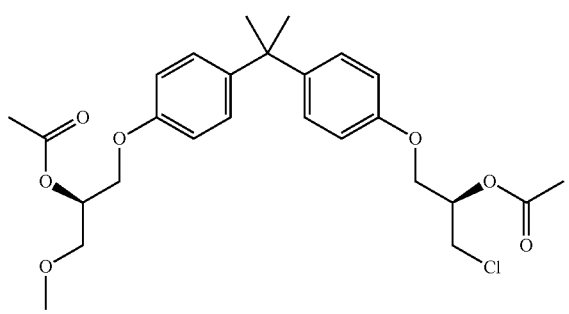 [SMILES: COC[C@H](COc1ccc(C(C)(C)c2ccc(OC[C@H](CCl)OC(C)=O)cc2)cc1)OC(C)=O] |

TABLE 1-continued
Representative Compounds
| No. | Structure |
|---|---|
| 13b | 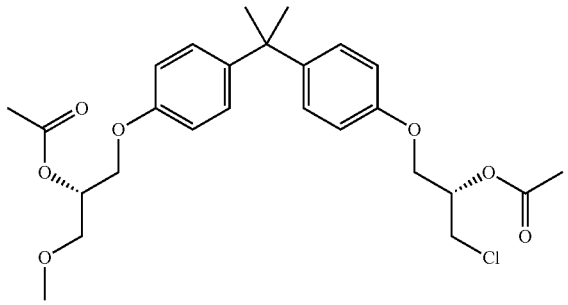 [SMILES: COC[C@@H](COc1ccc(C(C)(C)c2ccc(OC[C@@H](CCl)OC(C)=O)cc2)cc1)OC(C)=O] |
| 13c | 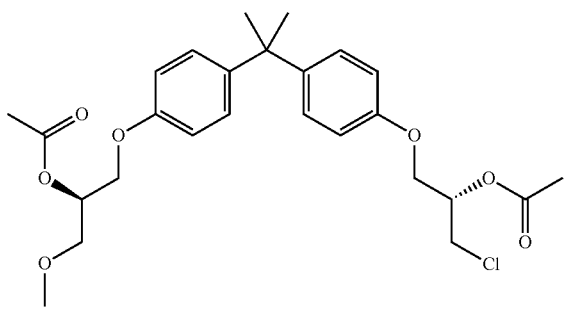 [SMILES: COC[C@H](COc1ccc(C(C)(C)c2ccc(OC[C@@H](CCl)OC(C)=O)cc2)cc1)OC(C)=O] |
| 13d | 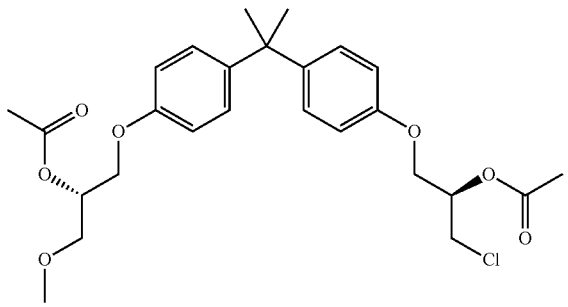 [SMILES: COC[C@@H](COc1ccc(C(C)(C)c2ccc(OC[C@H](CCl)OC(C)=O)cc2)cc1)OC(C)=O] |
| N/A | N/A |

In other particular embodiments of the compounds, as described anywhere herein, the following compounds in Table 2 are provided.

TABLE 2

Representative Compounds

Structure

TABLE 2-continued

Representative Compounds Structure

[Chemical structure: Bisphenol A derivative with one arm bearing -OCH2-CH(OH)-CH2-OMe and the other arm bearing -OCH2-CH(OH)-CH2-Cl]

[Chemical structure: Bisphenol A derivative with one arm bearing -OCH2-CH(OC(O)Et)-CH2-OMe and the other arm bearing -OCH2-CH(OC(O)Et)-CH2-Cl]

In other particular embodiments of the compounds, as described anywhere herein, the following compounds in Table 3 are provided, which have positions 1, 2, and 20 numbered for the majority of compounds.

TABLE 3

Representative Compounds Structure

[Chemical structure: Bisphenol A derivative with one arm bearing AcO-CH2(1)-CH(OH)(2)-CH2-O- and the other arm bearing -O-CH2-CH(OH)(20)-CH2-Cl]

[Chemical structure: Bisphenol A derivative with one arm bearing HO-CH2(1)-CH(OAc)(2)-CH2-O- and the other arm bearing -O-CH2-CH(OH)(20)-CH2-Cl]

TABLE 3-continued

Representative Compounds Structure

[Chemical structure: Bisphenol A derivative with one arm bearing HO-CH2(1)-CH(OH)(2)-CH2-O- and the other arm bearing -O-CH2-CH(OAc)(20)-CH2-Cl]

[Chemical structure: Bisphenol A derivative with one arm bearing AcO-CH2(1)-CH(OAc)(2)-CH2-O- and the other arm bearing -O-CH2-CH(OH)(20)-CH2-Cl]

TABLE 3-continued

Representative Compounds Structure

[Chemical structures of BPA-derived compounds with OAc, OH, Cl, and F substituents]

Compounds as described herein may be in the free form or in the form of a salt thereof. In some embodiments, compounds as described herein may be in the form of a pharmaceutically acceptable salt, which are known in the art (Berge et al., J. Pharm. Sci. 1977, 66, 1). Pharmaceutically acceptable salt as used herein includes, for example, salts that have the desired pharmacological activity of the parent compound (salts which retain the biological effectiveness and/or properties of the parent compound and which are not biologically and/or otherwise undesirable). Compounds as described herein having one or more functional groups capable of forming a salt may be, for example, formed as a pharmaceutically acceptable salt. Compounds containing one or more basic functional groups may be capable of forming a pharmaceutically acceptable salt with, for example, a pharmaceutically acceptable organic or inorganic acid. Pharmaceutically acceptable salts may be derived from, for example, and without limitation, acetic acid, adipic acid, alginic acid, aspartic acid, ascorbic acid, benzoic acid, benzenesulfonic acid, butyric acid, cinnamic acid, citric acid, camphoric acid, camphorsulfonic acid, cyclopentanepropionic acid, diethylacetic acid, digluconic acid, dodecylsulfonic acid, ethanesulfonic acid, formic acid, fumaric acid, glucoheptanoic acid, gluconic acid, glycerophosphoric acid, glycolic acid, hemisulfonic acid, heptanoic acid, hexanoic acid, hydrochloric acid, hydrobromic acid, hydriodic acid, 2-hydroxyethanesulfonic acid, isonicotinic acid, lactic acid, malic acid, maleic acid, malonic acid, mandelic acid, methanesulfonic acid, 2-naphtalenesulfonic acid, naphthalenedisulphonic acid, p-toluenesulfonic acid, nicotinic acid, nitric acid, oxalic acid, pamoic acid, pectinic acid, 3-phenylpropionic acid, phosphoric acid, picric acid, pimelic acid, pivalic acid, propionic acid, pyruvic acid, salicylic acid, succinic acid, sulfuric acid, sulfamic acid, tartaric acid, thiocyanic acid or undecanoic acid. Compounds containing one or more acidic functional groups may be capable of forming pharmaceutically acceptable salts with a pharmaceutically acceptable base, for example, and without limitation, inorganic bases based on alkaline metals or alkaline earth metals or organic bases such as primary amine compounds, secondary amine compounds, tertiary amine compounds, quaternary amine compounds, substituted amines, naturally occurring substituted amines, cyclic amines or basic ion-exchange resins. Pharmaceutically acceptable salts may be derived from, for example, and without limitation, a hydroxide, carbonate, or bicarbonate of a pharmaceutically acceptable metal cation such as ammonium, sodium, potassium, lithium, calcium, magnesium, iron, zinc, copper, manganese or aluminum, ammonia, benzathine, meglumine, methylamine, dimethylamine, trimethylamine, ethylamine, diethylamine, triethylamine, isopropylamine, tripropylamine, tributylamine, ethanolamine, diethanolamine, 2-dimethylaminoethanol, 2-diethylaminoethanol, dicyclohexylamine, lysine, arginine, histidine, caffeine, hydrabamine, choline, betaine, ethylenediamine, glucosamine, glucamine, methylglucamine, theobromine, purines, piperazine, piperidine, procaine, N-ethylpiperidine, theobromine, tetramethylammonium compounds, tetraethylammonium compounds, pyridine, N,N-dimethylaniline, N-methylpiperidine, morpholine, N-methylmorpholine, N-ethylmorpholine, dicyclohexylamine, dibenzylamine, N,N-dibenzylphenethylamine, 1-ephenamine, N,N'-dibenzylethylenediamine or polyamine resins. In some embodiments, compounds as described herein may contain both acidic and basic groups and may be in the form of inner salts or zwitterions, for example, and without limitation, betaines. Salts as described herein may be prepared by conventional processes known to a person skilled in the art, for example, and without limitation, by reacting the free form with an organic acid or inorganic acid or base, or by anion exchange or cation exchange from other salts. Those skilled in the art will appreciate that preparation of salts may occur in situ during isolation and purification of the compounds or preparation of salts may occur by separately reacting an isolated and purified compound.

In some embodiments, compounds and all different forms thereof (e.g. free forms, salts, polymorphs, isomeric forms) as described herein may be in the solvent addition form, for example, solvates. Solvates contain either stoichiometric or non-stoichiometric amounts of a solvent in physical association the compound or salt thereof. The solvent may be, for example, and without limitation, a pharmaceutically acceptable solvent. For example, hydrates are formed when the solvent is water or alcoholates are formed when the solvent is an alcohol.

In some embodiments, compounds and all different forms thereof (e.g. free forms, salts, solvates, isomeric forms) as described herein may include crystalline and amorphous forms, for example, polymorphs, pseudopolymorphs, conformational polymorphs, amorphous forms, or a combination thereof. Polymorphs include different crystal packing arrangements of the same elemental composition of a compound. Polymorphs usually have different X-ray diffraction patterns, infrared spectra, melting points, density, hardness, crystal shape, optical and electrical properties, stability and/or solubility. Those skilled in the art will appreciate that various factors including recrystallization solvent, rate of crystallization and storage temperature may cause a single crystal form to dominate.

In some embodiments, compounds and all different forms thereof (e.g. free forms, salts, solvates, polymorphs) as described herein include isomers such as geometrical isomers, optical isomers based on asymmetric carbon, stereoisomers, tautomers, individual enantiomers, individual diastereomers, racemates, diastereomeric mixtures and combinations thereof, and are not limited by the description of the Structure illustrated for the sake of convenience.

The present disclosure also provides a pharmaceutical composition comprising any one or more of the compounds (e.g., compounds of structure I) disclosed herein and a pharmaceutically acceptable carrier. In some embodiments, the pharmaceutical composition may be for treating one or more of the following: prostate cancer, breast cancer, ovarian cancer, endometrial cancer, salivary gland carcinoma, hair loss, acne, hirsutism, ovarian cysts, polycystic ovary disease, precocious puberty, spinal and bulbar muscular atrophy, and age-related macular degeneration.

In some embodiments, pharmaceutical compositions in accordance with this disclosure may comprise a compound of Structure I, or a salt of such a compound, preferably a pharmaceutically or physiologically acceptable salt and a pharmaceutically acceptable carrier. Pharmaceutical preparations will typically comprise one or more carriers, excipients or diluents acceptable for the mode of administration of the preparation, be it by injection, inhalation, topical administration, lavage, or other modes suitable for the selected treatment.

Suitable carriers, excipients or diluents are those known in the art for use in such modes of administration.

Suitable pharmaceutical compositions may be formulated by means known in the art and their mode of administration and dose determined by the skilled practitioner. For parenteral administration, a compound may be dissolved in sterile water or saline or a pharmaceutically acceptable vehicle used for administration of non-water soluble compounds such as those used for vitamin K. For enteral administration, the compound may be administered in a tablet, capsule or dissolved in liquid form. The tablet or capsule may be enteric coated, or in a formulation for sustained release. Many suitable formulations are known, including, polymeric or protein microparticles encapsulating a compound to be released, ointments, pastes, gels, hydrogels, or solutions which can be used topically or locally to administer a compound. A sustained release patch or implant may be employed to provide release over a prolonged period of time. Many techniques known to one of skill in the art are described in *Remington: the Science & Practice of Pharmacy by Alfonso Gennaro*, 20$^{th}$ ed., Lippencott Williams & Wilkins, (2000). Formulations for parenteral administration may, for example, contain excipients, polyalkylene glycols such as polyethylene glycol, oils of vegetable origin, or hydrogenated naphthalenes. Biocompatible, biodegradable lactide polymer, lactide/glycolide copolymer, or polyoxyethylene-polyoxypropylene copolymers may be used to control the release of the compounds. Other potentially useful parenteral delivery systems for modulatory compounds include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

Compounds for use in the present disclosure may be obtained from medical sources or modified using known methodologies from naturally occurring compounds. In addition, methods of preparing or synthesizing compounds of the present disclosure will be understood by a person of skill in the art having reference to known chemical synthesis principles, for example the synthetic procedures set forth in PCT Pub. Nos. WO 2010/000066; WO 2011/082487, WO 2011/082488, WO 2012/145330, WO 2012/139039, WO 2012/145328 in co-pending PCT Application No. US 2012/051481 and in co-pending U.S. application Ser. No. 13/863,849 and 61/667,355, which applications are herby incorporated by reference in their entireties for all purposes. Auzou et al 1974 *European Journal of Medicinal Chemistry* 9(5), 548-554 also describes suitable synthetic procedures that may be considered and suitably adapted for preparing compounds of Structure I as set out above. Other references that may be helpful include: Debasish Das, Jyh-Fu Lee and Soofin Cheng "Sulfonic acid functionalized mesoporous MCM-41 silica as a convenient catalyst for Bisphenol-A synthesis" *Chemical Communications*, (2001) 2178-2179; U.S. Pat. No. 2,571,217 Davis, Orris L.; Knight, Horace S.; Skinner, John R. (Shell Development Co.) "Halohydrin ethers of phenols." (1951); and Rokicki, G.; Pawlicki, J.; Kuran, W. "Reactions of 4-chloromethyl-1,3-dioxolan-2-one with phenols as a new route to polyols and cyclic carbonates." Journal fuer Praktische Chemie (Leipzig) (1985) 327, 718-722. Each of the above references are hereby incorporated by reference in their entirety for all purposes.

For example, certain embodiments of the compounds of the present disclosure may be prepared with reference to the following General Reaction Scheme I:

appropriate anhydride (e.g. acetic anhydride and the like) and deprotection of the ketal. Triester compounds of structure I can be prepared by treatment of compound D with an appropriate anhydride. Finally, the 1,2-dihydroxyls can both be converted to a desired ester group using a modification of the above scheme as demonstrated in Examples 9-11. Other compounds of structure I are easily prepared by one of ordinary skill in the art based on the above description.

General Reaction Scheme I

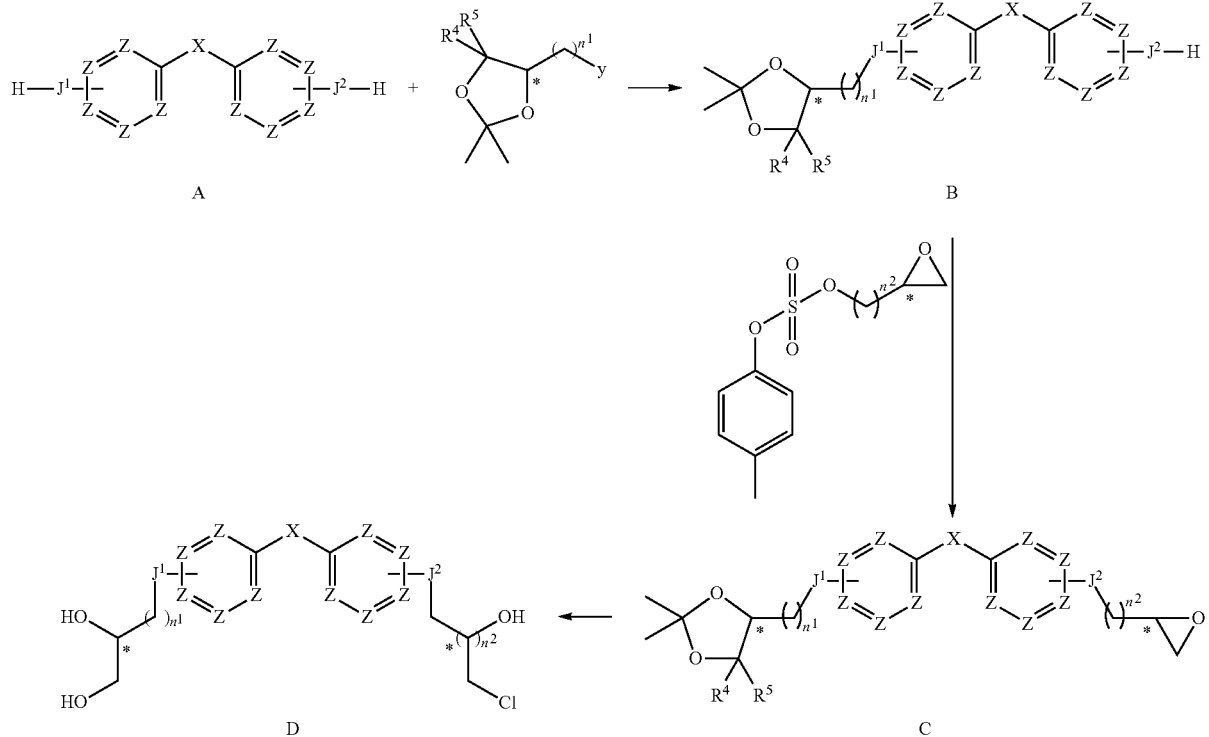

Compounds of structure I can be prepared in reference to General Reaction Scheme 1, wherein $R^3$, $R^4$, $J^1$, $J^2$, $n^1$, $n^2$ and x are as defined for structure I, y is a leaving group, such as chloro, and * indicates a stereocenter. Compounds of structure A, can be purchased from commercial sources or prepared according to methods known in the art. Reaction of A with an appropriately substituted 1,3-dioxolane yields compounds of structure B. Optically pure or racemic dioxolanes may be employed to yield the desired stereochemistry. Epoxidation of B with an appropriate reagent, for example an appropriately substituted glycidyl tosylate, results in compounds of structure C. Various epoxidation reagents may be employed, including optically pure reagents which yield optically pure epoxides (e.g., + or − glycidyl tosylate). Treatment of C with an appropriate ring-opening reagent, for example $CeCl_3 \times 7H_2O$, yields D.

Compounds of structure D, can be used as intermediates for the preparation of various compounds of Structure I. For example, compound D can be modified to include an ester at the primary alcohol by treatment with the appropriate acid chloride (e.g., acetyl chloride and the like). Alternatively, the 1,2-dihydroxyl moiety can be protected as a ketal by reaction with 2,2-dimethoxypropane, followed by conversion of the free secondary alcohol to an ester by treatment with the Compounds of structure I, wherein $R^3$ is halo can be easily prepared by modifications to the above scheme. For example, treatment of D with an appropriate halogenating reagent, followed by esterification as described above, yields compounds of structure I wherein $R^3$ is halo (e.g., fluoro). For example, in one embodiment a fluorine atom is introduced by treatment with diethylaminosulfurtrifluoride (DAST) or Xtalfluor-E or M (see *J. Org. Chem.* 2010, 75, 3401-3411, which is hereby incorporated by reference in its entirety). In other embodiments, the primary hydroxyl moiety in D may be converted to an appropriate leaving group, for example by reaction with tosyl chloride or mesyl anhydride, followed by reaction with [$K^+$/2,2,2-cryptand]$F^-$ or tetrabutylammonium fluoride. Other methods for fluorination of D are known to those of skill in the art. For descriptions of fluorination procedures see *J. Org. Chem.* 2010, 75, 3401-3411, *Bioorg. Med. Chem.* 2009, 17, 7441-7448, and *J. Med. Chem.* 1990, 33, 2430-2437, each of which is hereby incorporated by reference in its entirety. Compounds of structure I wherein $R^3$ is —$OR^{12}$ can be prepared by treating compounds of structure A with 2 equivalents of an appropriate epoxidation reagent, for example an appropriately substituted glycidyl tosylate, to yield a bis epoxide. One of these epoxides can be opened with an alcohol (i.e., $R^3OH$), followed by opening of the remaining epoxide with $CeCl_3 \times 7H_2O$ and esterification as described above to yield the compound of structure I.

General Reaction Scheme II

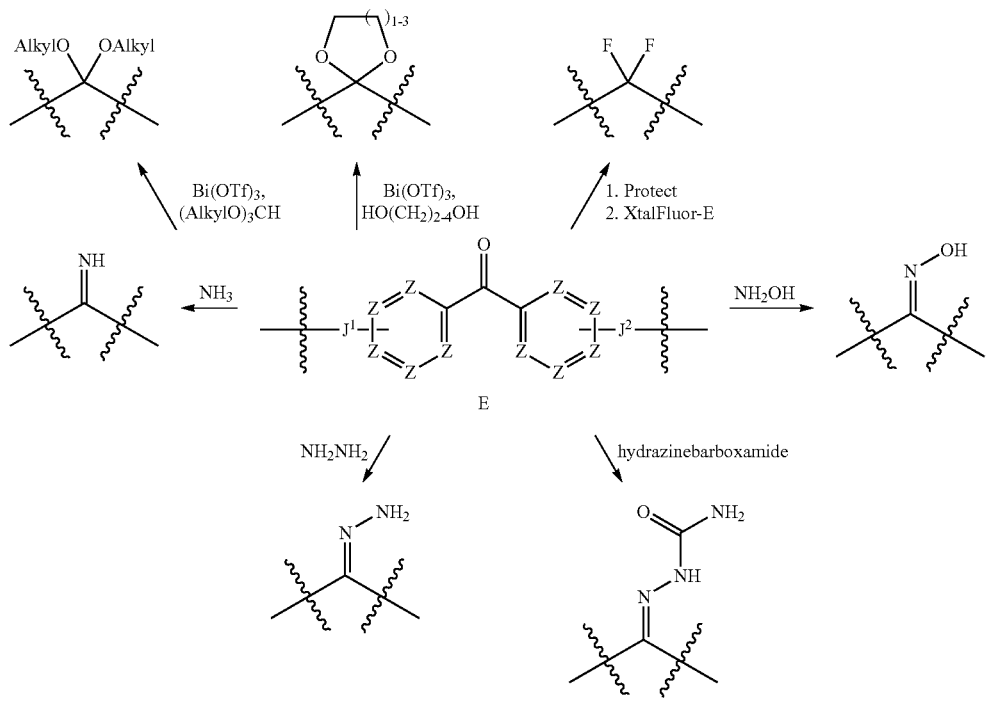

Compounds of structure I having various bridging groups (i.e., "X") can be prepared according to General Reaction Scheme II. Compounds of structure E can be used to prepare any number of various compounds of structure I. Methods for the reactions illustrated in General Reaction Scheme II are well known in the art. Any of the functional groups depicted in General Reaction Scheme II can be further functionalized using techniques and methods well-known to one of ordinary skill in the art.

One skilled in the art will recognize that variations to the order of the steps and reagents discussed in reference to the above synthetic schemes are possible. Furthermore, an appropriate protecting group strategy, such as those described in, *Greene's Protective Groups in Organic Synthesis*, 4$^{th}$ Ed., Peter G. M. Wuts and Theodora W. Greene, John Wiley and Sons, Inc., 2007, which is hereby incorporated by reference in its entirety, may also be employed. In addition, compounds of structure I having various substitutions (e.g., different values for $R^1$, $R^2$, $R^3$, $R^4$, $J^1$, $J^2$, etc.) and different positional isomers can be prepared by modifications to the above starting materials and/or procedures. Such modifications are well within the ability of one of ordinary skill in the art.

III. Methods

The present compounds find use in any number of methods. For example, in some embodiments the compounds are useful in methods for modulating androgen receptors.

Accordingly, in one embodiment, the present disclosure provides the use of a composition comprising any one of the foregoing compounds of Structure (I) for modulating androgen receptor (AR) activity. For example in some embodiments, modulating androgen receptor (AR) activity is in a mammalian cell. Modulating androgen receptor may be in a subject in need thereof (e.g., a mammalian subject) and for treatment of any of the described conditions or diseases.

In other embodiments, modulating androgen receptor (AR) activity is for treatment of at least one indication selected from the group consisting of: prostate cancer, breast cancer, ovarian cancer, endometrial cancer, salivary gland carcinoma, hair loss, acne, hirsutism, ovarian cysts, polycystic ovary disease, precocious puberty, spinal and bulbar muscular atrophy, and age-related macular degeneration. For example in some embodiments, the indication is prostate cancer. In other embodiments, the prostate cancer is castration resistant prostate cancer (also referred to as hormone refractory, androgen-independent, androgen deprivation resistant, androgen ablation resistant, androgen depletion-independent, castration-recurrent, anti-androgen-recurrent). While in other embodiments, the prostate cancer is androgen-dependent prostate cancer.

In other embodiments, the present disclosure provides a method of modulating androgen receptor (AR) activity, the method comprising administering a composition comprising any one of the foregoing compounds of Structure (I), or pharmaceutically acceptable salt, stereoisomer or tautomer thereof to a subject (e.g., mammal) in need thereof.

In other further embodiments of the foregoing method, modulating androgen receptor (AR) activity is for the treatment of one or more of the following: prostate cancer, breast cancer, ovarian cancer, endometrial cancer, salivary gland carcinoma, hair loss, acne, hirsutism, ovarian cysts, polycystic ovary disease, precocious puberty, spinal and bulbar muscular atrophy, and age-related macular degeneration. For example in some embodiments, the prostate cancer is castration resistant prostate cancer (also referred to as hormone refractory, androgen-independent, androgen deprivation resistant, androgen ablation resistant, androgen depletion-independent, castration-recurrent, anti-androgen-recurrent). In other embodiments, the prostate cancer is androgen-dependent prostate cancer.

In accordance with another embodiment, there is provided a use of the compounds of Structure (I) as described anywhere herein for preparation of a medicament for modulating androgen receptor (AR).

In other embodiments, the present disclosure provides a method for increasing the bioavailability (e.g., oral bioavailability) of a hydroxyl-containing androgen receptor modulator, the method comprising replacing at least one hydroxyl moiety with an alkyl (e.g., methyl), alkenyl, aryl or aralkyl ester.

In accordance with a further embodiment, there is provided a method of screening for androgen receptor modulating compounds, wherein the compounds screened are selected from the compounds as described anywhere herein.

The modulating of the androgen receptor (AR) activity may be in a mammalian cell. The modulating of the androgen receptor (AR) activity may be in a mammal. The mammal may be a human.

Alternatively, the administering may be to a mammal. The administering may be to a mammal in need thereof and in an effective amount for the treatment of at least one indication selected from the group consisting of: prostate cancer, breast cancer, ovarian cancer, endometrial cancer, salivary gland carcinoma, hair loss, acne, hirsutism, ovarian cysts, polycystic ovary disease, precocious puberty, spinal and bulbar muscular atrophy (e.g., Kennedy's disease), and age-related macular degeneration.

The mammalian cell may be a human cell. The modulating androgen receptor activity may be for inhibiting androgen receptor N-terminal domain activity. The modulating androgen receptor activity may be for inhibiting androgen receptor activity. The modulating may be in vivo. The modulating androgen receptor activity may be for treatment of at least one indication selected from the group consisting of: prostate cancer, breast cancer, ovarian cancer, endometrial cancer, salivary gland carcinoma, hair loss, acne, hirsutism, ovarian cysts, polycystic ovary disease, precocious puberty, spinal and bulbar muscular atrophy (e.g., Kennedy's disease), and age-related macular degeneration. The indication may be prostate cancer. The prostate cancer may be castration-resistant prostate cancer. The prostate cancer may be androgen-dependent prostate cancer.

In some embodiments, compounds and all different forms thereof as described herein may be used, for example, and without limitation, in combination with other treatment methods for at least one indication selected from the group consisting of: prostate cancer, breast cancer, ovarian cancer, endometrial cancer, salivary gland carcinoma, hair loss, acne, hirsutism, ovarian cysts, polycystic ovary disease, precocious puberty, spinal and bulbar muscular atrophy, and age-related macular degeneration. For example, compounds and all their different forms as described herein may be used as neoadjuvant (prior), adjunctive (during), and/or adjuvant (after) therapy with surgery, radiation (brachytherapy or external beam), or other therapies (e.g., HIFU), and in combination with chemotherapies, androgen ablation, antiandrogens or any other therapeutic approach.

With respect to combination therapies, one embodiment of the present disclosure provides a combination of any one or more of a compound of Structure I with one or more currently-used or experimental pharmacological therapies which are or may be utilized to treat any of the above disease states (e.g., androgen-independent prostate cancer or Kennedy's disease). Methods, uses and pharmaceutical compositions comprising the above combination are also provided.

In some embodiments, the present disclosure is directed to a method for modulating androgen receptor (e.g., for treatment of any of the above conditions) by administering to a subject in need thereof a pharmaceutical composition comprising a compound of structure I and an additional therapeutic agent. Pharmaceutical compositions (and uses thereof) comprising any one of the foregoing compounds of Formula (I), an additional therapeutic agent and a pharmaceutically acceptable carrier are also provided. For example, in some embodiments, the additional therapeutic agent is for treating prostate cancer, breast cancer, ovarian cancer, endometrial cancer, salivary gland carcinoma, hair loss, acne, hirsutism, ovarian cysts, polycystic ovary disease, precocious puberty, spinal and bulbar muscular atrophy or age-related macular degeneration.

The disclosed compounds, which are thought to interfere with the androgen receptor principally through binding to the N-terminus of the androgen receptor, are expected to demonstrate beneficial synergistic therapeutic effects when used in concert with existing approved and in-development agents. That is, the biological impact of using the agents in concert with one another produces a biological and therapeutic effect which is greater than the simple additive effect of each of them separately.

Accordingly, one embodiment comprises the use of the disclosed compounds in combination therapy with one or more currently-used or experimental pharmacological therapies which are utilized for treating the above disease states irrespective of the biological mechanism of action of such pharmacological therapies, including without limitation pharmacological therapies which directly or indirectly inhibit the androgen receptor, pharmacological therapies which are cyto-toxic in nature, and pharmacological therapies which interfere with the biological production or function of androgen (hereinafter, the "Other Therapeutic Agents"). By "combination therapy" is meant the administration of any one or more of a compound of Structure I with one or more of another therapeutic agent to the same patient such that their pharmacological effects are contemporaneous with one another, or if not contemporaneous, that their effects are synergistic with one another even though dosed sequentially rather than contemporaneously.

Such administration includes without limitation dosing of one or more of a compound of Structure I and one or more of the Other Therapeutic Agent(s) as separate agents without any comingling prior to dosing, as well as formulations which include one or more Other Androgen-Blocking Therapeutic Agents mixed with one or more compound of Structure I as a pre-mixed formulation. Administration of the compound(s) of Structure I in combination with Other Therapeutic Agents for treatment of the above disease states also includes dosing by any dosing method including without limitation, intravenous delivery, oral delivery, intra-peritoneal delivery, intra-muscular delivery, or intra-tumoral delivery.

In another aspect of the present disclosure, the one or more of the Other Therapeutic Agent may be administered to the patient before administration of the compound(s) of Structure I. In another embodiment, the compound(s) of Structure I may be co-administered with one or more of the Other Therapeutic Agents. In yet another aspect, the one or more Other Therapeutic Agent may be administered to the patient after administration of the compound(s) of Structure I.

It is fully within the scope of the disclosure that the ratio of the doses of compound(s) of Structure I to that of the one or more Other Therapeutic Agents may or may not equal to one and may be varied accordingly to achieve the optimal therapeutic benefit.

For greater clarity the compound(s) of Structure I that are combined with the one or more Other Therapeutic Agents for improved treatment of the above disease states may comprise, but are not limited to any compound having a structure of Structure I, including those compounds shown in Table 2.

The Other Therapeutic Agents include without limitation any pharmacological agent which is currently approved by the FDA in the U.S. (or elsewhere by any other regulatory body) for use as pharmacological treatment of any of the above disease states, or which is currently being used experimentally as part of a clinical trial program that relates to the above disease states. Non-limiting examples of the Other Pharmacological Agents comprise, without limitation: the chemical entity known as enzalutamide (4-(3-(4-cyano-3-(trifluoromethyl)phenyl)-5,5-dimethyl-4-oxo-2-thioxoimidazolidin-1-yl)-2-fluoro-N-methylbenzamide) and related compounds, which appears to be a blocker of the androgen receptor LBD and is currently in development as a treatment for prostate cancer; the chemical entity known as Galeterone and related compounds which appears to be a blocker of the androgen receptor LBD, and a CYP17 lyase inhibitor, and also appears to decrease overall androgen receptor levels in prostate cancer cells. Galeterone is currently in development as a treatment for prostate cancer; the chemical entity known as ARN-509 and related compounds which appears to be a blocker of the androgen receptor LBD and is currently in development as a treatment for prostate cancer; the chemical entity known as abiraterone (or CB-7630; (3S,8R,9S,10R,13S,14S)-10,13-dimethyl-17-(pyridin-3-yl)2,3,4,7,8,9,10,11,12,13,14,15-dodecahydro-1H-cyclopenta[a]phenanthren-3-ol), and related molecules, which appears to block the production of androgen and is for the treatment of prostate cancer; the chemical entity known as bicalutamide (N-[4-cyano-3-(trifluoromethyl)phenyl]-3-[(4-fluorophenyl)sulfonyl]-2-hydroxy-2-methylpropanamide) and related compounds, which appears to be a blocker of the androgen receptor LBD and which is currently used to treat prostate cancer, the chemical entity known as nilutamide (5,5-dimethyl-3-[4-nitro-3-(trifluoromethyl)phenyl]imidazolidine-2,4-dione) and related compounds, which appears to be a blocker of the AR LBD and which is currently used to treat prostate cancer, the chemical entity known as flutamide (2-methyl-N-[4-nitro-3-(trifluoromethyl)phenyl]-propanamide) and related compounds, which appears to be a blocker of the androgen receptor LBD and which is currently used to treat prostate cancer, the chemical entities know as cyproterone acetate (6-chloro-1β,2β-dihydro-17-hydroxy-3'H-cyclopropa[1,2]pregna-4,6-diene-3,20-dione) and related compounds, which appears to be a blocker of the androgen receptor LBD and which is currently used to treat prostate cancer, the chemical entity known as docetaxel (Taxotere; 1,7β,10β-trihydroxy-9-oxo-5β,20-epoxytax-11-ene-2α,4,13α-triyl 4-acetate 2-benzoate 13-{(2R,3S)-3-[(tert-butoxycarbonyl)amino]-2-hydroxy-3-phenylpropanoate}) and related compounds, which appears to be a cytotoxic antimicrotubule agent and is currently used in combination with prednisone to treat prostate cancer, the chemical entity known as Bevacizumab (Avastin), a monoclonal antibody that recognizes and blocks vascular endothelial growth factor A (VEGF-A) and may be used to treat prostate cancer, the chemical entity known as OSU-EIDAC42 ((S)-(+)-N-hydroxy-4-(3-methyl-2-phenylbutyrylamino)-benzamide), and related compounds, which appears to act as a histone deacetylase inhibitor, and is currently being developed as a treatment for prostate cancer, the chemical entity known as VITAXIN which appears to be a monoclonal antibody against the vascular integrin 9αvβ3 to prevent angiogenesis, and which may be used to treat prostate cancer, the chemical entity known as sunitumib (N-(2-diethylaminoethyl)-5-[(Z)-(5-fluoro-2-oxo-1H-indol-3-ylidene)methyl]-2,4-dimethyl-1H-pyrrole-3-carboxamide) and related compounds, which appears to inhibit multiple receptor tyrosine kinases (RTKs) and may be used for treatment of prostate cancer, the chemical entity known as ZD-4054 (N-(3-Methoxy-5-methylpyrazin-2-yl)-2-[4-(1,3,4-oxadiazol-2-yl)phenyl]pyridin-3-sulfonamide) and related compounds, which appears to block the edta receptor and which may be used for treatment of prostate cancer; the chemical entity known as Cabazitaxel (XRP-6258), and related compounds, which appears to be a cytotoxic microtubule inhibitor, and which is currently used to treat prostate cancer; the chemical entity known as MDX-010 (Ipilimumab), a fully human monoclonal antibody that binds to and blocks the activity of CTLA-4 which is currently in development as an immunotherapeutic agent for treatment of prostate cancer; the chemical entity known as OGX 427 which appears to target HSP27 as an antisense agent, and which is currently in development for treatment of prostate cancer; the chemical entity known as OGX OH which appears to target clusterin as an antisense agent; the chemical entity known as finasteride (Proscar, Propecia; N-(1,1-dimethylethyl)-3-oxo-(5α,17β)-4-azaandrost-1-ene-17-carboxamide), and related compounds, which appears to be a 5-alpha reductase inhibitor that reduces levels of dihydrotestosterone, and may be used to treat prostate cancer; the chemical entity known as dutasteride (Avodart; 5α, 17β)-N-{2,5 bis(trifluoromethyl)phenyl}-3-oxo-4-azaandrost-1-ene-17-carboxamide) and related molecules, which appears to be a 5-alpha reductase inhibitor that reduces levels of dihydrotestosterone, and may be used in the treatment of prostate cancer; the chemical entity known as turosteride ((4aR,4bS,6aS,7S,9aS,9bS,11aR)-1,4-a,6a-trimethyl-2-oxo-N-(propan-2-yl)-N-(propan-2-ylcarbamoyl)hexadecahydro-1H-indeno[5,4-f]quinoline-7-carboxamide), and related molecules, which appears to be a 5-alpha reductase inhibitor that reduces levels of dihydrotestosterone and may be used in the treatment of prostate cancer; the chemical entity known as bexlosteride (LY-191,704; (4aS,10bR)-8-chloro-4-methyl-1,2,4a,5,6,10b-hexahydrobenzo[f]quinolin-3-one), and related compounds, which appears to be a 5-alpha reductase inhibitor that reduces levels of dihydrotestosterone and may be used in the treatment of prostate cancer; the chemical entity known as izonsteride (LY-320,236; (4aR,10bR)-8-[(4-ethyl-1,3-benzothiazol-2-yl)sulfanyl]-4,10b-dimethyl-1,4,4a,5,6,10b-hexahydrobenzo[f]quinolin-3(2H)-one) and related compounds, which appears to be a 5-alpha reductase inhibitor that reduces levels of dihydrotestosterone and may be used for the treatment of prostate cancer; the chemical entity known as FCE 28260 and related compounds, which appears to be a 5-alpha reductase inhibitor that reduces levels of dihydrotestosterone and may be used for the treatment of prostate cancer; the chemical entity known as SKF105,111, and related compounds, which appears to be a 5-alpha reductase inhibitor that reduces levels of dihydrotestosterone and may be used for treatment of prostate cancer.

Accordingly, in certain embodiments the additional therapeutic agent is enzalutamide, Galeterone; ARN-509; abiraterone, bicalutamide, nilutamide, flutamide, cyproterone acetate, docetaxel, Bevacizumab (Avastin), OSU-HDAC42, VITAXIN, sunitumib, ZD-4054, Cabazitaxel (XRP-6258), MDX-010 (Ipilimumab), OGX 427, OGX 011, finasteride, dutasteride, turosteride, bexlosteride, izonsteride, FCE 28260, SKF105,111, Radium 233, or related compound(s) thereof.

In another embodiment, the present disclosure provides the use of any one of the foregoing pharmaceutical compositions (including compositions comprising a compound of Structure I and an additional therapeutic agent) for modulating androgen receptor (AR) activity. For example in some embodiments, modulating androgen receptor (AR) activity is in a mammalian cell.

In other embodiments, modulating androgen receptor (AR) activity is for treatment of at least one indication selected from the group consisting of: prostate cancer, breast cancer, ovarian cancer, endometrial cancer, salivary gland carcinoma, hair loss, acne, hirsutism, ovarian cysts, polycystic ovary disease, precocious puberty, spinal and bulbar muscular atrophy, and age-related macular degeneration. For example in some embodiments, the indication is prostate cancer. For example, in some embodiments, the prostate cancer is castration resistant prostate cancer, and in other embodiments the prostate cancer is androgen-dependent prostate cancer.

In yet another embodiment, the present disclosure provides a method of modulating androgen receptor (AR) activity, the method comprising administering any one of the foregoing pharmaceutical compositions (including compositions comprising a compound of Structure I and an additional therapeutic agent) to a subject in need thereof. For example in some embodiments, modulating androgen receptor (AR) activity is for the treatment of one or more of the following: prostate cancer, breast cancer, ovarian cancer, endometrial cancer, salivary gland carcinoma, hair loss, acne, hirsutism, ovarian cysts, polycystic ovary disease, precocious puberty, spinal and bulbar muscular atrophy, and age-related macular degeneration. In still other embodiments, the indication is prostate cancer. For example, in some embodiments, the prostate cancer is castration resistant prostate cancer, while in other embodiments, the prostate cancer is androgen-dependent prostate cancer.

In general, compounds of the disclosure should be used without causing substantial toxicity. Toxicity of the compounds of the disclosure can be determined using standard techniques, for example, by testing in cell cultures or experimental animals and determining the therapeutic index, i.e., the ratio between the LD50 (the dose lethal to 50% of the population) and the LD100 (the dose lethal to 100% of the population). In some circumstances however, such as in severe disease conditions, it may be necessary to administer substantial excesses of the compositions. Some compounds of this disclosure may be toxic at some concentrations. Titration studies may be used to determine toxic and non-toxic concentrations. Toxicity may be evaluated by examining a particular compound's or composition's specificity across cell lines using PC3 cells as a negative control that do not express functional AR. Animal studies may be used to provide an indication if the compound has any effects on other tissues. Systemic therapy that targets the AR will not likely cause major problems to other tissues since antiandrogens and androgen insensitivity syndrome are not fatal.

Compounds as described herein may be administered to a subject. As used herein, a "subject" may be a human, non-human primate, mammal, rat, mouse, cow, horse, pig, sheep, goat, dog, cat and the like. The subject may be suspected of having or at risk for having a cancer, such as prostate cancer, breast cancer, ovarian cancer, salivary gland carcinoma, or endometrial cancer, or suspected of having or at risk for having acne, hirsutism, alopecia, benign prostatic hyperplasia, ovarian cysts, polycystic ovary disease, precocious puberty, spinal and bulbar muscular atrophy, or age-related macular degeneration. Diagnostic methods for various cancers, such as prostate cancer, breast cancer, ovarian cancer, salivary gland carcinoma, or endometrial cancer, and diagnostic methods for acne, hirsutism, alopecia, benign prostatic hyperplasia, ovarian cysts, polycystic ovary disease, precocious puberty, spinal and bulbar muscular atrophy, or age-related macular degeneration and the clinical delineation of cancer, such as prostate cancer, breast cancer, ovarian cancer, salivary gland carcinoma, or endometrial cancer, diagnoses and the clinical delineation of acne, hirsutism, alopecia, benign prostatic hyperplasia, ovarian cysts, polycystic ovary disease, precocious puberty, spinal and bulbar muscular atrophy, or age-related macular degeneration are known to those of ordinary skill in the art.

Compounds described herein may also be used in assays and for research purposes. Definitions used include ligand-dependent activation of the androgen receptor (AR) by androgens such as dihydrotestosterone (DHT) or the synthetic androgen (R1881) used for research purposes. Ligand-independent activation of the AR refers to transactivation of the AR in the absence of androgen (ligand) by, for example, stimulation of the cAMP-dependent protein kinase (PKA) pathway with forskolin (FSK). Some compounds and compositions of this disclosure may inhibit both FSK and androgen (e.g. R1881, a synthetic androgen) induction of ARE-luciferase (ARE-luc). Constitutive activity of the AR refers to splice variants lacking the AR ligand-binding domain. Such compounds may block a mechanism that is common to both ligand-dependent and ligand-independent activation of the AR, as well as constitutively active splice variants of the AR that lack ligand-binding domain. This could involve any step in activation of the AR including dissociation of heatshock proteins, essential posttranslational modifications (e.g., acetylation, phosphorylation), nuclear translocation, protein-protein interactions, formation of the transcriptional complex, release of co-repressors, and/or increased degradation. Some compounds and compositions of this disclosure may inhibit ligand-only activity and may interfere with a mechanism specific to ligand-dependent activation (e.g., accessibility of the ligand binding domain (LBD) to androgen). Numerous disorders in addition to prostate cancer involve the androgen axis (e.g., acne, hirsutism, alopecia, benign prostatic hyperplasia) and compounds interfering with this mechanism may be used to treat such conditions. Some compounds and compositions of this disclosure may only inhibit FSK induction and may be specific inhibitors to ligand-independent activation of the AR. These compounds and compositions may interfere with the cascade of events that normally occur with FSK and/or PKA activity or any downstream effects that may play a role on the AR (e.g. FSK increases MAPK activity which has a potent effect on AR activity). Examples may include an inhibitor of cAMP and or PKA or other kinases. Some compounds and compositions of this disclosure may induce basal levels of activity of the AR (no androgen or stimulation of the PKA pathway). Some compounds and compositions of this disclosure may increase induction by R1881 or FSK. Such compounds and compositions may stimulate transcription or transactivation of the AR.

Some compounds and compositions of this disclosure may inhibit activity of the androgen receptor. Interleukin-6 (IL-6) also causes ligand-independent activation of the AR in LNCaP cells and can be used in addition to FSK.

Compounds or pharmaceutical compositions in accordance with this disclosure or for use in this disclosure may be administered by means of a medical device or appliance such as an implant, graft, prosthesis, stent, etc. Also, implants may be devised which are intended to contain and release such compounds or compositions. An example would be an implant made of a polymeric material adapted to release the compound over a period of time.

It is to be noted that dosage values may vary with the severity of the condition to be alleviated. For any particular subject, specific dosage regimens may be adjusted over time according to the individual need and the professional judgment of the person administering or supervising the administration of the compositions. Dosage ranges set forth herein are exemplary only and do not limit the dosage ranges that may be selected by medical practitioners. The amount of active compound(s) in the composition may vary according to factors such as the disease state, age, sex, and weight of the subject. Dosage regimens may be adjusted to provide the optimum therapeutic response. For example, a single bolus may be administered, several divided doses may be administered over time or the dose may be proportionally reduced or increased as indicated by the exigencies of the therapeutic situation. It may be advantageous to formulate parenteral compositions in dosage unit form for ease of administration and uniformity of dosage.

The compounds described herein may be used for in vivo or in vitro research uses (i.e. non-clinical) to investigate the mechanisms of orphan and nuclear receptors (including steroid receptors such as the androgen receptor). Furthermore, these compounds may be used individually or as part of a kit for in vivo or in vitro research to investigate signal transduction pathways and/or the activation of orphan and nuclear receptors using recombinant proteins, cells maintained in culture, and/or animal models.

Various alternative embodiments and examples of the disclosure are described herein. These embodiments and examples are illustrative and should not be construed as limiting the scope of the disclosure. The following examples are provided for purposes of illustration, not limitation.

EXAMPLES

All non-aqueous reactions were performed in flame-dried round bottomed flasks. The flaks were fitted with rubber septa and reactions were conducted under a positive pressure of argon unless otherwise specified. Stainless steel syringes were used to transfer air- and moisture-sensitive liquids. Flash column chromatography was performed as described by Still et al. (Still, W. C.; Kahn, M.; Mitra, A. *J. Org. Chem.* 1978, 43, 2923) using 230-400 mesh silica gel. Thin-layer chromatography was performed using aluminium plates pre-coated with 0.25 mm 230-400 mesh silica gel impregnated with a fluorescent indicator (254 nm). Thin-layer chromatography plates were visualized by exposure to ultraviolet light and a "Seebach" staining solution (700 mL water, 10.5 g Cerium (IV) sulphate tetrahydrate, 15.0 g molybdato phosphoric acid, 17.5 g sulphuric acid) followed by heating (~1 min) with a heating gun (~250° C.). Organic solutions were concentrated on Büchi R-114 rotatory evaporators at reduced pressure (15-30 torr, house vacuum) at 25-40° C.

Commercial regents and solvents were used as received. All solvents used for extraction and chromatography were HPLC grade. Normal-phase Si gel Sep Paks™ were purchased from waters, Inc. Thin-layer chromatography plates were Kieselgel 60F$_{254}$. All synthetic reagents were purchased from Sigma Aldrich and Fisher Scientific Canada.

Proton nuclear magnetic resonance ($^1$H NMR) spectra were recorded at 25° C. using a Bruker 400 with inverse probe and Bruker 400 spectrometers, are reported in parts per million on the δ scale, and are referenced from the residual protium in the NMR solvent (CDCl$_3$: δ 7.24 (CHCl$_3$)). Carbon-13 nuclear magnetic resonance ($^{13}$C NMR) spectra were recorded with a Bruker 400 spectrometer, are reported in parts per million on the δ scale, and are referenced from the carbon resonances of the solvent (CDCl$_3$: δ 77.23). Spectral features are tabulated in the following order: chemical shift (δ, ppm); multiplicity (s=singlet, d=doublet, t=triplet, m=multiplet, br=broad); coupling constant (J, Hz, number of protons).

LNCaP cells were employed for experiments because they are well-differentiated human prostate cancer cells in which ligand-dependent and ligand-independent activation of AR by FSK has been characterized (Nazareth et al 1996 *J. Biol. Chem.* 271, 19900-19907; and Sadar 1999 *J. Biol. Chem.* 274, 7777-7783). LNCaP cells express endogenous AR and secrete prostate-specific antigen (PSA) (Horoszewicz et al 1983 *Cancer Res.* 43, 1809-1818). LNCaP cells can be grown either as monolayers in cell culture or as tumors in the well-characterized xenograft model that progresses to castration-resistant prostate cancer (CRPC) in castrated hosts (Sato et al 1996 *J. Steroid Biochem. Mol. Biol.* 58, 139-146; Gleave et al 1991 *Cancer Res.* 51, 3753-3761; Sato et al 1997 *Cancer Res.* 57, 1584-1589; and Sadar et al 2002 *Mol. Cancer. Ther.* 1(8), 629-637). R1881 (a synthetic androgen) is employed since it is stable and avoids problems associated with the labile physiological ligand dihydrotestosterone (DHT).

One well characterized ARE-driven reporter gene construct that has been used extensively is the PSA (6.1 kb) enhance/promoter which contains several AREs and is highly inducible by androgens as well as by FSK (Ueda et al 2002 A *J. Biol. Chem.* 277, 7076-7085).

Example 1

Synthesis of (S)-4-(2-(4-((2,2-dimethyl-1,3-dioxolan-4-yl)methoxy)phenyl)propan-2-yl)phenol

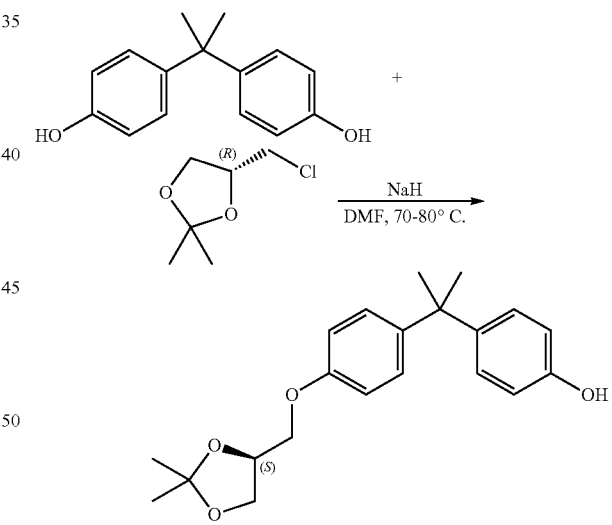

Sodium hydride (60% dispersion in mineral oil, 1750 mg, 43.80 mmol, 1.0 equiv) was added slowly to a stirred solution of Bisphenol A (10000 mg, 43.80 mmol, 1 equiv) in anhydrous dimethyl formamide (30 mL), at room temperature, and the contents were stirred under an atmosphere of argon for 20 min. (R)-(+)-4-chloromethyl-2,2-dimethyl-1,3-dioxolane 98% (7.10 mL, 52.56 mmol, 1.2 equiv) was added via syringe and the mixture was allowed to react at 70-80° C. for 40 h. Then, the reaction was quenched by the addition of a saturated solution of ammonium chloride (10 mL), and the mixture was extracted with ethyl acetate (3×20 mL). The organic layer was washed with deionized water (25 mL), dried over anhydrous magnesium sulfate, filtered and concentrated under reduced pressure. The resulting residue was purified by flash column chromatography on silica gel (eluent: 10% ethyl acetate in hexane) to provide the title compound (3560 mg, 24%, 25-30% conversion) as a foam.

Example 2

Synthesis of (s)-2,2-dimethyl-4-((4-(2-(4-((R)-oxiran-2-ylmethoxy)phenyl)propan-2-yl)phenoxy)methyl)-1,3-dioxolane

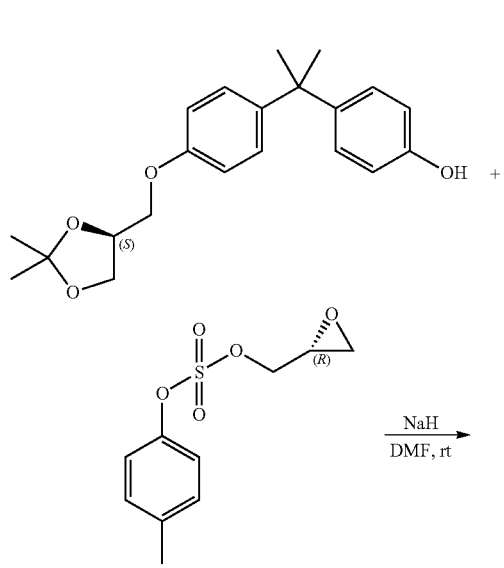

Sodium hydride (60% dispersion in mineral oil, 391 mg, 9.78 mmol, 1.5 equiv) was added slowly to a stirred solution of (S)-4-(2-(4-((2,2-dimethyl-1,3-dioxolan-4-yl)methoxy)phenyl)propan-2-yl)phenol (2230 mg, 6.52 mmol, 1 equiv) in anhydrous dimethyl formamide (15 mL), at room temperature, and the contents were stirred under an atmosphere of argon for 30 min. A solution of (2R)-(−)-glycidyl tosylate 98% (2230 mg, 9.78 mmol, 1.5 equiv) in anhydrous dimethyl formamide (5 mL) was added via syringe and the mixture was allowed to react at room temperature for 16 h. Then, the reaction was quenched by the addition of a saturated solution of ammonium chloride (10 mL), and the mixture was extracted with ethyl acetate (3×20 mL). The organic layer was washed with deionized water (20 mL), dried over anhydrous magnesium sulfate, filtered and concentrated under reduced pressure. The resulting residue was purified by flash column chromatography on silica gel (eluent: 20% to 40% ethyl acetate in hexane) to provide the title compound (2.53 g, 94%) as a clear foam.

Example 3

Synthesis of (R)-3-(4-(2-(4-((S)-3-chloro-2-hydroxypropoxy)phenyl)propan-2-yl)phenoxy)propane-1,2-diol

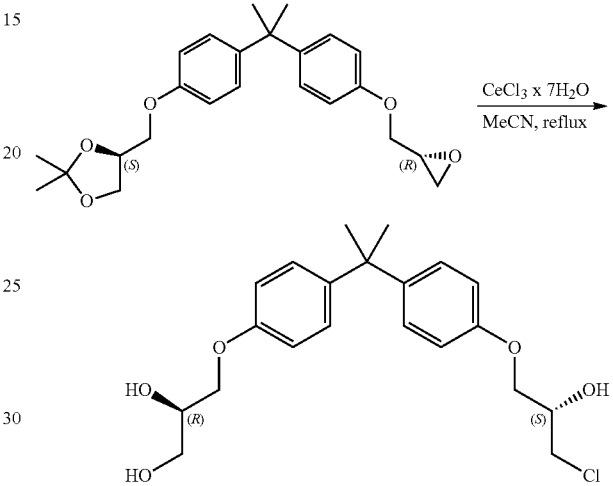

To a solution of (S)-2,2-dimethyl-4-((4-(2-(4-((R)-oxiran-2-ylmethoxy)phenyl)propan-2-yl)phenoxy)methyl)-1,3-dioxolane (2530 mg, 6.34 mmol, 1 equiv) in acetonitrile (25 mL) was added CeCl$_3$.7H$_2$O (5910 mg, 15.87 mmol, 2.5 equiv) and the mixture was refluxed for 20 h. The resulting white paste was filtered and washed with ethyl acetate, and the clear suspension was concentrated under reduced pressure. The resulting residue was purified by flash column chromatography on silica gel (eluent: 20% hexane in ethyl acetate to 100% ethylacetate) and Si gel Sep pak (10 g, eluent: 50% hexane in ethyl acetate to 80% ethylacetate) to provide the title compound (2250 mg, 90%) as a transparent foam.

Example 4

Synthesis of (S)-3-(4-(2-(4-((S)-3-chloro-2-hydroxypropoxy)phenyl)propan-2-yl)phenoxy)-2-hydroxypropyl acetate

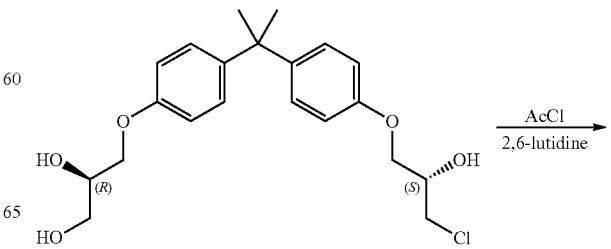

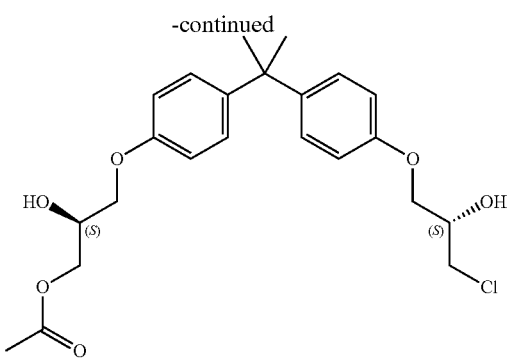

To a solution of (R)-3-(4-(2-(4-((S)-3-chloro-2-hydroxypropoxy)phenyl)propan-2-yl)phenoxy)propane-1,2-diol (1000 mg, 2.53 mmol) in anhydrous dichloromethane (8.0 mL) at −78° C. were successively added 2,6-lutidine (590 μL, 5.06 mmol) and acetic chloride (144 μL, 2.02 mmol) dropwise. After 1 h, the reaction mixture was quenched with an aqueous solution of sodium chloride and stirred for 15 min, and the resulting mixture was extracted twice with dichloromethane. The organic phases were combined, dried over anhydrous magnesium sulfate and filtered. Solvents were evaporated, and the resulting crude material was purified by silica gel flash chromatography (eluent: 2% methanol in dichloromethane) to provide the title compound (300 mg, 27%) as a sticky solid.

Figure 1B:
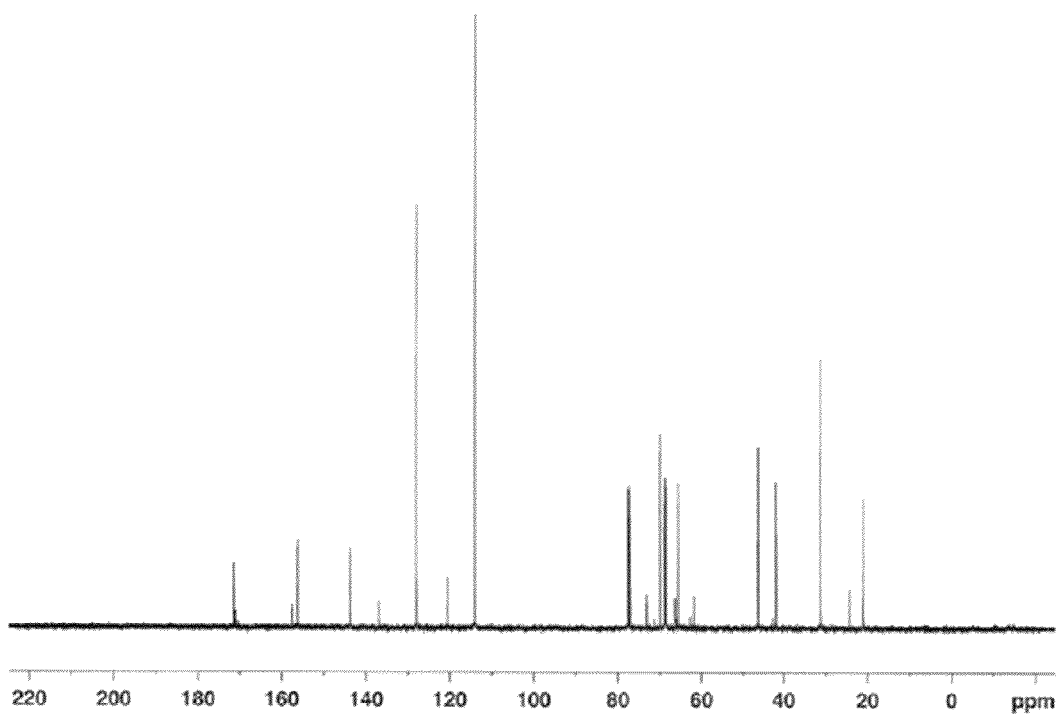
FIG. 1B is a $^{13}$C NMR spectrum for the compound (S)-3-(4-(2-(4-((S)-3-chloro-2-hydroxypropoxy)phenyl)propan-2-yl)phenoxy)-2-hydroxypropyl acetate.
Figure 1C:
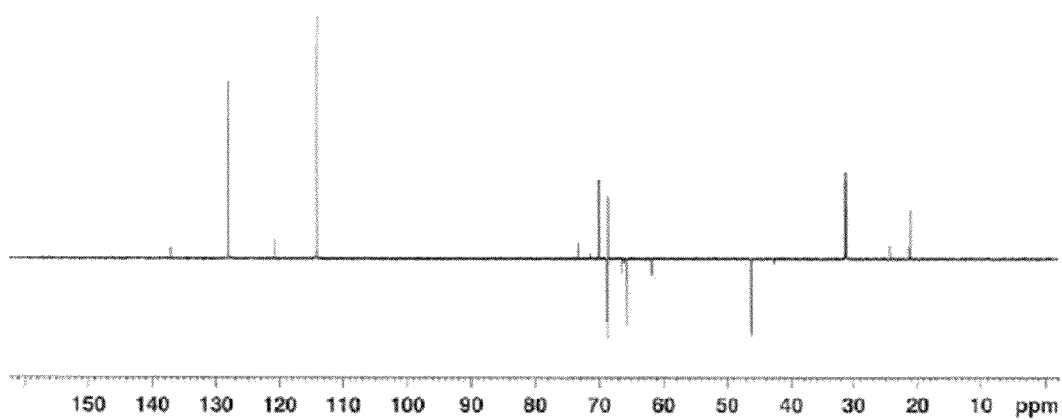
FIG. 1C is a $^{13}$C APT NMR spectrum for the compound (S)-3-(4-(2-(4-((S)-3-chloro-2-hydroxypropoxy)phenyl)propan-2-yl)phenoxy)-2-hydroxypropyl acetate.

FIGS. 1(A)-(C) illustrates $^1$H and $^{13}$C-NMR data for the title compound (S)-3-(4-(2-(4-((S)-3-chloro-2-hydroxypropoxy)phenyl)propan-2-yl)phenoxy)-2-hydroxypropyl acetate.

Example 5

Synthesis of (S)-1-chloro-3-(4-(2-(4-(((S)-2,2-dimethyl-1,3-dioxolan-4-yl)methoxy)phenyl)propan-2-yl)phenoxy)propan-2-ol

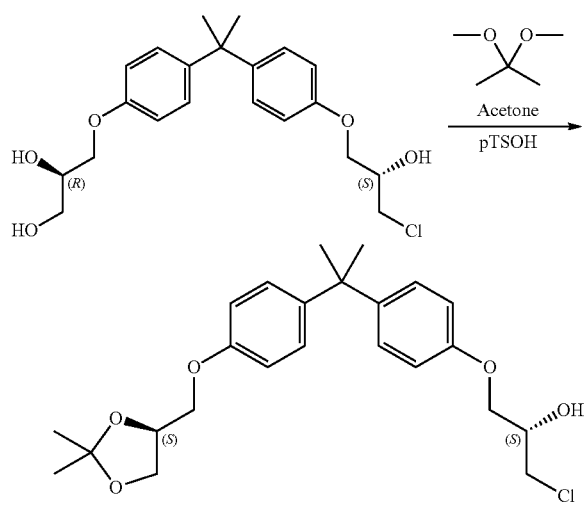

To a solution of (R)-3-(4-(2-(4-((S)-3-chloro-2-hydroxypropoxy)phenyl)propan-2-yl)phenoxy)propane-1,2-diol (1000 mg, 2.53 mmol) in acetone (8.0 mL) was added 2,2-dimethoxypropane (630 μL, 5.06 mmol) and catalytic amounts of p-toluenesulfonic acid. After 14 h, the reaction mixture was quenched with an aqueous solution of sodium chloride and stirred for 15 min, and the resulting mixture was extracted twice with ethyl acetate. The organic phases were combined, dried over anhydrous magnesium sulfate and filtered. Solvents were evaporated, and the resulting crude material was purified by silica gel flash chromatography (eluent: 2% methanol in dichloromethane) to provide the title compound.

Example 6

Synthesis of (S)-1-chloro-3-(4-(2-(4-(((S)-2,2-dimethyl-1,3-dioxolan-4-yl)methoxy)phenyl)propan-2-yl)phenoxy)propan-2-yl acetate

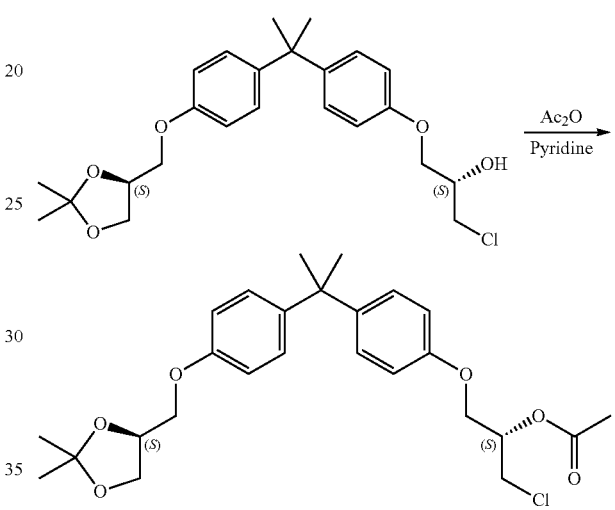

To a solution of (S)-1-chloro-3-(4-(2-(4-(((S)-2,2-dimethyl-1,3-dioxolan-4-yl)methoxy)phenyl)propan-2-yl)phenoxy)propan-2-ol (850 mg, 1.95 mmol) in anhydrous pyridine (6.0 mL) were successively added acetic anhydride (280 μL, 2.93 mmol) and catalytic amount of DMAP. After 3 h, the reaction mixture was quenched with an aqueous solution of sodium chloride and stirred for 15 min, and the resulting mixture was extracted twice with ethyl acetate. The organic phases were combined, dried over anhydrous magnesium sulfate and filtered. Solvents were evaporated, and the resulting crude material was used without further purification.

Example 7

Synthesis of (S)-1-chloro-3-(4-(2-(4-((R)-2,3-dihydroxypropoxy)phenyl)propan-2-yl)phenoxy)propan-2-yl acetate

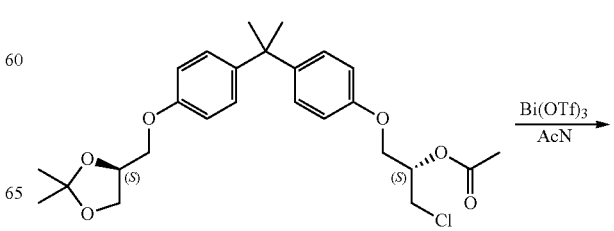

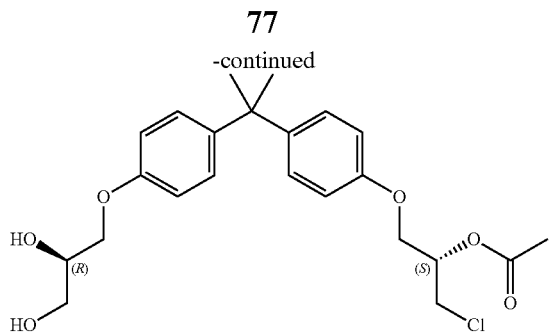

To a solution of crude (S)-1-chloro-3-(4-(2-(4-(((S)-2,2-dimethyl-1,3-dioxolan-4-yl)methoxy)phenyl)propan-2-yl)phenoxy)propan-2-yl acetate in anhydrous acetonitrile (8.0 mL) was added bismuth triflate (300 mg, 0.46 mmol) in one portion. After 0.5 h, the reaction mixture was partitioned twice with sodium bicarbonate and ethyl acetate. The organic phased were combined, dried over anhydrous magnesium sulfate, and filtered. Solvents were evaporated, and the resulting crude material was purified by silica gel flash chromatography (eluent: 2% to 5% methanol in dichloromethane) to provide the title compound (734 mg, 86%) as a sticky solid.

Figure 2A:
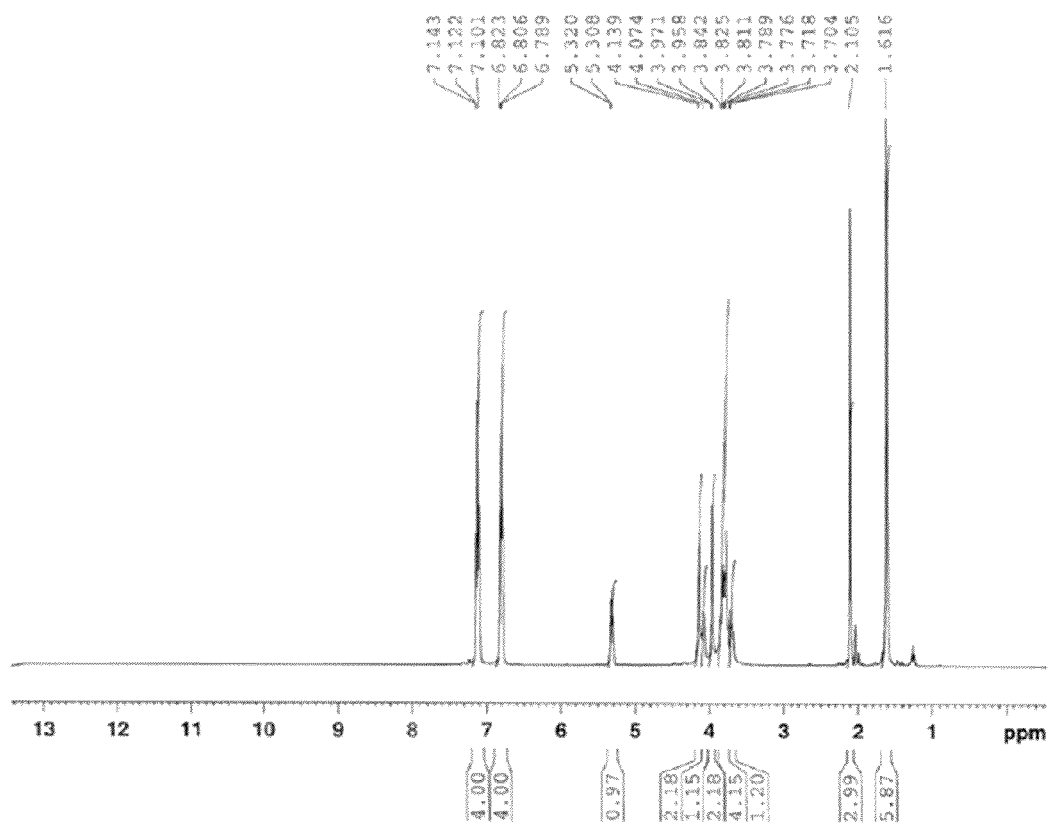
FIG. 2A is a $^1$H NMR spectrum for the compound (S)-1-chloro-3-(4-(2-(4-((R)-2,3-dihydroxypropoxy)phenyl)propan-2-yl)phenoxy)propan-2-yl acetate.
Figure 2B:
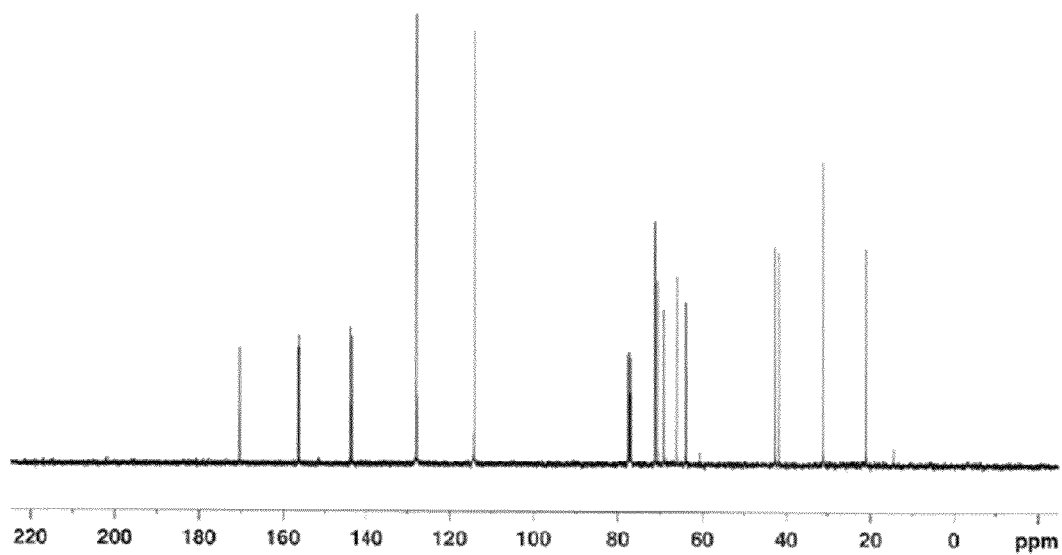
FIG. 2B is a $^{13}$C NMR spectrum for the compound (S)-1-chloro-3-(4-(2-(4-((R)-2,3-dihydroxypropoxy)phenyl)propan-2-yl)phenoxy)propan-2-yl acetate.
Figure 2C:
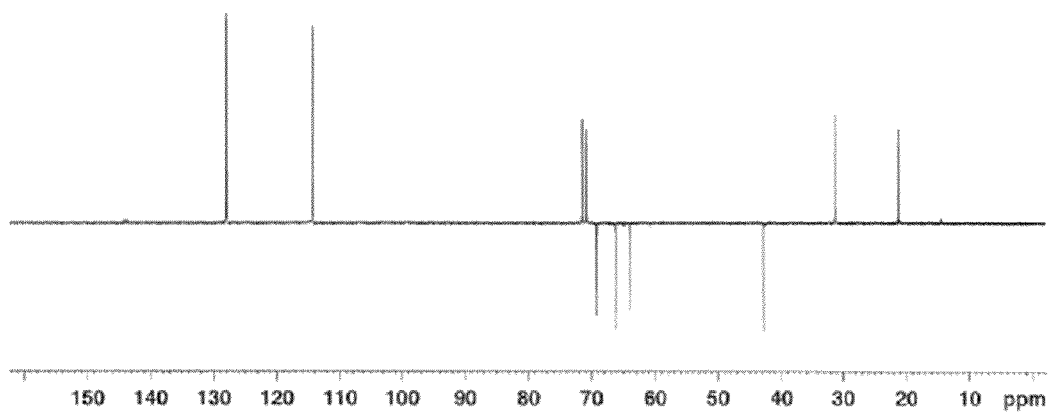
FIG. 2C is a $^{13}$C APT NMR spectrum for the compound (S)-1-chloro-3-(4-(2-(4-((R)-2,3-dihydroxypropoxy)phenyl)propan-2-yl)phenoxy)propan-2-yl acetate.

FIGS. 2(A)-(C) illustrates $^1$H and $^{13}$C-NMR data for the title compound (S)-1-chloro-3-(4-(2-(4-((R)-2,3-dihydroxypropoxy)phenyl)propan-2-yl)phenoxy)propan-2-yl acetate.

Example 8

Synthesis of (S)-3-(4-(2-(4-((S)-2-acetoxy-3-chloropropoxy)phenyl)propan-2-yl)phenoxy)propane-1,2-diyl diacetate

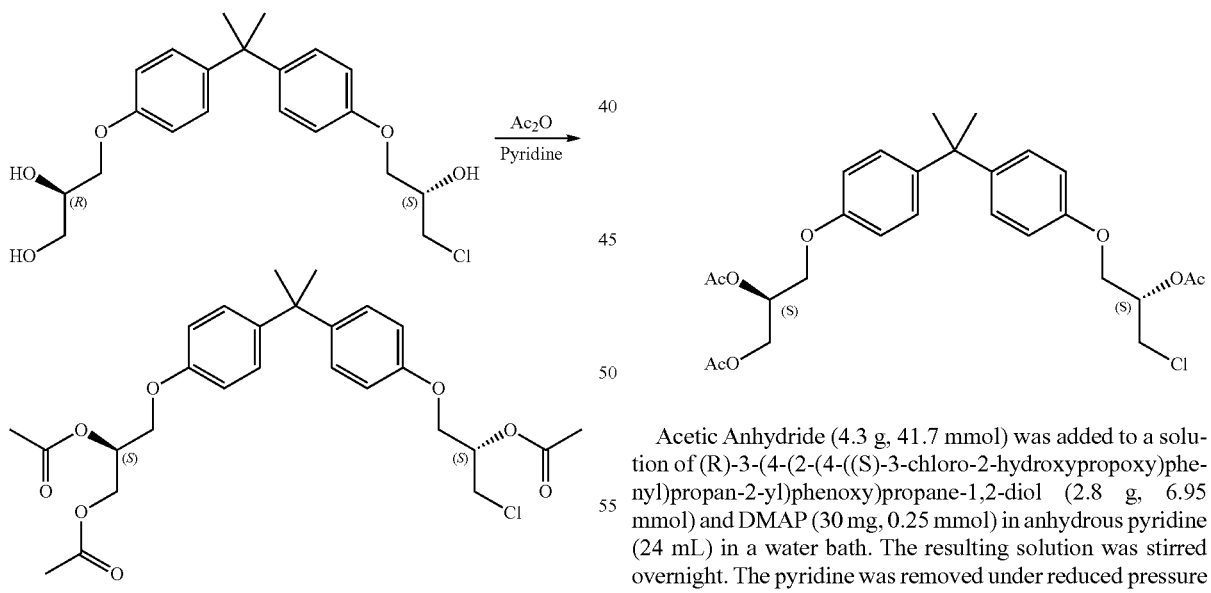

To a solution of (R)-3-(4-(2-(4-((S)-3-chloro-2-hydroxypropoxy)phenyl)propan-2-yl)phenoxy)propane-1,2-diol (500 mg, 1.27 mmol) in anhydrous pyridine (6.0 mL) were successively added acetic anhydride (605 µL, 6.35 mmol) and a catalytic amount of DMAP. After 14 h, the reaction mixture was quenched with an aqueous solution of sodium chloride and stirred for 15 min, and the resulting mixture was extracted twice with dichloromethane. The organic phases were combined, dried over anhydrous magnesium sulfate, and filtered. Solvents were evaporated, and the resulting crude material was purified by silica gel flash chromatography (eluent: 2% methanol in dichloromethane) to provide the title compound (621 mg, 94%) as a sticky solid.

In a further embodiment, the title compound (S)-3-(4-(2-(4-((S)-2-acetoxy-3-chloropropoxy)phenyl)propan-2-yl)phenoxy)propane-1,2-diyl diacetate can be synthesized via the following reaction scheme.

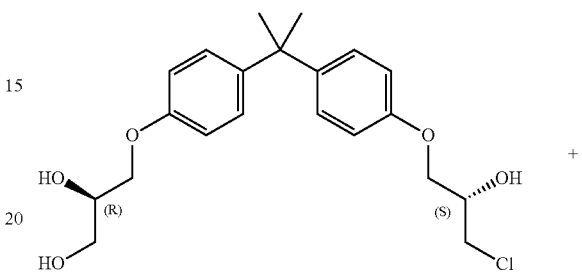

Acetic Anhydride (4.3 g, 41.7 mmol) was added to a solution of (R)-3-(4-(2-(4-((S)-3-chloro-2-hydroxypropoxy)phenyl)propan-2-yl)phenoxy)propane-1,2-diol (2.8 g, 6.95 mmol) and DMAP (30 mg, 0.25 mmol) in anhydrous pyridine (24 mL) in a water bath. The resulting solution was stirred overnight. The pyridine was removed under reduced pressure and the residue was diluted with ethyl acetate (50 mL), washed subsequently with water (2×40 mL), then cold aqueous 1M HCl (40 mL), saturated NaHCO$_3$ (40 mL) and water (40 mL). The organic layer was dried over Mg$_2$SO$_4$, filtered and concentrated to give light yellow oil. The crude product was purified by column chromatography (eluent: 5% ethyl acetate in hexane to 20% ethyl acetate in hexane) to afford the title compound (3.30 g, 91.5% yield) as a colorless viscous oil.

Figure 3A:
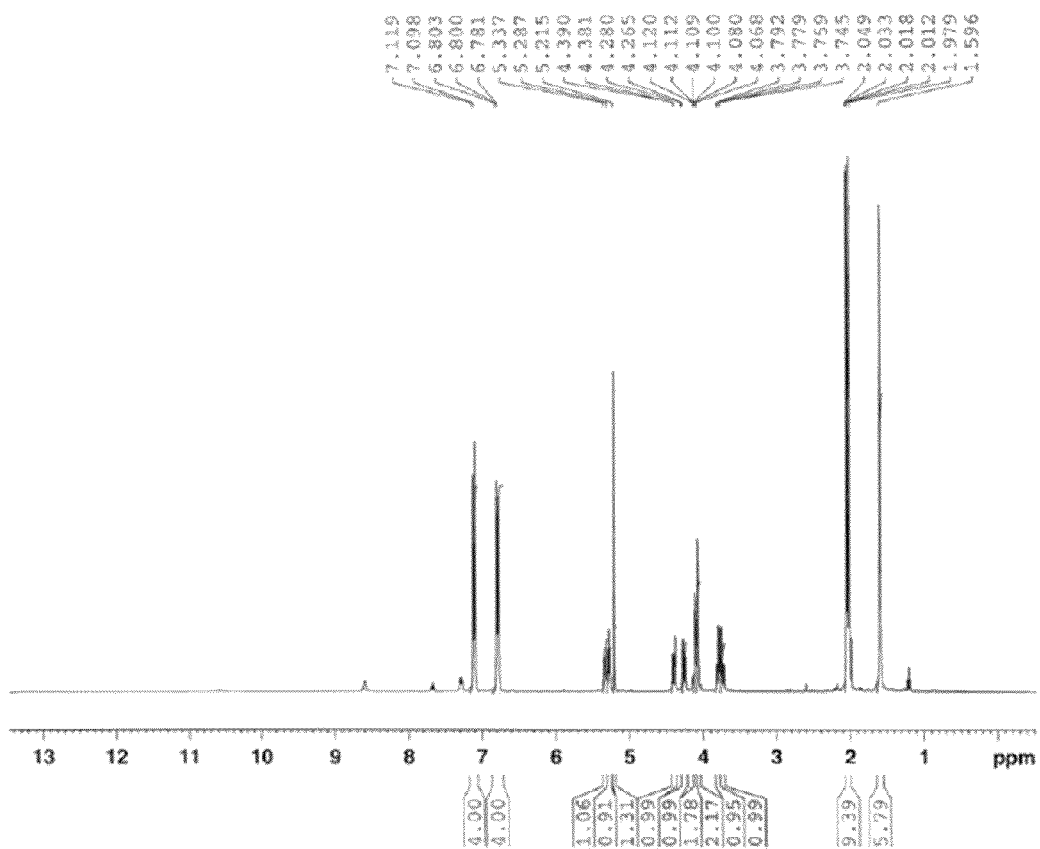
FIG. 3A is a $^1$H NMR spectrum for the compound (S)-3-(4-(2-(4-((S)-2-acetoxy-3-chloropropoxy)phenyl)propan-2-yl)phenoxy)propane-1,2-diyl diacetate.
Figure 3B:
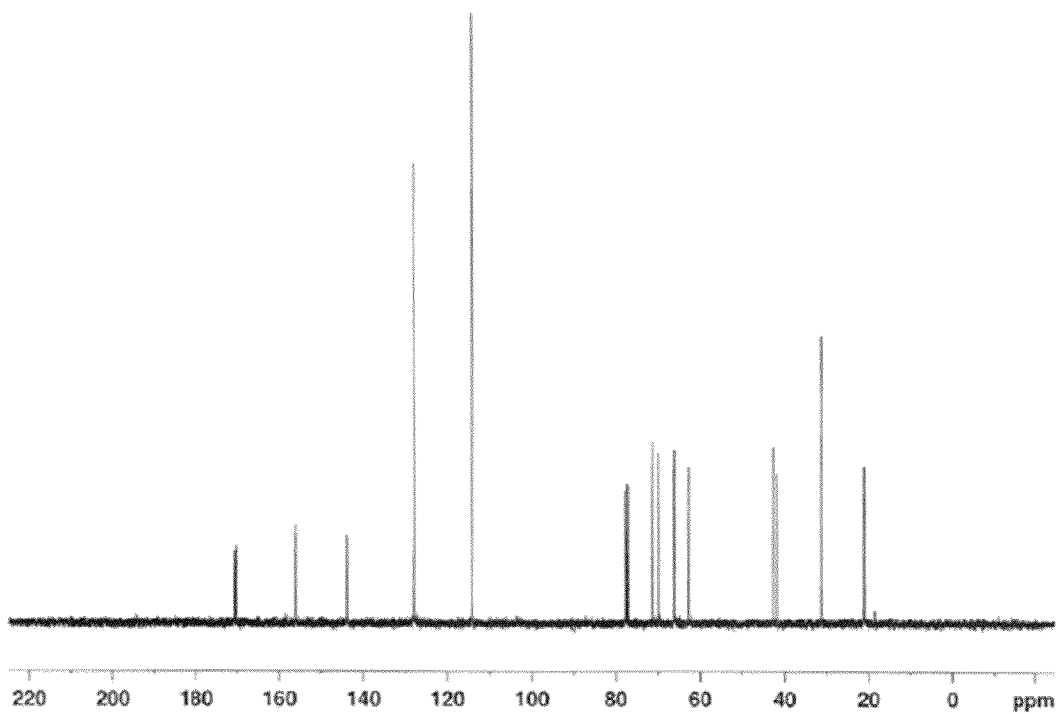
FIG. 3B is a $^{13}$C NMR spectrum for the compound (S)-3-(4-(2-(4-((S)-2-acetoxy-3-chloropropoxy)phenyl)propan-2-yl)phenoxy)propane-1,2-diyl diacetate.

FIGS. 3(A)-(B) illustrates ¹H and ¹³C-NMR data for the title compound (S)-3-(4-(2-(4-((S)-2-acetoxy-3-chloropropoxy)phenyl)propan-2-yl)phenoxy)propane-1,2-diyl diacetate.

Example 9

Synthesis of (R)-3-(4-(2-(4-hydroxyphenyl)propan-2-yl)phenoxy)propane-1,2-diol

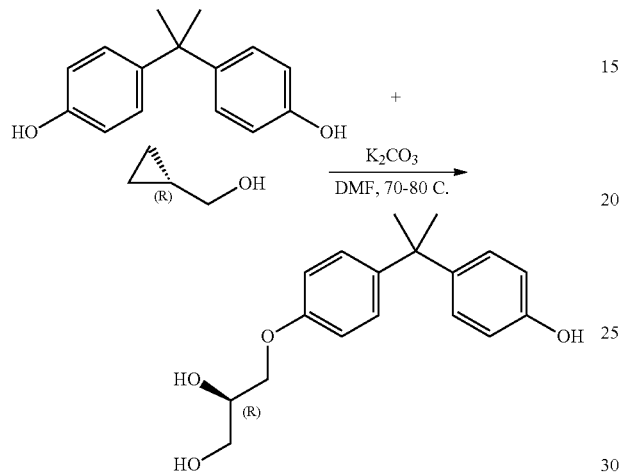

To a stirred solution of bisphenol A (10 g, 43.84 mmol, 1.0 equiv) in anhydrous dimethyl formamide (35 mL) at rt was added K₂CO₃ (9.1 g, 65.76 mmol, 1.5 equiv), and the mixture was stirred for 20 min under argon atmosphere. R(+) glycidol (3.8 mL, 56.99 mmol, 1.3 equiv) was added and the mixture was stirred for 5 h at 70-80° C. A saturated solution of ammonium chloride (10 mL) was added to the resulting orange-brown solution at room temperature. The mixture was extracted with ethyl acetate (3×15 mL). The organic layer was washed with deionized water (10 mL), was dried over anhydrous magnesium sulfate, was filtered, and was concentrated under reduced pressure. The resulting residue was purified by flash column chromatography on silica gel (eluent: 40% to 90% ethyl acetate in hexane) to provide the title compound (3.77 g, 28%) as a clear foam.

Example 10

Synthesis of (R)-3-(4-(2-(4-((R)-oxiran-2-ylmethoxy)phenyl)propan-2-yl)phenoxy)propane-1,2-diol

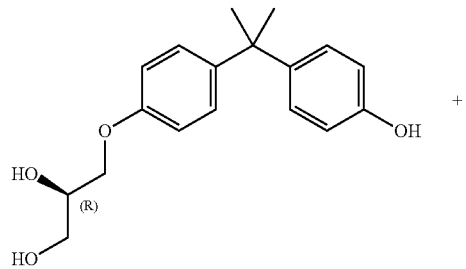

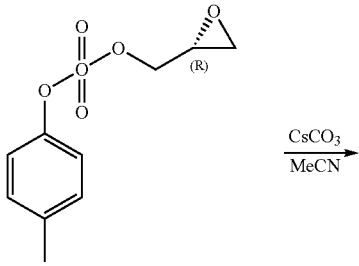

To a stirred solution of (R)-3-(4-(2-(4-hydroxyphenyl)propan-2-yl)phenoxy)propane-1,2-diol (3.77 g, 12.49 mmol, 1.0 equiv) in anhydrous acetonitrile (35 mL) at rt was added cesium carbonate (6.1 g, 18.73 mmol, 1.5 equiv), and the mixture was stirred for 20 min under argon atmosphere. A solution of (2R)-(−)-glycidyl tosylate 98% (4.3 g, 18.73 mmol, 1.5 equiv) in anhydrous acetonitrile (8 mL) was added slowly via syringe, and the mixture was allowed to react at 30° C. for 120 h. The reaction mixture was quenched at room temperature with a saturated solution of ammonium chloride (5 mL). The mixture was extracted with ethyl acetate (3×10 mL). The organic layer was washed with deionized water (10 mL), dried over anhydrous magnesium sulfate, filtered and concentrated under reduced pressure. The resulting residue was purified by flash column chromatography on silica gel (eluent: 5% to 10% methanol in dichloromethane) to provide the title compound (4.1 g, 91%) as a transparent foam.

Example 11

Synthesis of (S)-3-(4-(2-(4-((R)-oxiran-2-ylmethoxy)phenyl)propan-2-yl)phenoxy)propane-1,2-diyl diacetate

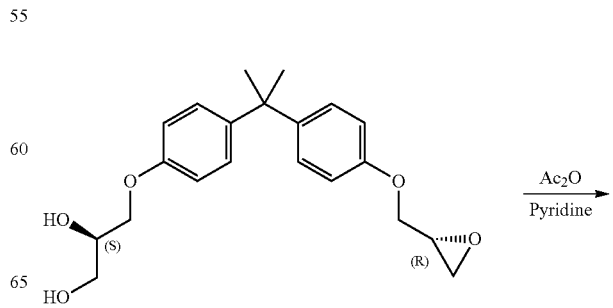

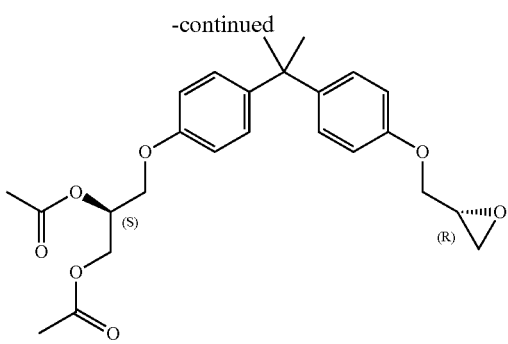

To a solution of (R)-3-(4-(2-(4-((R)-oxiran-2-ylmethoxy) phenyl)propan-2-yl)phenoxy)propane-1,2-diol (3000 mg, 8.37 mmol) in anhydrous pyridine (15.0 mL) were successively added acetic anhydride (1.97 mL, 20.92 mmol) and a catalytic amount of DMAP. After 14 h, the reaction mixture was quenched with an aqueous solution of sodium chloride and stirred for 15 min, and the resulting mixture was extracted twice with dichloromethane. The organic phases were combined, dried over anhydrous magnesium sulfate and filtered. Solvents were evaporated, and the resulting crude material was purified by silica gel flash chromatography (eluent: 2% methanol in dichloromethane) to provide the title compound (3.3 g, 89%) as a sticky solid.

Figure 4A:
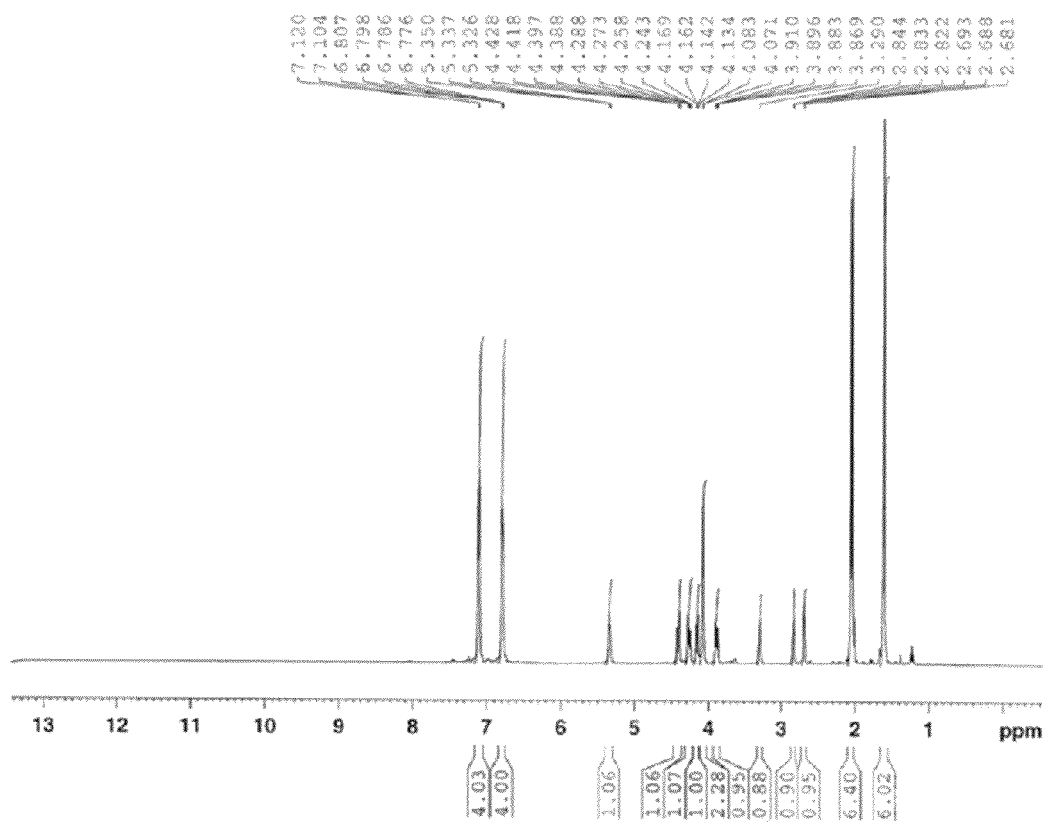
FIG. 4A is a $^1$H NMR spectrum for the compound (S)-3-(4-(2-(4-((R)-oxiran-2-ylmethoxy)phenyl)propan-2-yl)phenoxy)propane-1,2-diyl diacetate.
Figure 4B:
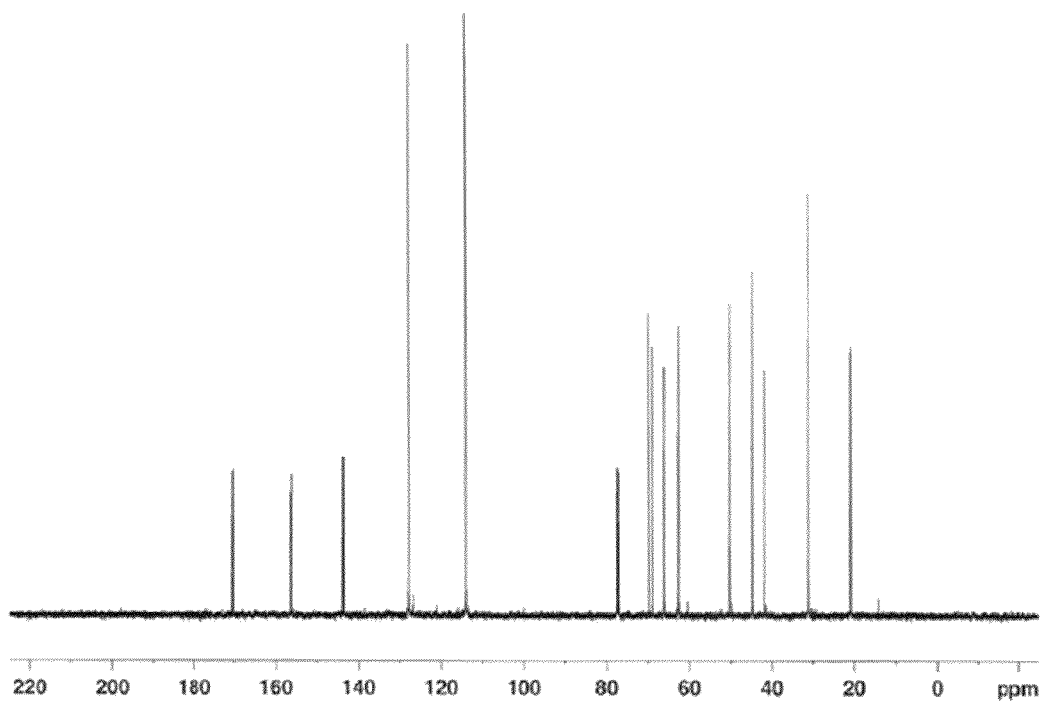
FIG. 4B is a $^{13}$C NMR spectrum for the compound (S)-3-(4-(2-(4-((R)-oxiran-2-ylmethoxy)phenyl)propan-2-yl)phenoxy)propane-1,2-diyl diacetate.
Figure 4C:
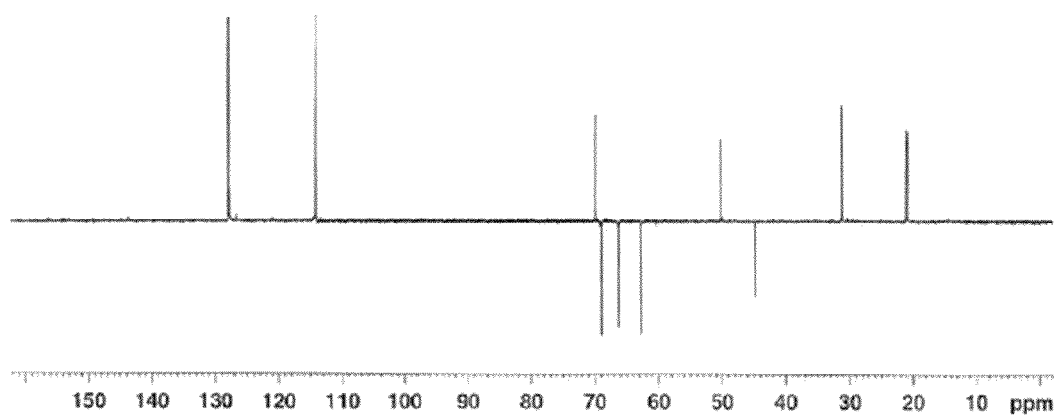
FIG. 4C is a $^{13}$C APT NMR spectrum for the compound (S)-3-(4-(2-(4-((R)-oxiran-2-ylmethoxy)phenyl)propan-2-yl)phenoxy)propane-1,2-diyl diacetate.

FIGS. 4(A)-(C) illustrates $^1$H and $^{13}$C-NMR data for the title compound (S)-3-(4-(2-(4-((R)-oxiran-2-ylmethoxy) phenyl)propan-2-yl)phenoxy)propane-1,2-diyl diacetate.

Example 12

Synthesis of (S)-3-(4-(2-(4-((S)-3-chloro-2-hydroxypropoxy)phenyl)propan-2-yl)phenoxy)propane-1,2-diyl diacetate

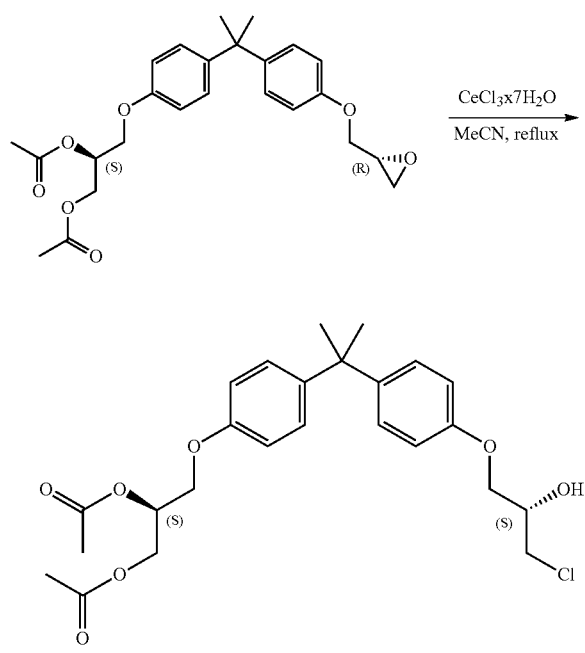

To a solution of (S)-3-(4-(2-(4-((R)-oxiran-2-ylmethoxy) phenyl)propan-2-yl)phenoxy)propane-1,2-diyl diacetate (180 mg, 0.41 mmol, 1 equiv) in acetonitrile (6 mL) was added CeCl$_3$.7H$_2$O (227 mg, 0.61 mmol, 1.5 equiv) and the mixture was refluxed for 6 h. The resulting white paste was filtered and washed with ethyl acetate and the clear suspension was concentrated under reduced pressure. The resulting residue was purified by flash column chromatography on silica gel (eluent: 20% hexane in ethyl acetate to 60% ethylacetate) to provide the title compound (172 mg, 88%) as a sticky mass.

Figure 5A:
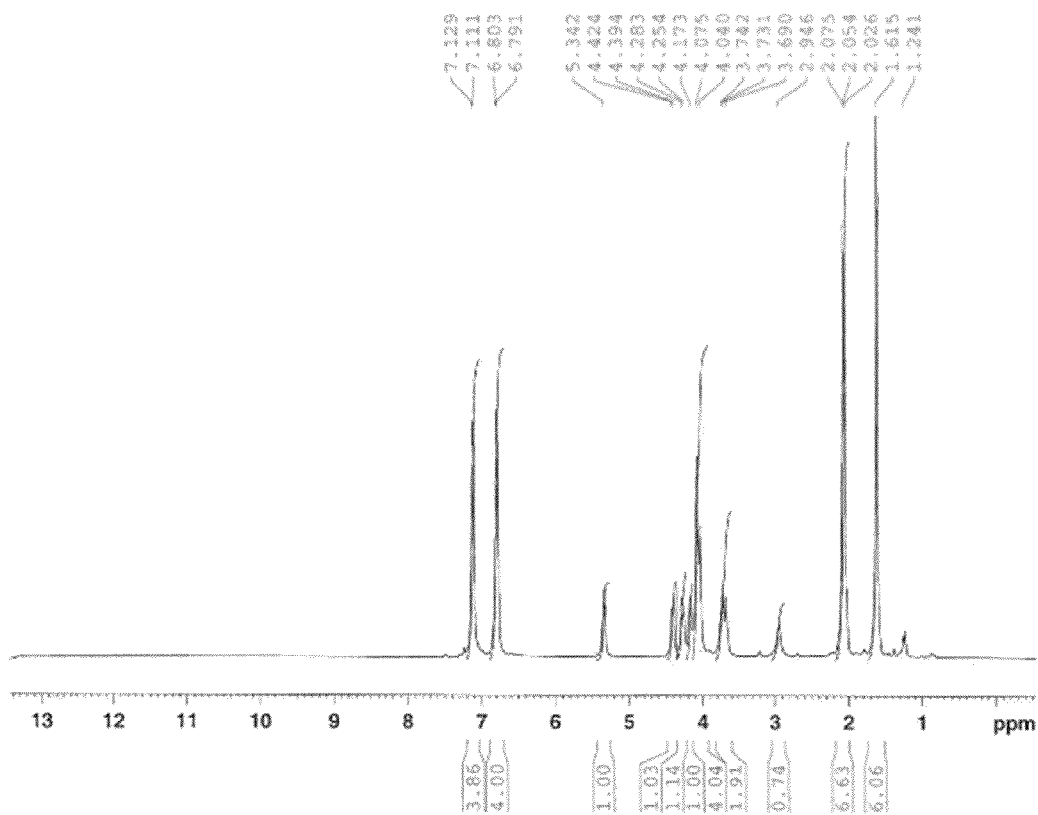
FIG. 5A is a $^1$H NMR spectrum for the compound (S)-3-(4-(2-(4-((S)-3-chloro-2-hydroxypropoxy)phenyl)propan-2-yl)phenoxy)propane-1,2-diyl diacetate.
Figure 5B:
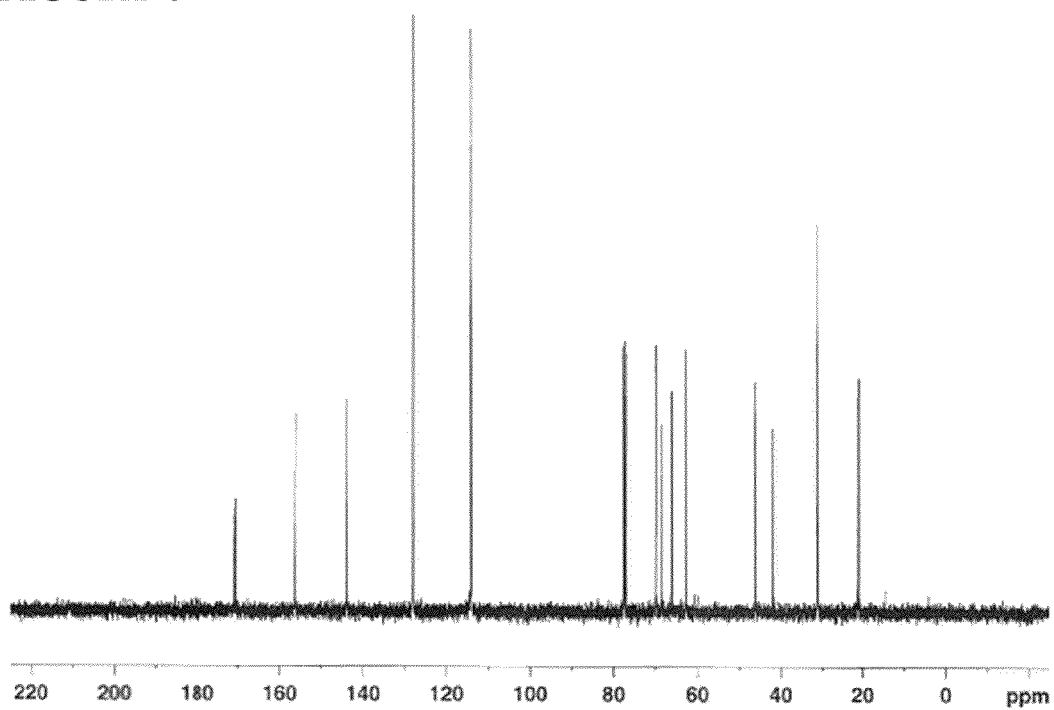
FIG. 5B is a $^{13}$C NMR spectrum for the compound (S)-3-(4-(2-(4-((S)-3-chloro-2-hydroxypropoxy)phenyl)propan-2-yl)phenoxy)propane-1,2-diyl diacetate.
Figure 5C:
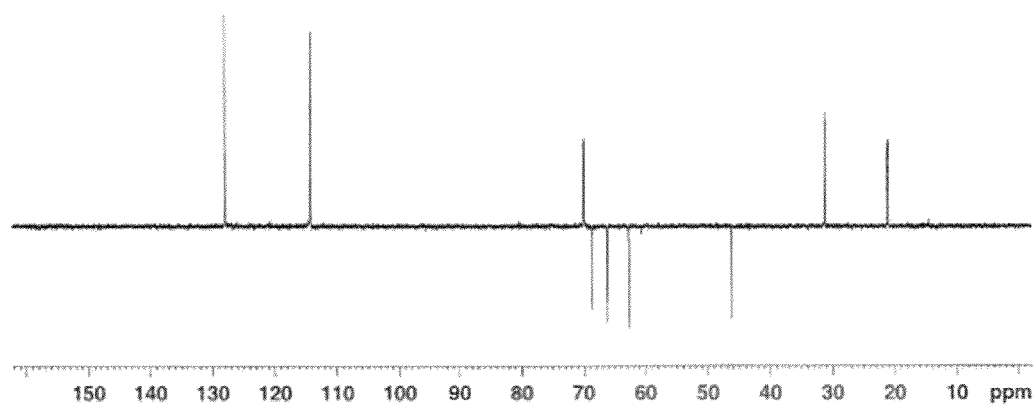
FIG. 5C is a $^{13}$C APT NMR spectrum for the compound (S)-3-(4-(2-(4-((S)-3-chloro-2-hydroxypropoxy)phenyl)propan-2-yl)phenoxy)propane-1,2-diyl diacetate.

FIGS. 5(A)-(C) are $^1$H, $^{13}$C and $^{13}$C APT NMR spectra for the title compound (S)-3-(4-(2-(4-((S)-3-chloro-2-hydroxypropoxy)phenyl)propan-2-yl)phenoxy)propane-1,2-diyl diacetate.

Example 13

(S)-3-(4-(2-(4-((S)-3-chloro-2-hydroxypropoxy)phenyl)propan-2-yl)phenoxy)propane-1,2-diol trisuccinate

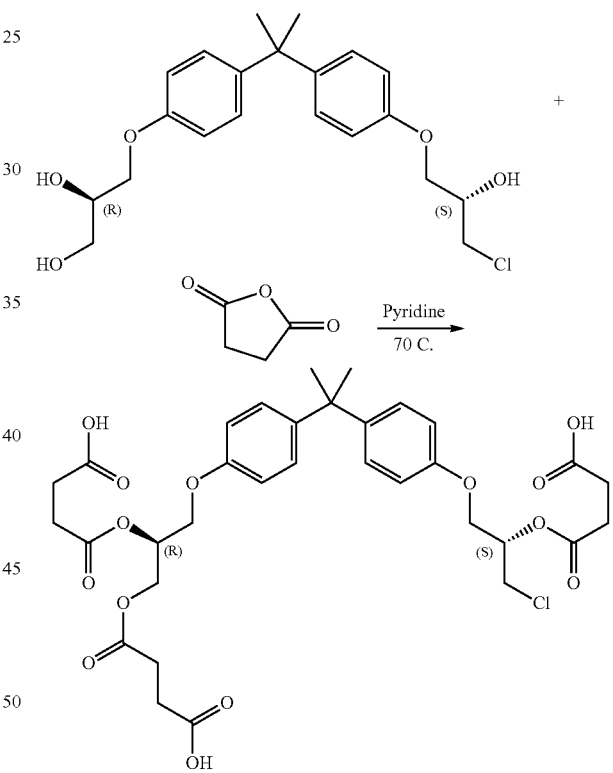

To a solution of (R)-3-(4-(2-(4-((S)-3-chloro-2-hydroxypropoxy)phenyl)propan-2-yl)phenoxy)propane-1,2-diol (700 mg, 1.77 mmol) in anhydrous pyridine (6.0 ml) were added succinic anhydride (710 mg, 7.10 mmol) and the mixture was heated at 70° C. After 3 h, the reaction mixture was quenched with an aqueous solution of sodium chloride and stirred for 15 min, and the resulting mixture was extracted twice with ethyl acetate. The organic phases were combined, dried over anhydrous magnesium sulfate, and filtered. Solvents were evaporated, and the resulting crude material was purified by silica gel flash chromatography (eluent: 5% to 30% methanol in dichloromethane) to provide the title compound.

The molecular formula of the title compound may also be illustrated as follows:

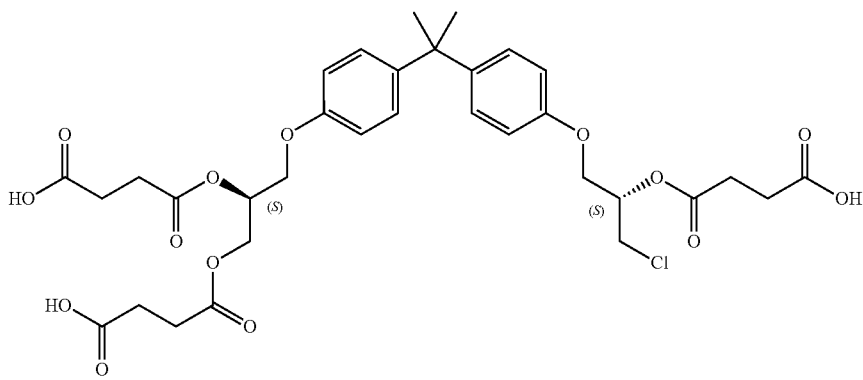

Figure 6A:
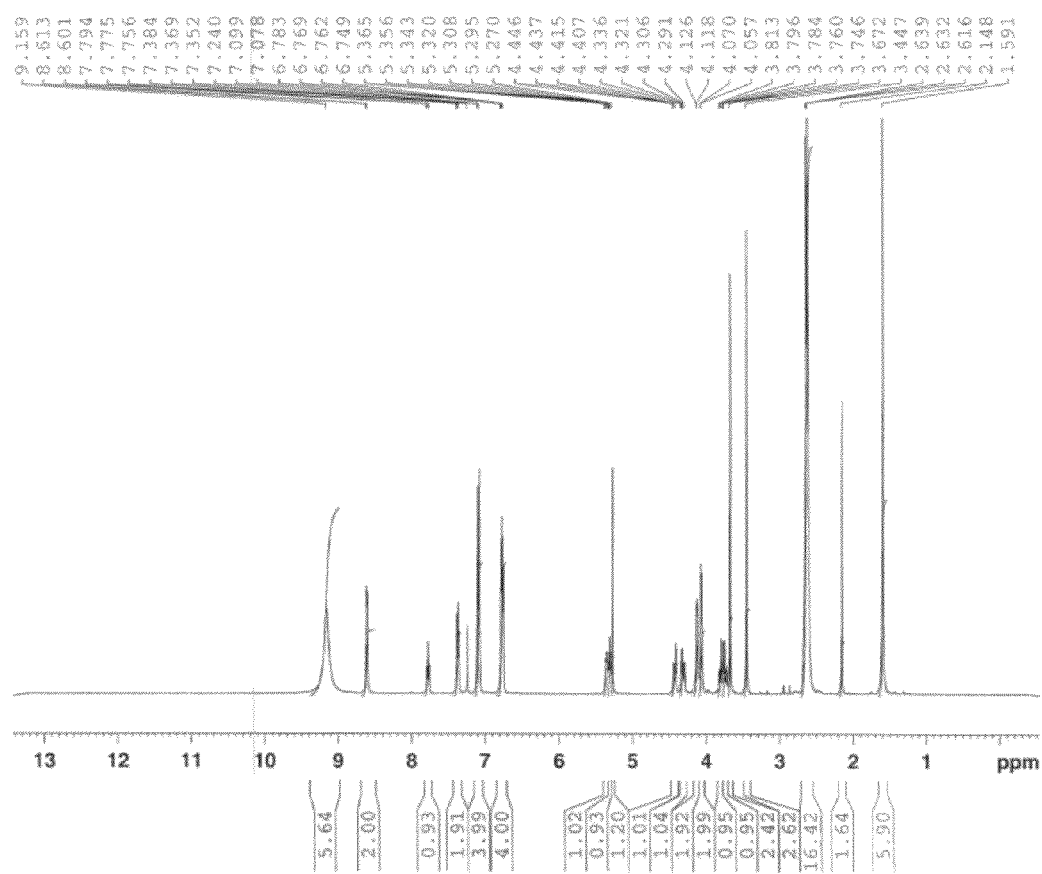
FIG. 6A is a $^1$H NMR spectrum for the compound (S)-3-(4-(2-(4-((S)-3-chloro-2-hydroxypropoxy)phenyl)propan-2-yl)phenoxy)propane-1,2-diol trisuccinate.
Figure 6B:
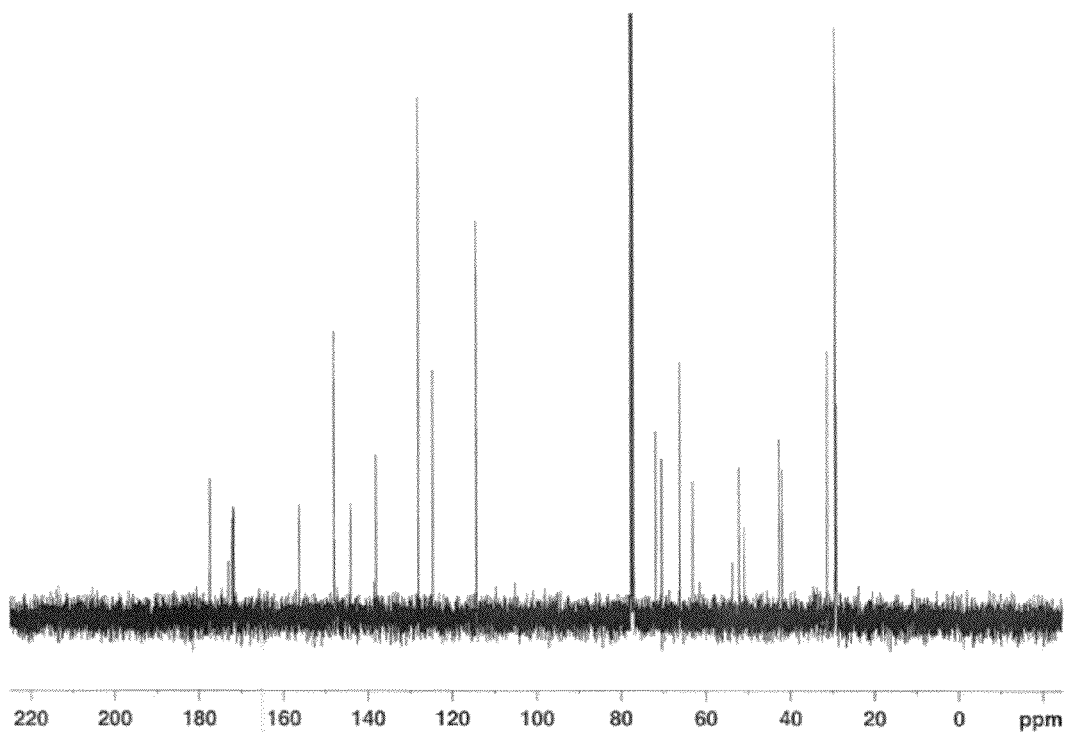
FIG. 6B is a $^{13}$C NMR spectrum for the compound (S)-3-(4-(2-(4-((S)-3-chloro-2-hydroxypropoxy)phenyl)propan-2-yl)phenoxy)propane-1,2-diol trisuccinate.
Figure 6C:
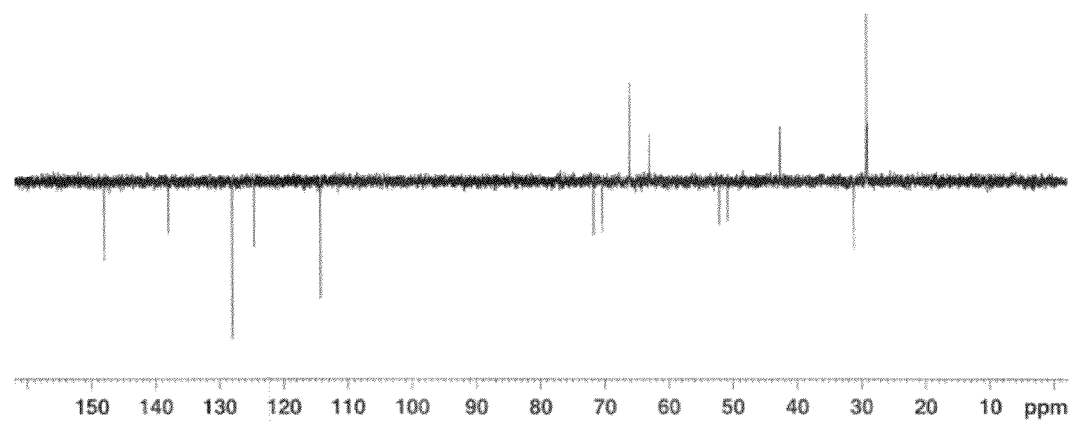
FIG. 6C a $^{13}$C APT NMR spectrum for the compound (S)-3-(4-(2-(4-((S)-3-chloro-2-hydroxypropoxy)phenyl) propan-2-yl)phenoxy)propane-1,2-diol trisuccinate.

FIGS. 6(A)-(C) are $^1$H and $^{13}$C and $^{13}$C APT NMR spectra for the title compound (S)-3-(4-(2-(4-((S)-3-chloro-2-hydroxypropoxy)phenyl)propan-2-yl)phenoxy)propane-1,2-diol trisuccinate.

Figure 6D:
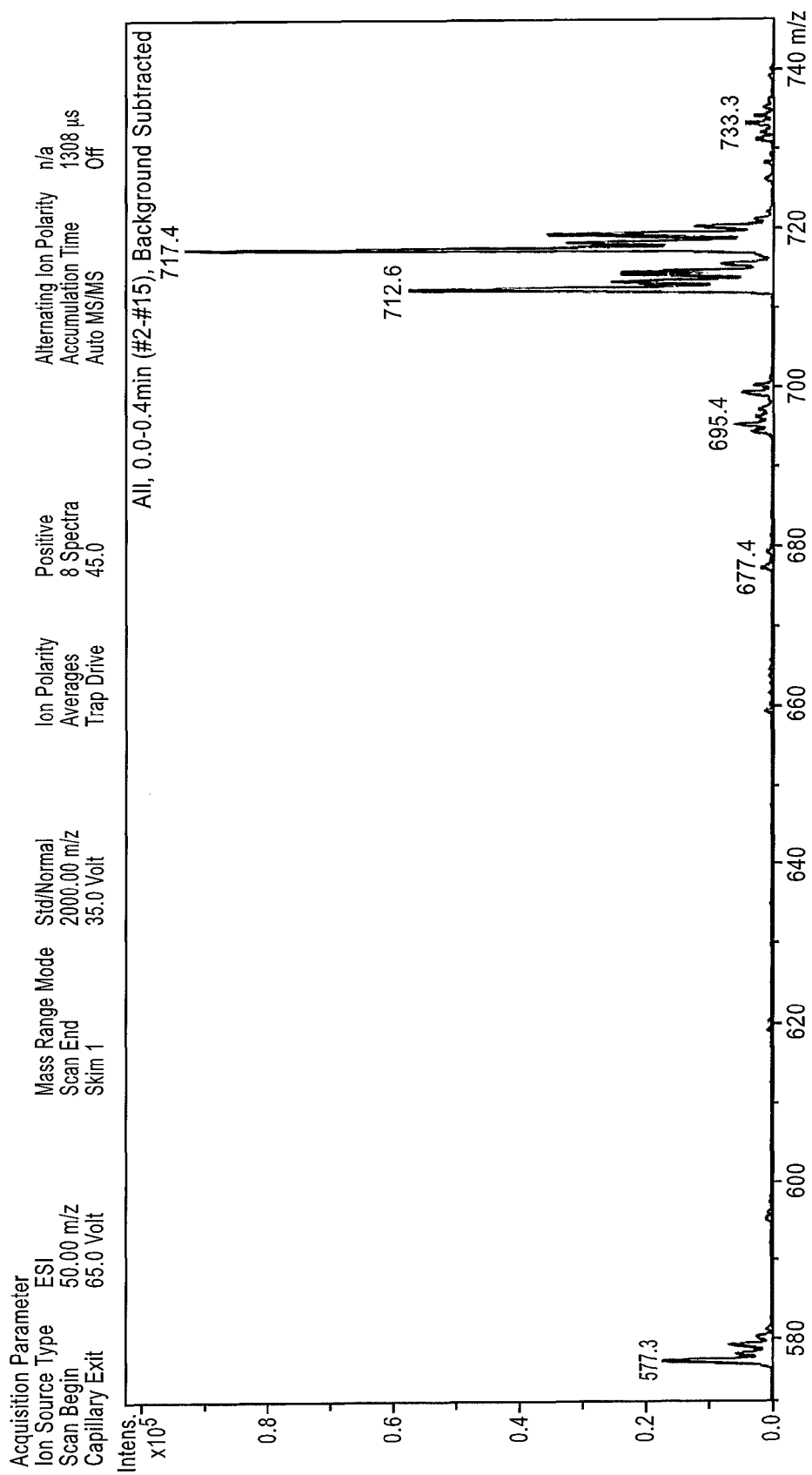
FIG. 6D illustrates electrospray ionization mass spectrometry data for (S)-3-(4-(2-(4-((S)-3-chloro-2-hydroxypropoxy)phenyl)propan-2-yl)phenoxy)propane-1,2-diol trisuccinate with positive ion polarity.
Figure 6E:
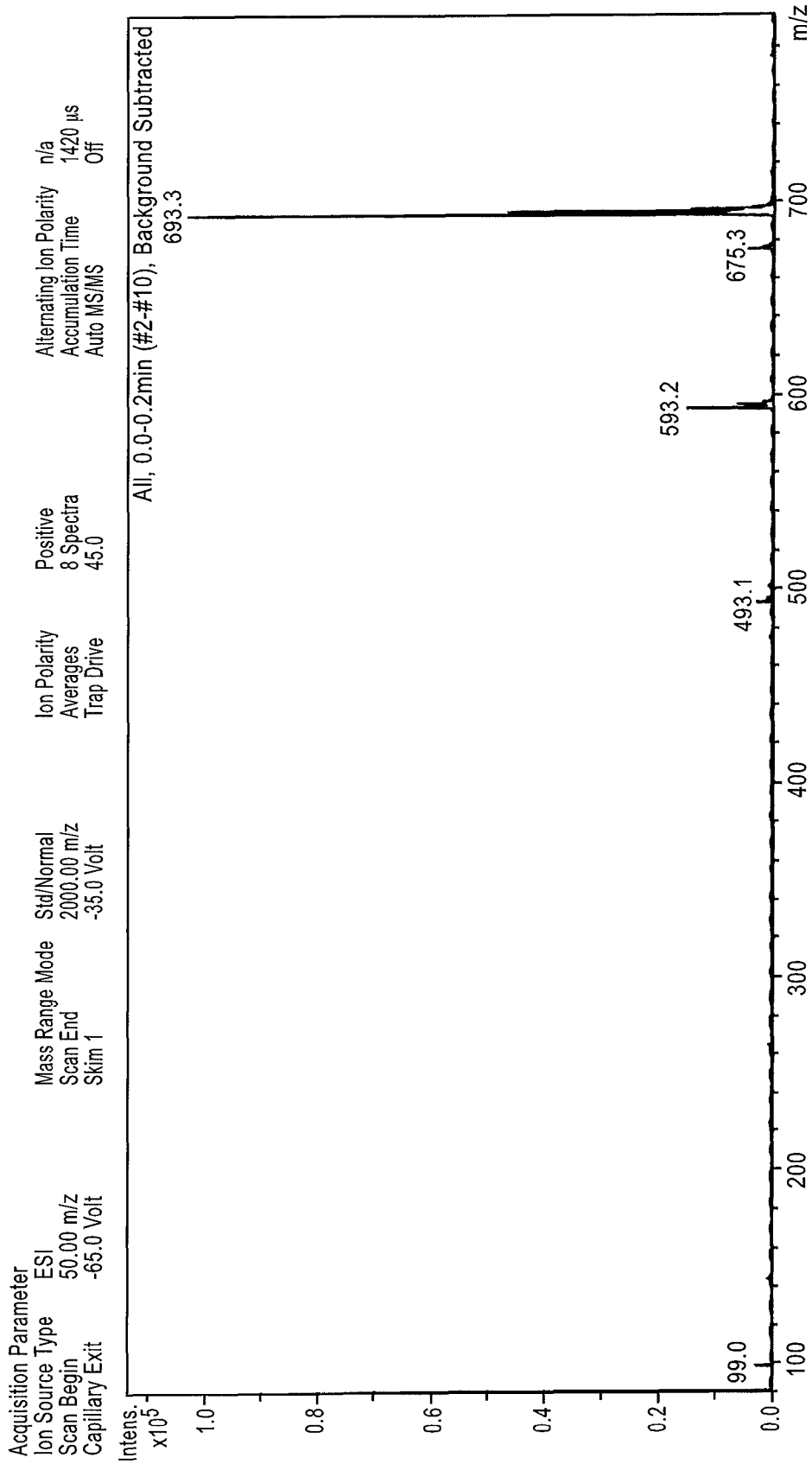
FIG. 6E illustrates electrospray ionization mass spectrometry data for (S)-3-(4-(2-(4-((S)-3-chloro-2-hydroxypropoxy)phenyl)propan-2-yl)phenoxy)propane-1,2-diol trisuccinate with negative ion polarity.

FIGS. 6(D) and (E) are ESI MS spectrographs for (S)-3-(4-(2-(4-((S)-3-chloro-2-hydroxypropoxy)phenyl)propan-2-yl)phenoxy)propane-1,2-diol trisuccinate.

Example 14

Synthesis of (2S)-1-chloro-3-(4-(2-(4-(oxiran-2-ylmethoxy)phenyl)propan-2-yl)phenoxy)propan-2-ol

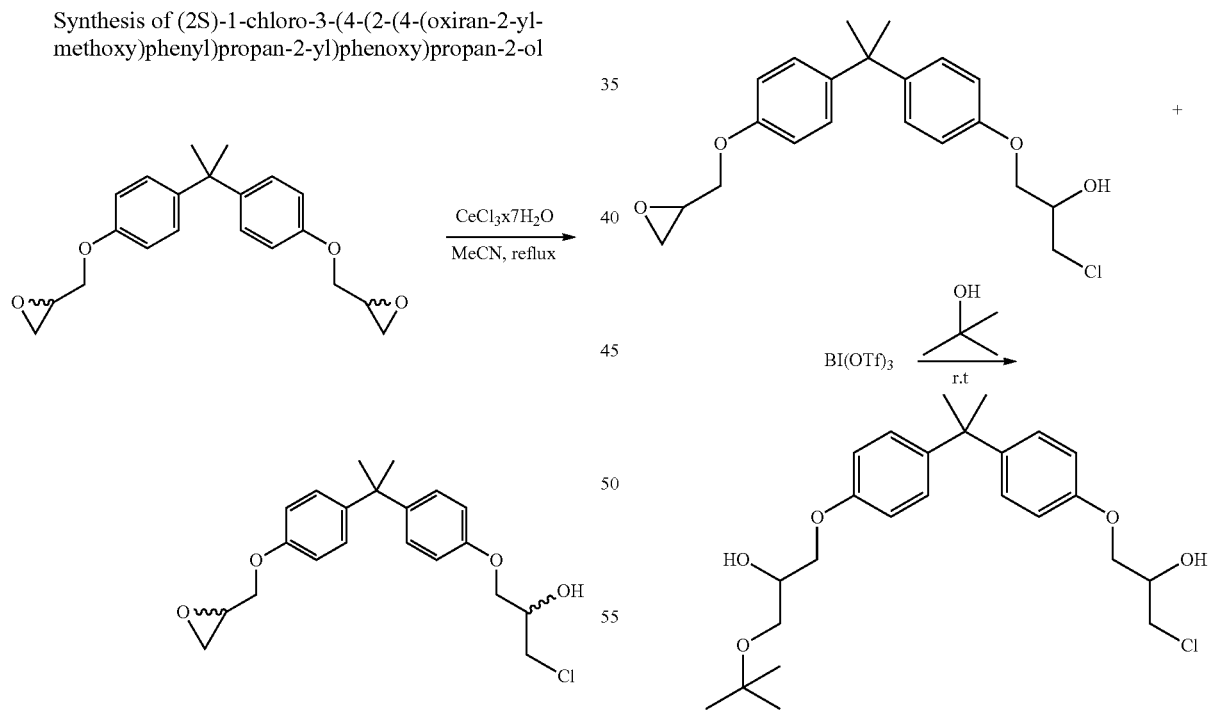

To a solution of racemic derivative Bisphenol A diglycidyl ether (13.30 g, 39.27 mmol, 1 equiv) in acetonitrile (30 mL) was added CeCl$_3$.7H$_2$O (7.30 g, 19.63 mmol, ½ equiv) and the mixture was refluxed for 3.5 h. The resulting white paste was filtered and washed with ethyl acetate and the clear suspension was concentrated under reduced pressure. The resulting residue was purified by flash column chromatography on silica gel (eluent: 10% ethyl acetate in hexane) to provide (2S)-1-chloro-3-(4-(2-(4-(oxiran-2-ylmethoxy)phenyl)propan-2-yl)phenoxy)propan-2-ol (2.12 g, 14%) as a pale liquid.

Example 15

Synthesis of 1-(tert-butoxy)-3-(4-(2-(4-(3-chloro-2-hydroxypropoxy)phenyl)propan-2-yl)phenoxy)propan-2-ol To a solution of racemic 1-chloro-3-(4-(2-(4-(oxiran-2-ylmethoxy)phenyl)propan-2-yl)phenoxy)propan-2-ol (300 mg, 0.8 mmol, 1 equiv) in t-Butanol (5 mL) was added solid Bismuth (III) trifluoromethanesulfonate (10 mg, 0.015 mmol, ⅟₅₀ equiv) in one portion and the mixture was stirred at room temperature for 12 h. Sodium bicarbonate was added (0.5 mL), the organic solvent was evaporated under reduced pressure, and the residue was extracted with dichloromethane (3×10 mL). The organic layer was washed with deionized water (2×10 mL), was dried over anhydrous magnesium sulfate, was filtered, and was concentrated under reduced pressure. The resulting residue was purified by flash column chromatography on silica gel (eluent: 40% to 80% ethyl acetate in hexane) to provide 1-(tert-butoxy)-3-(4-(2-(4-(3-chloro-2-hydroxypropoxy)phenyl)propan-2-yl)phenoxy)propan-2-ol (100 mg, 28%) as a foam.

Example 16

Synthesis of (S)-3-(4-(2-(4-((S)-3-chloro-2-(propionyloxy)propoxy)phenyl)propan-2-yl)phenoxy)propane-1,2-diyl dipropionate

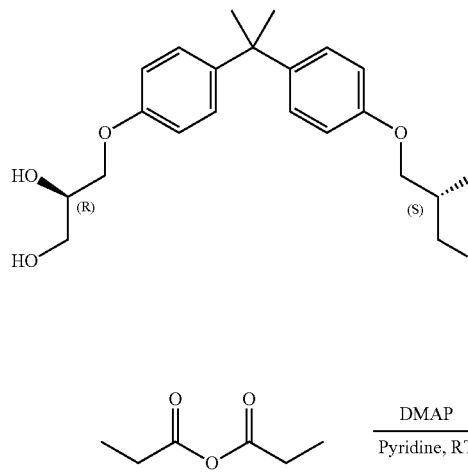

Propanoic Anhydride (4.3 g, 41.7 mmol) was added to a solution of (R)-3-(4-(2-(4-((S)-3-chloro-2-hydroxypropoxy)phenyl)propan-2-yl)phenoxy)propane-1,2-diol (2.8 g, 6.95 mmol) and DMAP (30 mg, 0.25 mmol) in anhydrous pyridine (24 mL) in a water bath. The resulting solution was stirred overnight. The pyridine was removed under reduced pressure and the residue was diluted with ethyl acetate (50 mL), washed subsequently with water (2×40 mL), then cold aqueous 1M HCl (40 mL), saturated NaHCO$_3$ (40 mL) and water (40 mL). The organic layer was dried over Mg$_2$SO$_4$, filtered and concentrated to give light yellow oil. The crude product was purified by column chromatography (eluent: 5% ethyl acetate in hexane to 20% ethyl acetate in hexane) to afford the title compound (3.30 g, 91.5% yield) as a colorless viscous oil.

Figure 15A:
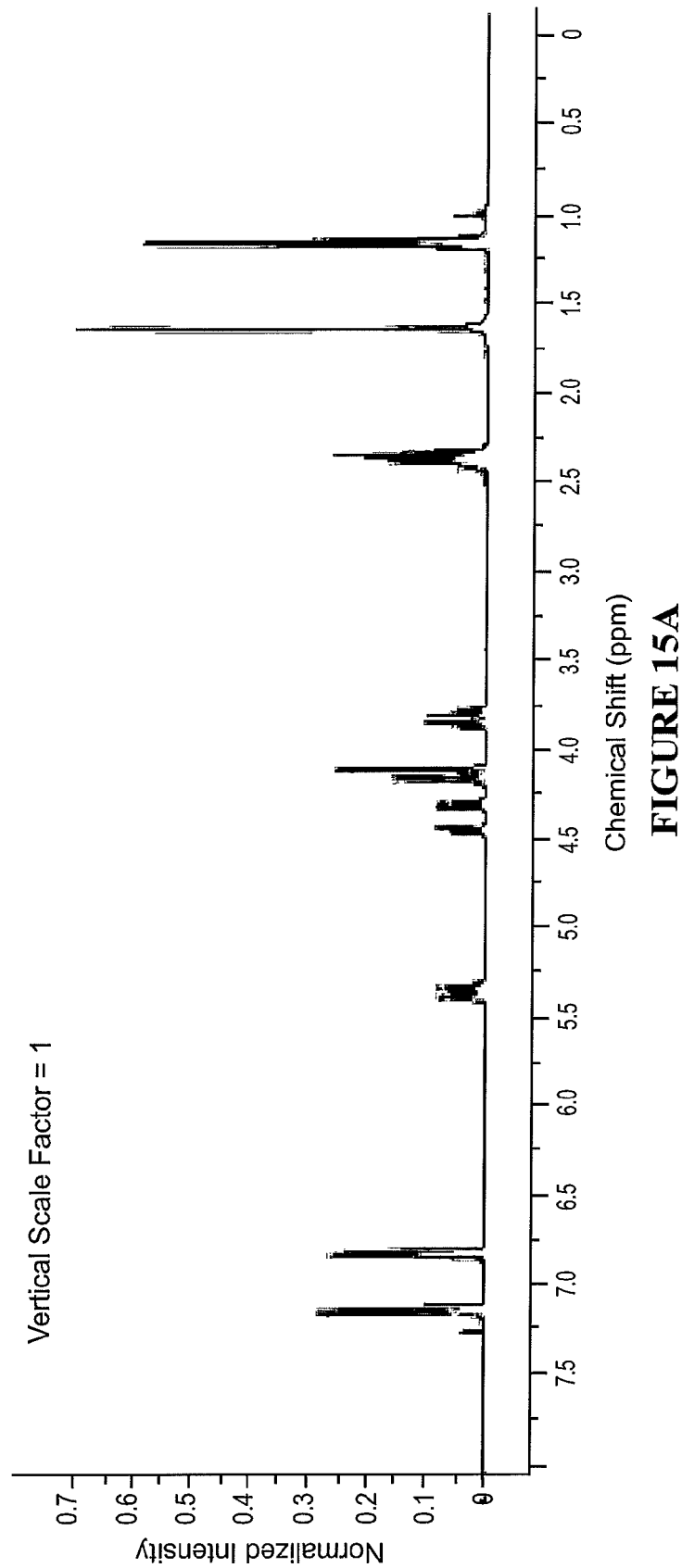
FIG. 15A is a $^1$H NMR spectrum for the compound (S)-3-(4-(2-(4-((S)-3-chloro-2-(propionyloxy)propoxy)phenyl)propan-2-yl)phenoxy)propane-1,2-diyl dipropionate.
Figure 15B:
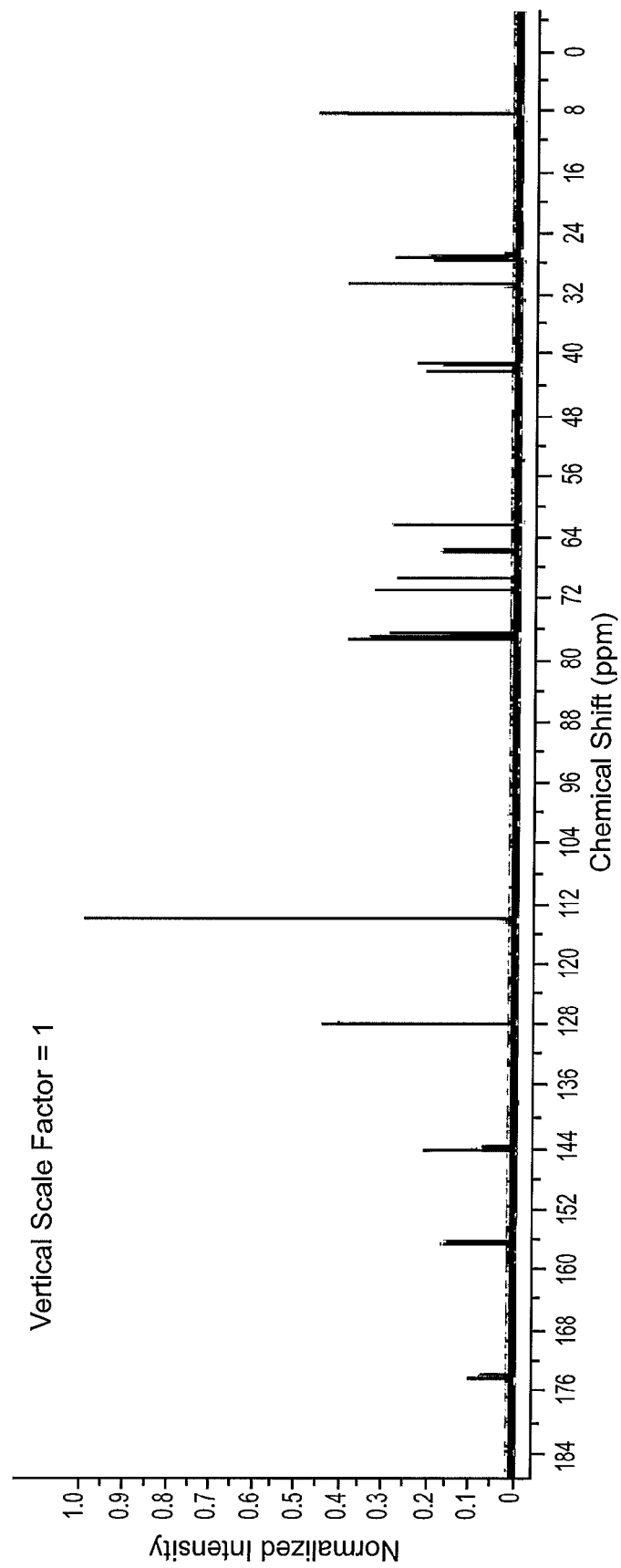
FIG. 15B is a $^{13}$C NMR spectrum for the compound (S)-3-(4-(2-(4-((S)-3-chloro-2-(propionyloxy)propoxy)phenyl)propan-2-yl)phenoxy)propane-1,2-diyl dipropionate.

FIGS. 15A and 15B are $^1$H and $^{13}$C NMR spectra of (S)-3-(4-(2-(4-((S)-3-chloro-2-(propionyloxy)propoxy)phenyl)propan-2-yl)phenoxy)propane-1,2-diyl dipropionate.

Example 17

Synthesis of (S)-3-(4-(2-(4-((S)-2-(butyryloxy)-3-chloropropoxy)phenyl)propan-2-yl)phenoxy)propane-1,2-diyl dibutyrate

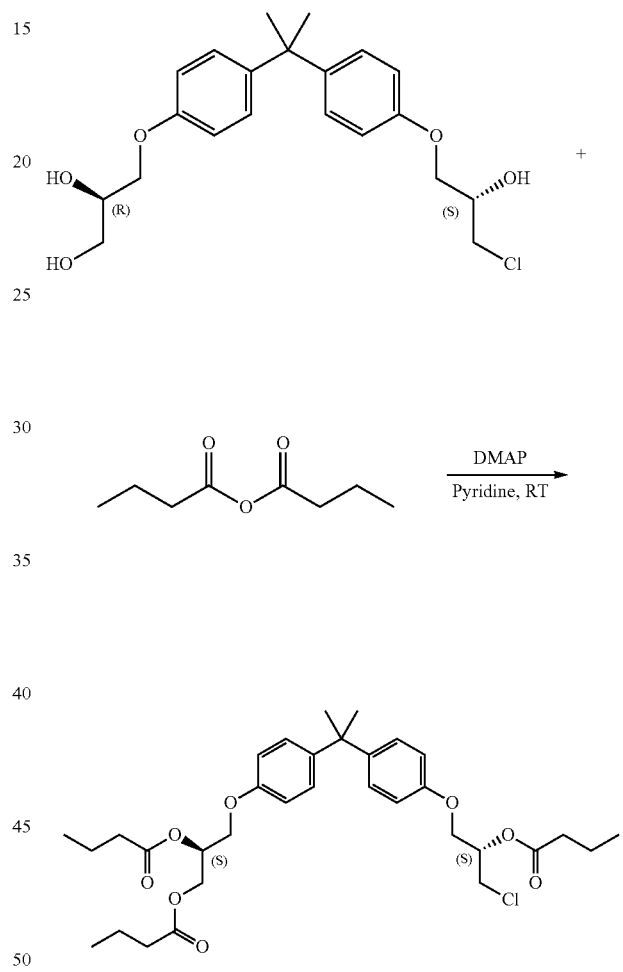

Butanoic Anhydride (4.3 g, 41.7 mmol) was added to a solution of (R)-3-(4-(2-(4-((S)-3-chloro-2-hydroxypropoxy)phenyl)propan-2-yl)phenoxy)propane-1,2-diol (2.8 g, 6.95 mmol) and DMAP (30 mg, 0.25 mmol) in anhydrous pyridine (24 mL) in a water bath. The resulting solution was stirred overnight. The pyridine was removed under reduced pressure and the residue was diluted with ethyl acetate (50 mL), washed subsequently with water (2×40 mL), then cold aqueous 1M HCl (40 mL), saturated NaHCO$_3$ (40 mL) and water (40 mL). The organic layer was dried over Mg$_2$SO$_4$, filtered and concentrated to give light yellow oil. The crude product was purified by column chromatography (eluent: 5% ethyl acetate in hexane to 20% ethyl acetate in hexane) to afford the title compound (3.30 g, 91.5% yield) as a colorless viscous oil.

Figure 16A:
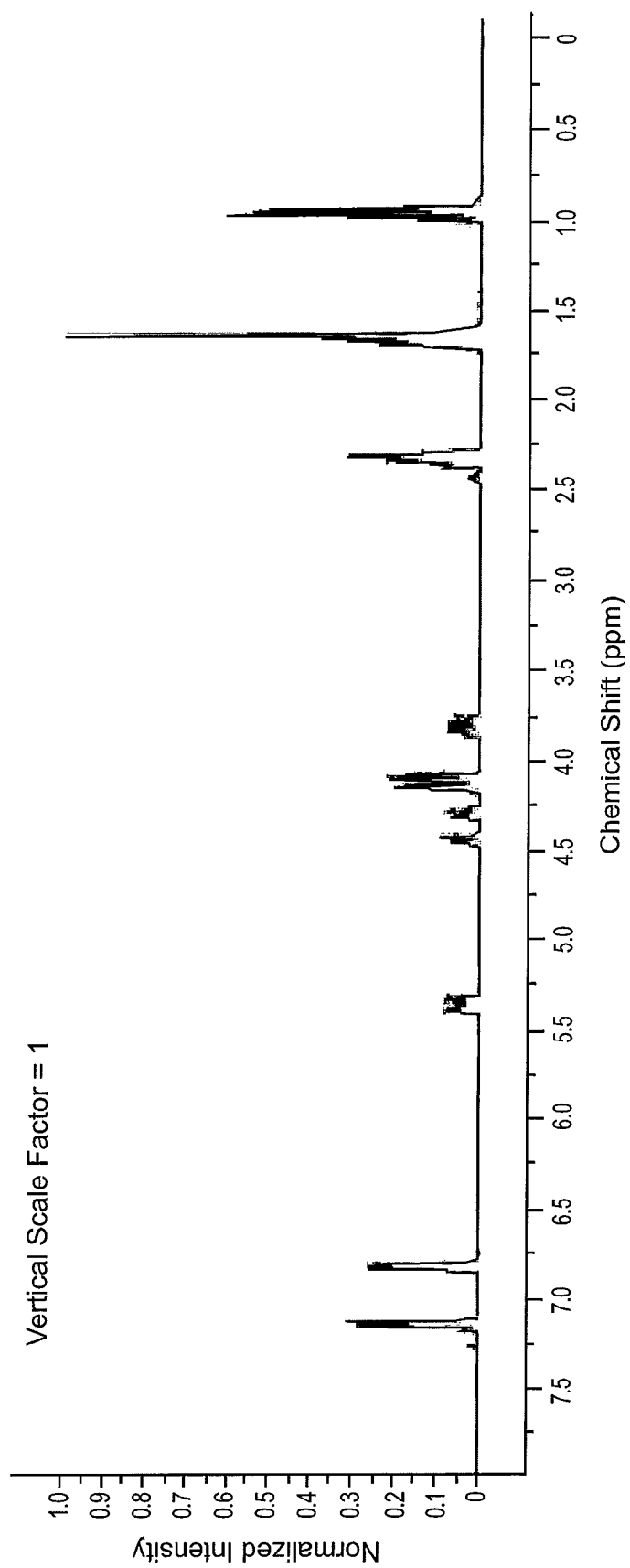
FIG. 16A is a $^1$H NMR spectrum for the compound (S)-3-(4-(2-(4-((S)-2-(butyryloxy)-3-chloropropoxy)phenyl)propan-2-yl)phenoxy)propane-1,2-diyl dibutyrate.
Figure 16B:
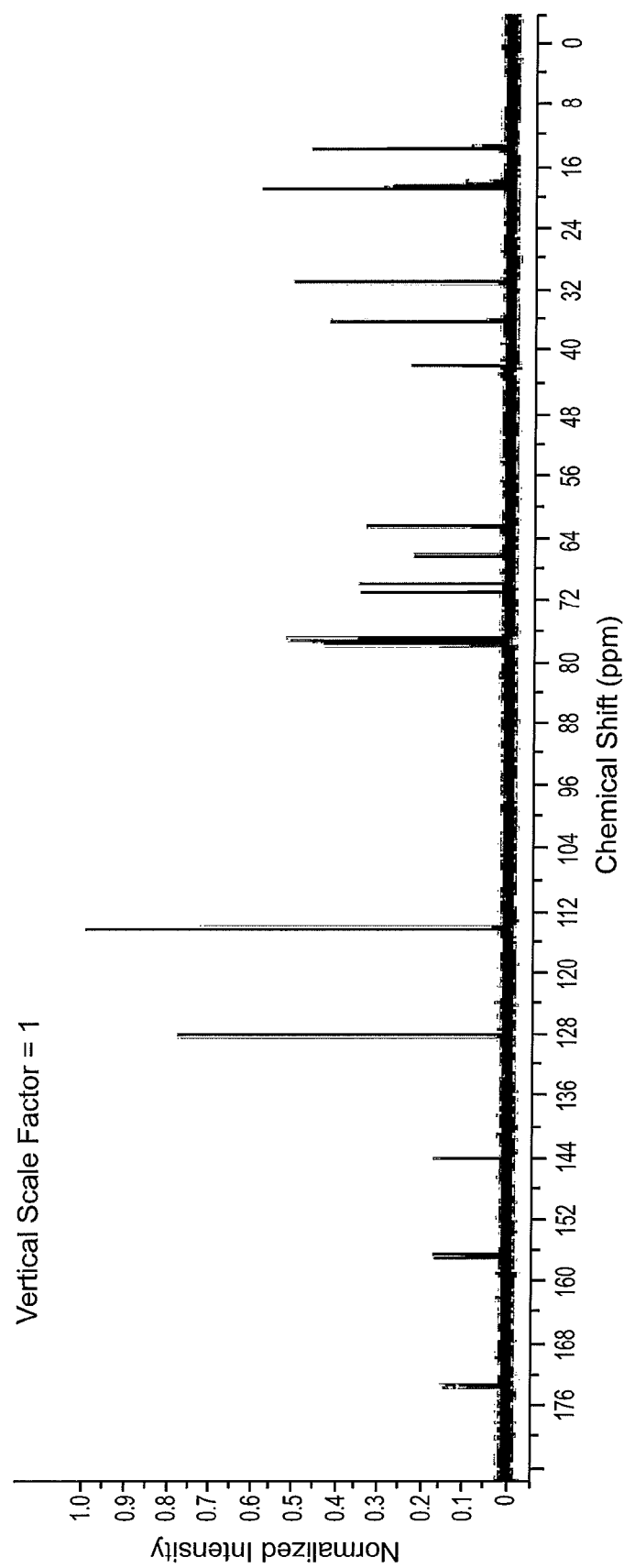
FIG. 16B is a $^{13}$C NMR spectrum for the compound (S)-3-(4-(2-(4-((S)-2-(butyryloxy)-3-chloropropoxy)phenyl)propan-2-yl)phenoxy)propane-1,2-diyl dibutyrate.

FIGS. 16A and 16B are $^1$H and $^{13}$C NMR spectra of (S)-3-(4-(2-(4-((S)-2-(butyryloxy)-3-chloropropoxy)phenyl)propan-2-yl)phenoxy)propane-1,2-diyl dibutyrate.

Example 18

Synthesis of 1-methoxy-3-(4-(2-(4-(oxiran-2-yl-methoxy)phenyl)propan-2-yl)phenoxy)propan-2-ol

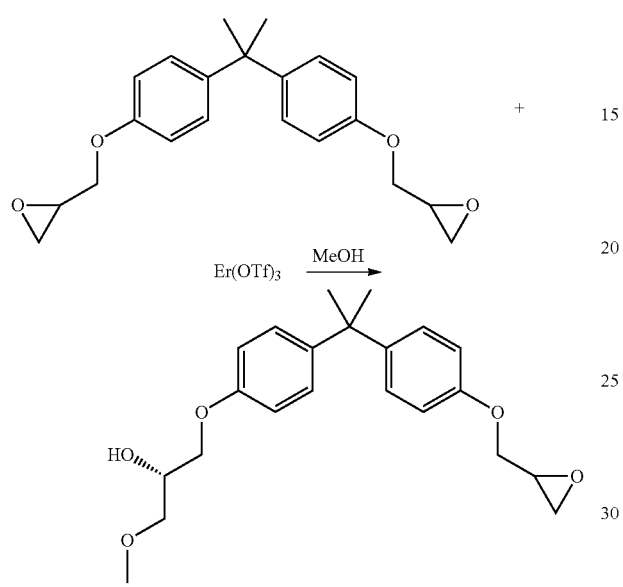

To a solution of racemic derivative Bisphenol A diglycidyl ether (500 mg, 1.46 mmol, 1 equiv) in methanol (5 mL) was added solid Erbium(III) trifluoromethanesulfonate (90 mg, 0.146 mmol, 1/10 equiv) in one portion and the mixture was stirred at room temperature for 1 h. Sodium bicarbonate was added (1 mL), the organic solvent was evaporated under reduced pressure and the residue was extracted with dichloromethane (3×5 mL). The organic layer was washed with deionized water (2×5 mL), was dried over anhydrous magnesium sulfate, was filtered, and was concentrated under reduced pressure. The resulting residue was purified by flash column chromatography on silica gel (eluent: 10% to 40% ethyl acetate in hexane) to provide the title compound (128 mg, 23%) as a pale foam.

Example 19

Synthesis of 1-chloro-3 (4-(2-(4-(2 hydroxy-3-methoxypropoxy)phenyl)propan-2-yl)phenoxy)propan-2-ol

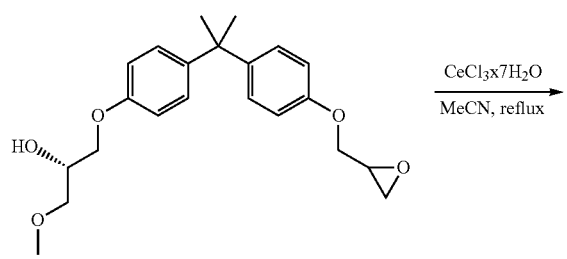

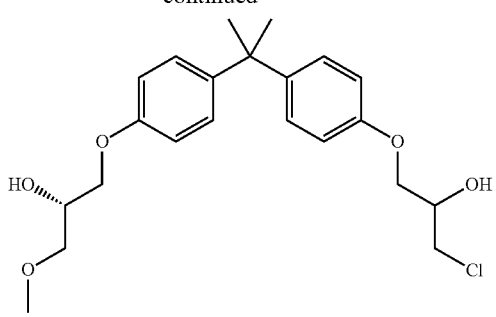

To a solution of racemic derivative 1-methoxy-3-(4-(2-(4-(oxiran-2-ylmethoxy)phenyl)propan-2-yl)phenoxy)propan-2-ol (64 mg, 0.17 mmol, 1 equiv) in acetonitrile (2 mL) was added CeCl$_3$.7H$_2$O (96 mg, 0.25 mmol, 1.5 equiv) and the mixture was refluxed for 17 h. The resulting white paste was filtered and washed with ethyl acetate and the clear suspension was concentrated under reduced pressure. The resulting residue was purified by flash column chromatography on silica gel (eluent: 40% ethyl acetate in hexane) to provide the title compound (70 mg, 99%) as a pale foam.

Example 20

Synthesis of 1-chloro-3 (4-(2-(4-(2-hydroxy-3-methoxypropoxy)phenyl)propan-2-yl)phenoxy)propan-2-ol bispropionate

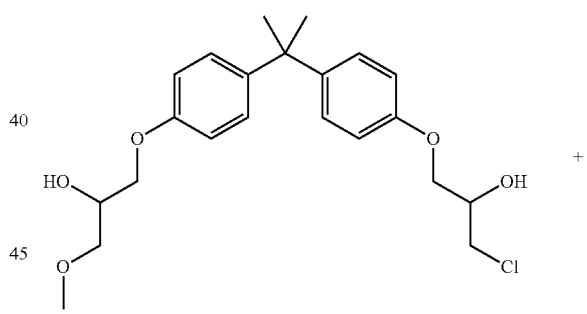

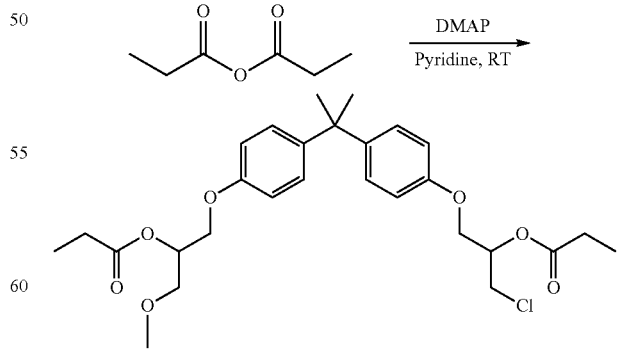

Prepared as described in Example 17 for (S)-3-(4-(2-(4-((S)-3-chloro-2-(propionyloxy)propoxy)phenyl)propan-2-yl)phenoxy)propane-1,2-diyl dipropionate.

Figure 14A:
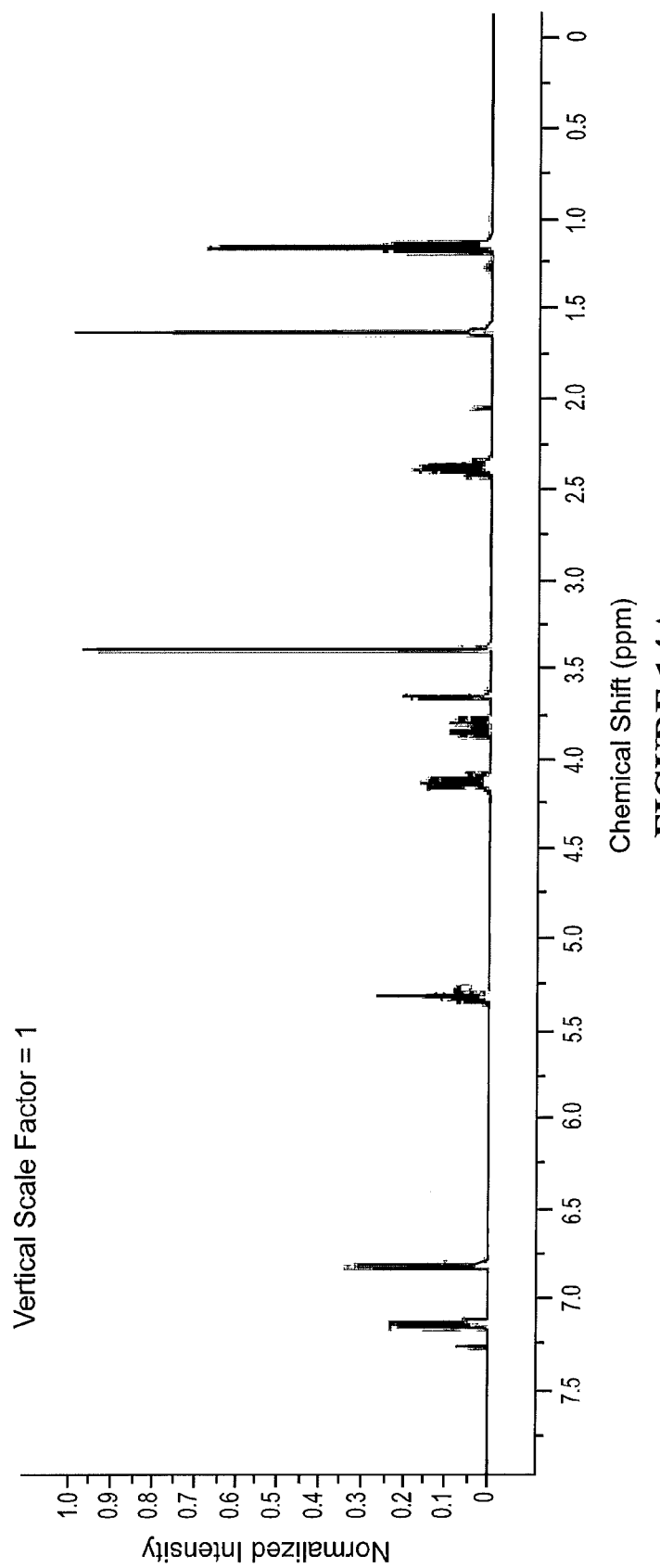
FIG. 14A is a $^1$H NMR spectrum for the compound 1-chloro-3-(4-(2-(4-(2-hydroxy-3-methoxypropoxy)phenyl)propan-2-yl)phenoxy)propan-2-ol bispropionate.
Figure 14B:
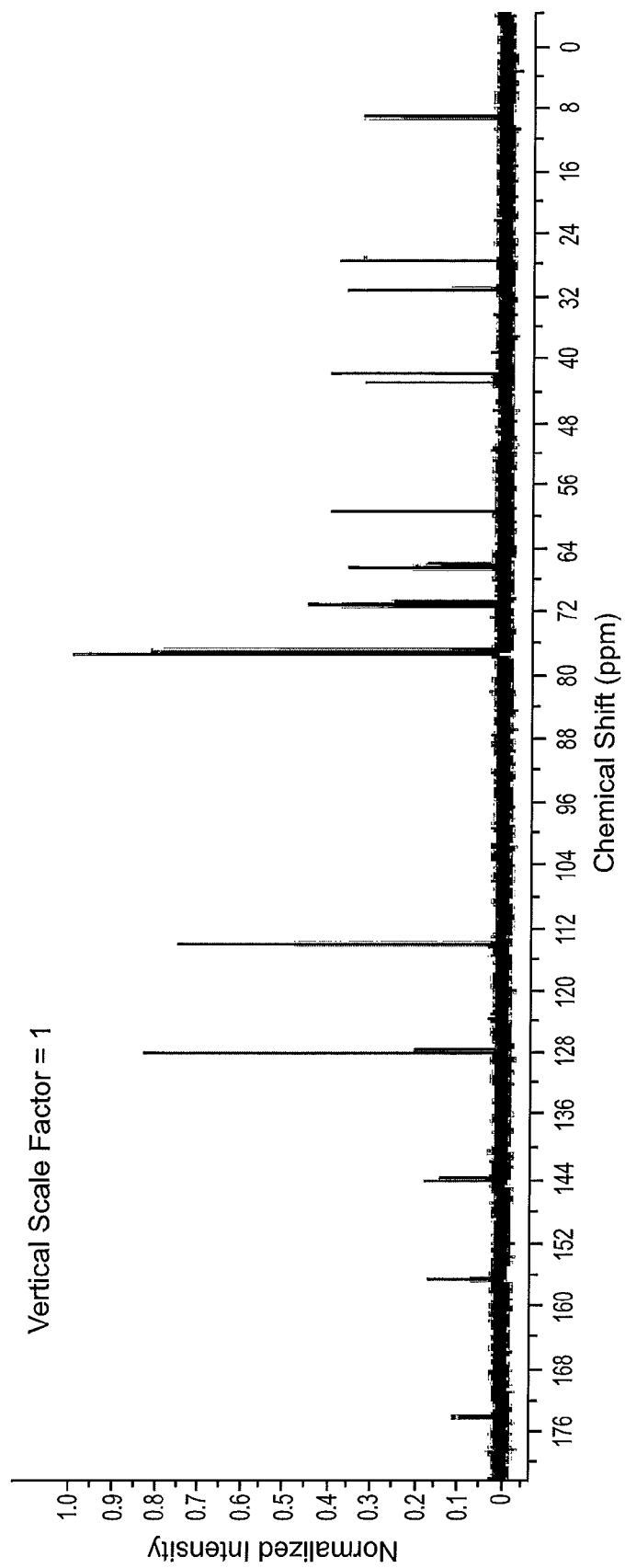
FIG. 14B is a $^{13}$C NMR spectrum for the compound 1-chloro-3-(4-(2-(4-(2-hydroxy-3-methoxypropoxy)phenyl)propan-2-yl)phenoxy)propan-2-ol bispropionate.

FIGS. 14A and 14B are $^1$H and $^{13}$C NMR spectra of 1-chloro-3-(4-(2-(4-(2-hydroxy-3-methoxypropoxy)phenyl)propan-2-yl)phenoxy)propan-2-ol bispropionate.

Example 21

Synthesis of (S)-1-(4-(2-(4-((S)-2-acetoxy-3-chloropropoxy)phenyl)propan-2-yl)phenoxy)-3-methoxypropan-2-yl acetate

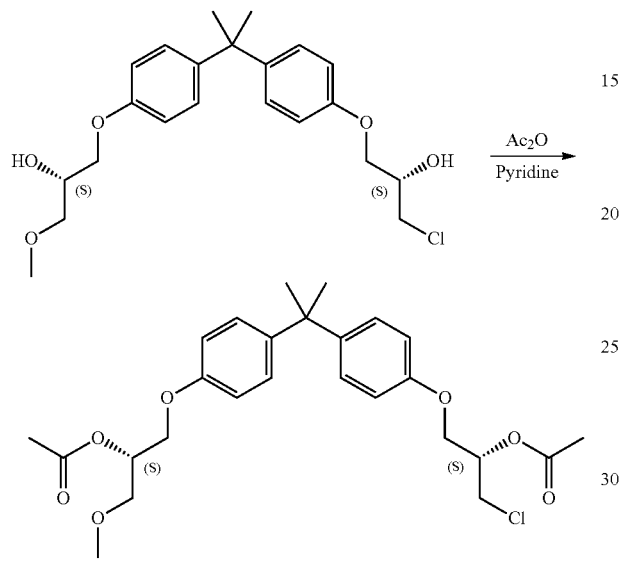

To a solution of (S)-1-chloro-3-(4-(2-(4-((S)-2-hydroxy-3-methoxypropoxy)phenyl)propan-2-yl)phenoxy)propan-2-ol (15 mg, 0.036 mmol) in anhydrous pyridine (1.0 ml) were successively added acetic anhydride (9 µL, 0.091 mmol) and catalytic amount of DMAP. After 5 h, the reaction mixture was quenched with an aqueous solution of sodium chloride and stirred for 15 min, and the resulting mixture was extracted twice with dichloromethane. The organic phases were combined, dried over anhydrous magnesium sulfate, and filtered. Solvents were evaporated, and the resulting crude material was purified by silica gel flash chromatography (eluent: 10 to 20% ethyl acetate in hexane) to provide the title compound as a sticky solid.

Figure 7A:
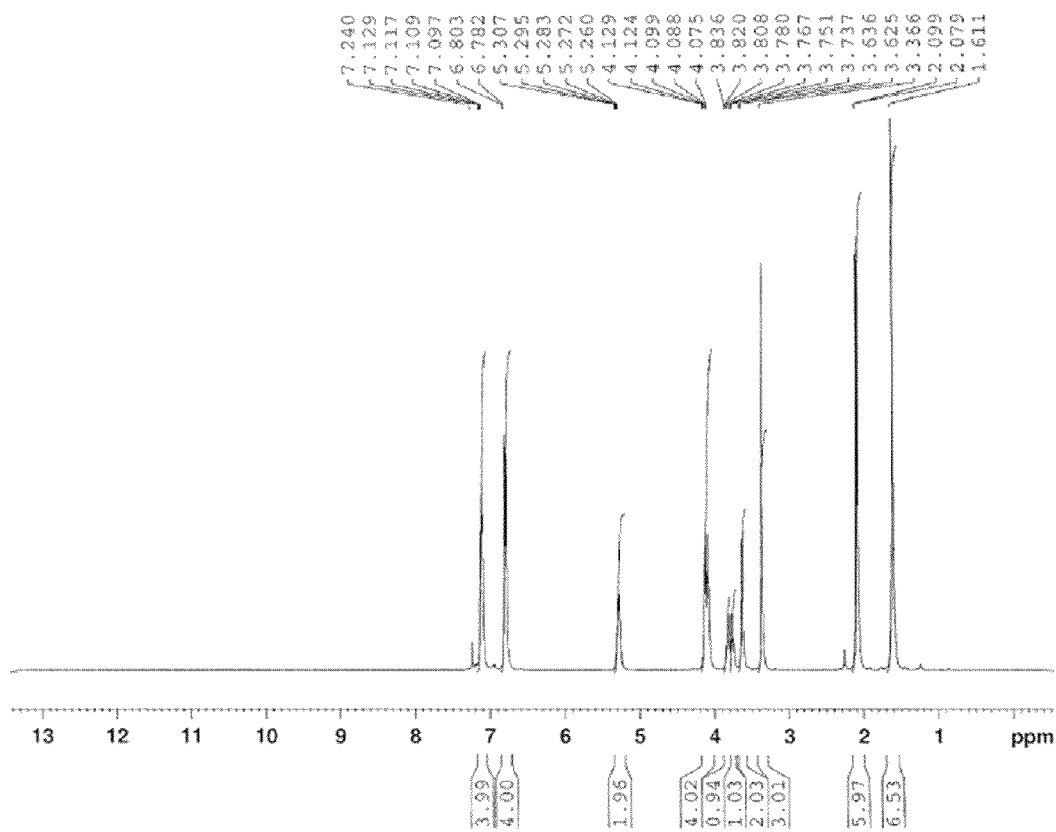
FIG. 7A is a $^1$H NMR spectrum for the compound (S)-1-(4-(2-(4-((S)-2-acetoxy-3-chloropropoxy)phenyl)propan-2-yl)phenoxy)-3-methoxypropan-2-yl acetate.
Figure 7B:
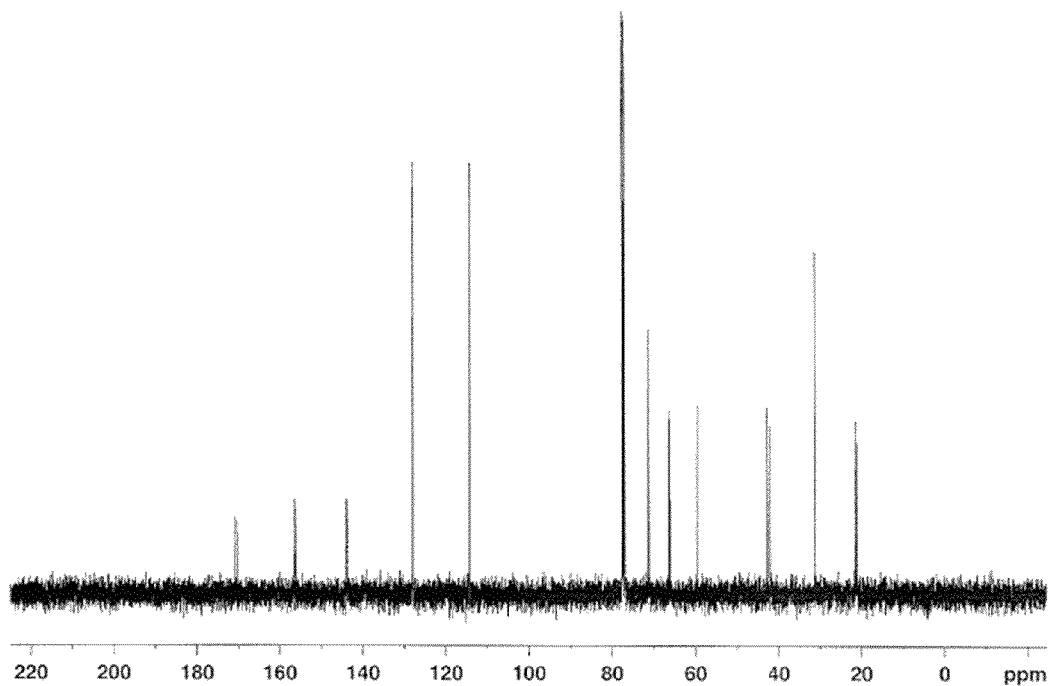
FIG. 7B is a $^{13}$C NMR spectrum for the compound (S)-1-(4-(2-(4-((S)-2-acetoxy-3-chloropropoxy)phenyl)propan-2-yl)phenoxy)-3-methoxypropan-2-yl acetate.
Figure 7C:
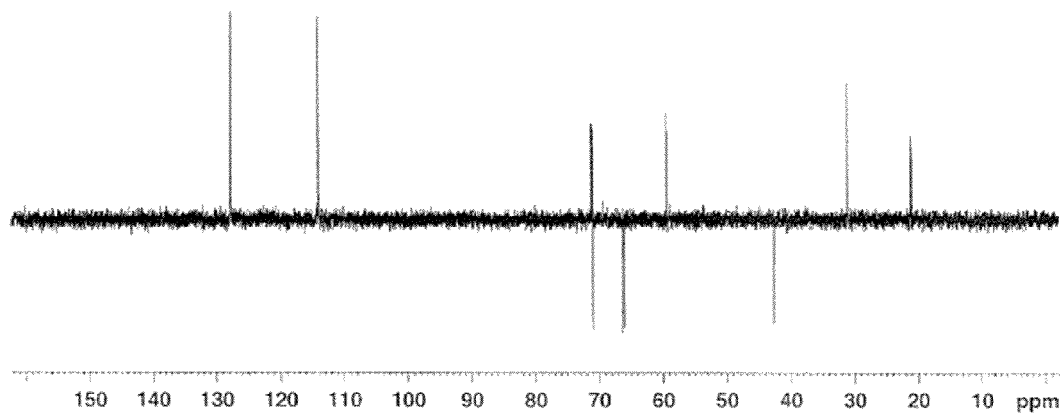
FIG. 7C is a $^{13}$C APT NMR spectrum for the compound (S)-1-(4-(2-(4-((S)-2-acetoxy-3-chloropropoxy)phenyl)propan-2-yl)phenoxy)-3-methoxypropan-2-yl acetate
Figure 7D:
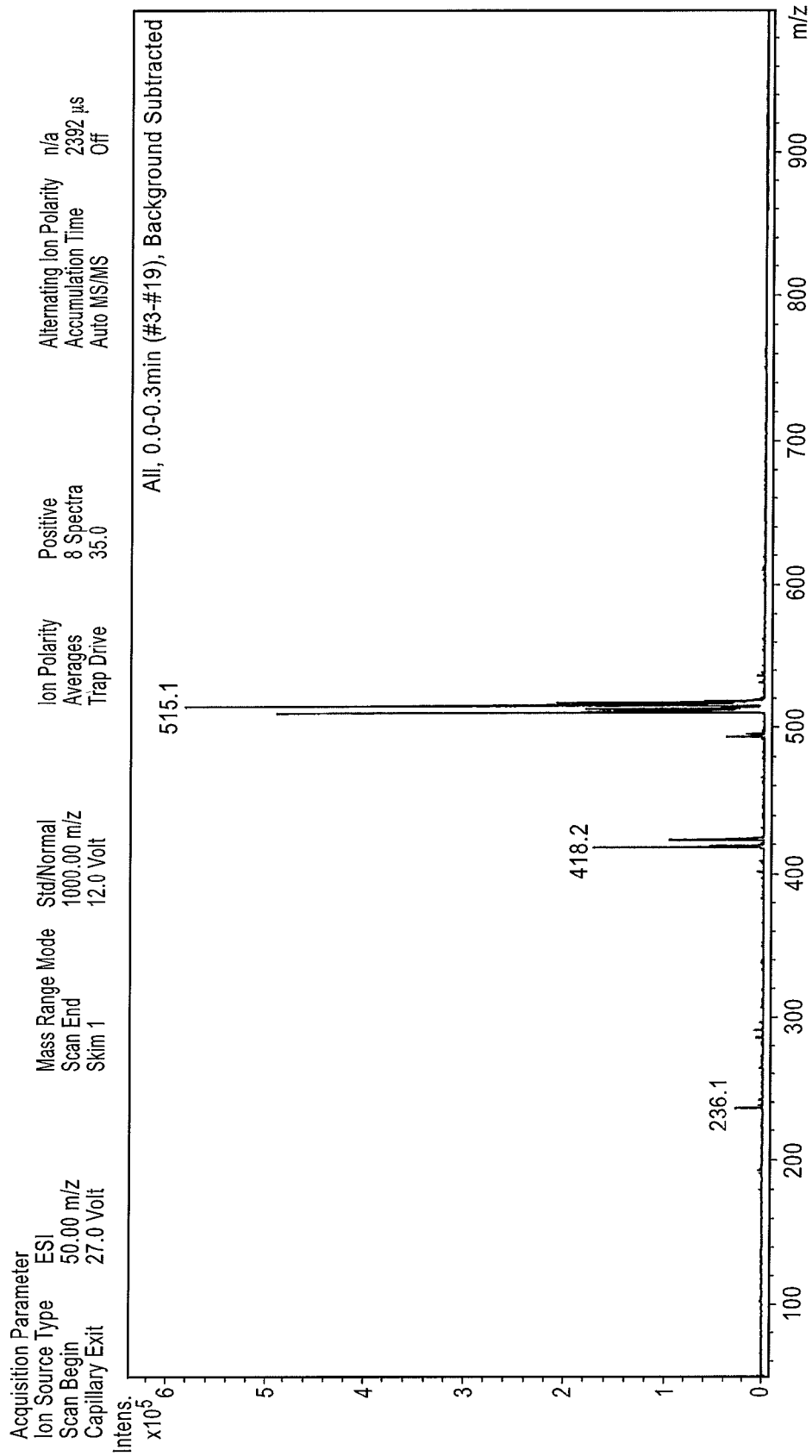
FIG. 7D illustrates electrospray ionization mass spectrometry data for (S)-1-(4-(2-(4-((S)-2-acetoxy-3-chloropropoxy) phenyl)propan-2-yl)phenoxy)-3-methoxypropan-2-yl acetate with positive ion polarity.
Figure 7E:
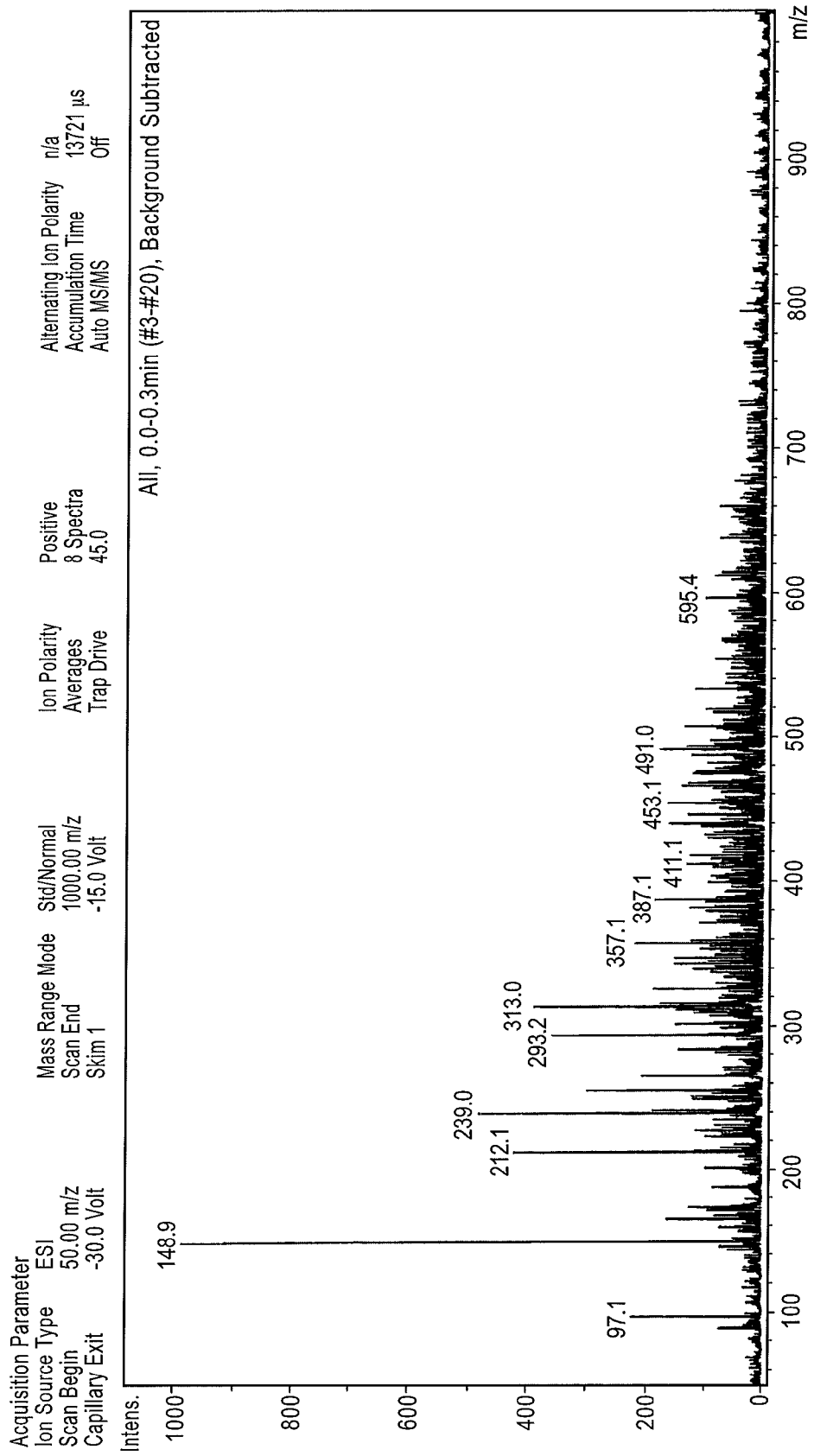
FIG. 7E illustrates electrospray ionization mass spectrometry data for (S)-1-(4-(2-(4-((S)-2-acetoxy-3-chloropropoxy) phenyl)propan-2-yl)phenoxy)-3-methoxypropan-2-yl acetate with negative ion polarity.

FIGS. 7(A)-(C) are $^1$H, $^{13}$C and $^{13}$C APT NMR spectra for the title compound (S)-1-(4-(2-(4-((S)-2-acetoxy-3-chloropropoxy)phenyl)propan-2-yl)phenoxy)-3-methoxypropan-2-yl acetate.

FIGS. 6(D) and (E) are ESI MS spectrographs for (S)-1-(4-(2-(4-((S)-2-acetoxy-3-chloropropoxy)phenyl)propan-2-yl)phenoxy)-3-methoxypropan-2-yl acetate.

In Vitro Activity of Compounds

Example 22

LNCaP (2.4×10$^4$ cell/well) cells were seeded on 24-well plates overnight before transfection with PSA (6.1 kb)-luciferase plasmid (0.25 ug/well) in serum-free, red phenol-free media. The next day, cells were pre-treated with compounds of the disclosure for 1 hour before the addition of synthetic androgen, R1881 (1 nM) to trans activate the androgen receptor. After 48 h of incubation with R1881, the cells were harvested, and relative luciferase activity was determined as a read-out for androgen receptor transcriptional activity. Test compounds were added to the cells at various concentrations and activity for each treatment was normalized to the predicted maximal activity induction (in the absence of test compounds, vehicle only). Transfection experiments were performed using triplicate wells.

Figure 8:
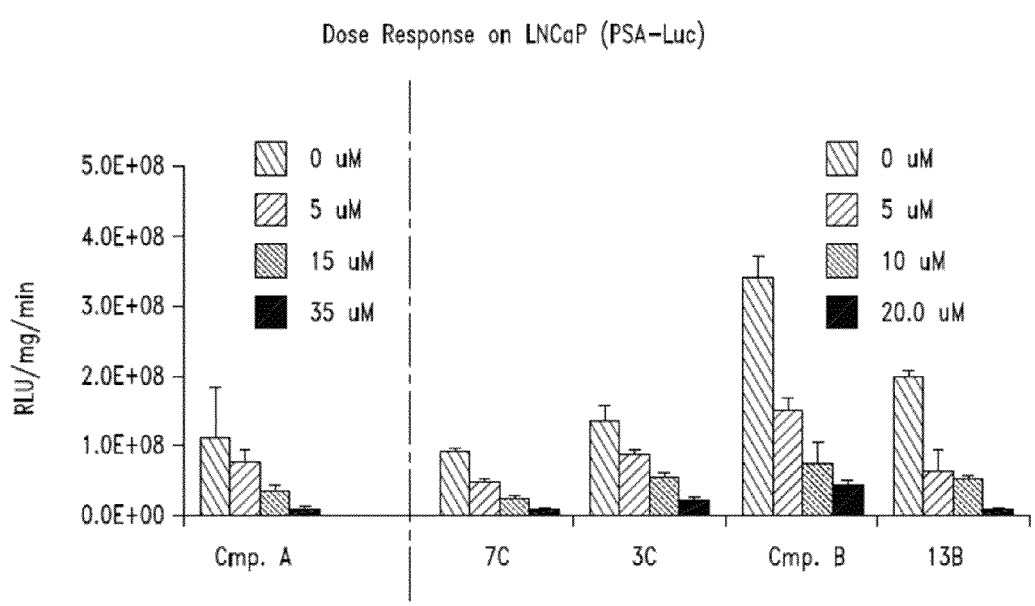
FIG. 8 illustrates dose response data for various compounds of the disclosure (3c, 7c, and 13b) and comparative compounds.

FIG. 8 presents in vitro dose response of various compounds of the disclosure (7c, 3c and 13b) relative to comparative compounds A and B.

As seen in FIG. 8, each of the tested compounds of the disclosure showed a dose response.

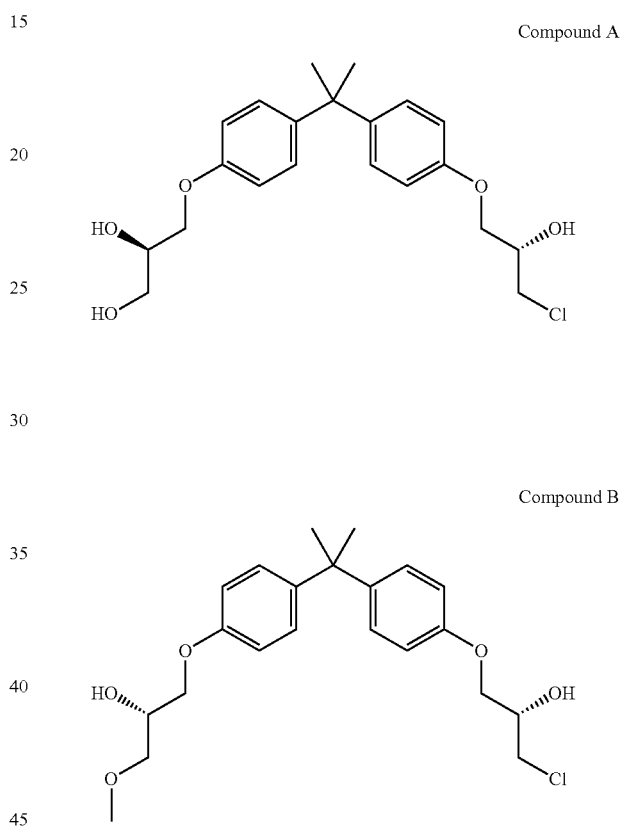

Furthermore, toxicity was assessed by both microscopic examination and reduction of protein levels. Solubility was assessed both macroscopically (cloudy media) and microscopically (formation of granules or crystals).

Thus, tested compounds

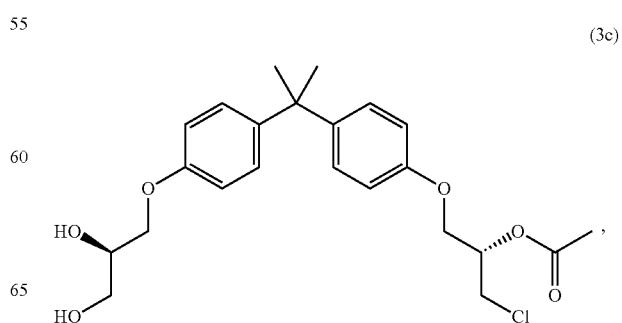

(7c)

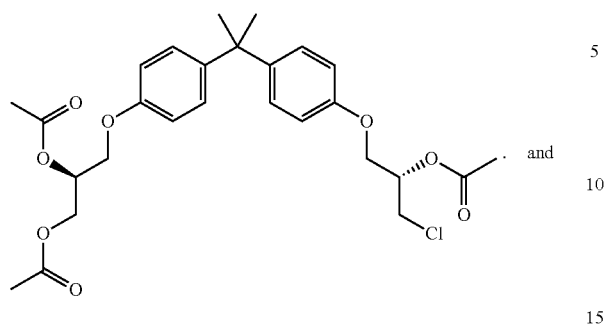

(13b)

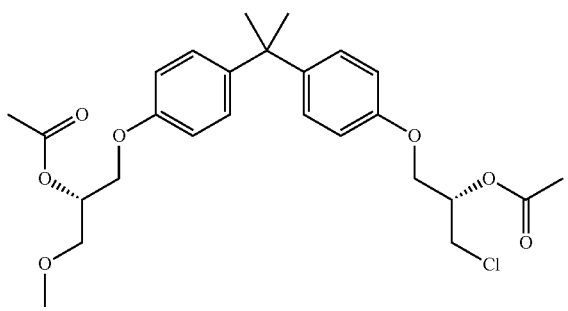

are effective in the treatment methods disclosed herein and demonstrated a dose response at 5 µM, 10 µM, and 20 µM.

Example 23

Further experiments, as outlined in Example 22, were conducted with LNCaP cells transfected with PSA-luciferase plasmid to evaluate the dose response of particular compounds of the disclosure.

The compounds of the disclosure were compared to compounds A and B, as in

Example 22

Compound A

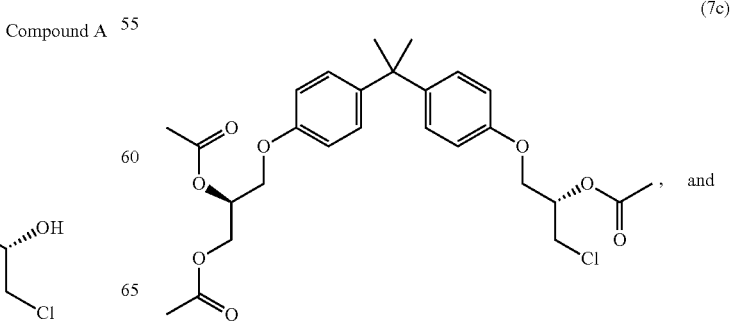

Compound B

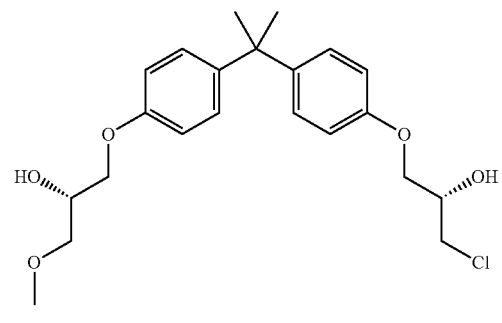 [SMILES: COCC(O)COc1ccc(C(C)(C)c2ccc(OCC(O)CCl)cc2)cc1]

The compounds of the disclosure evaluated were as follows:

(1c)

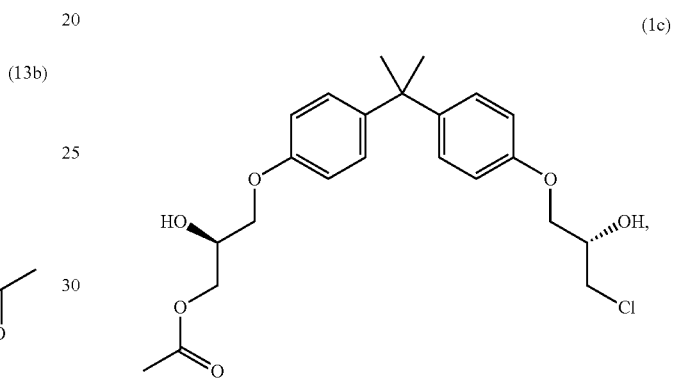

(3c)

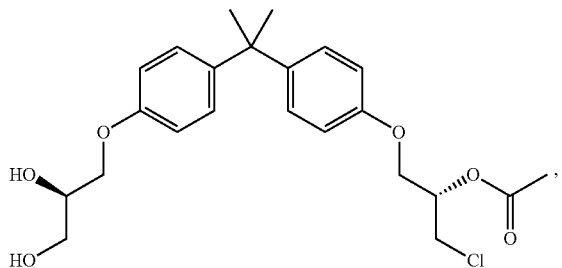

(7c)

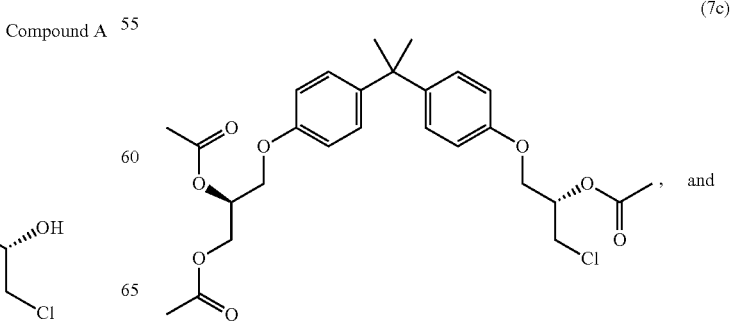

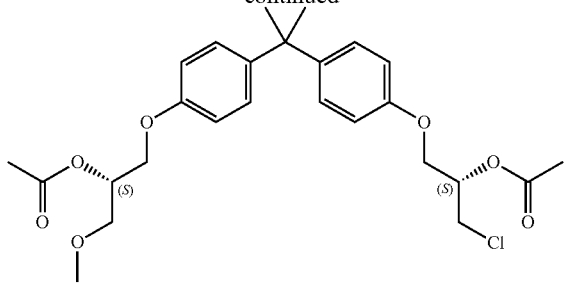

(S)-1-(4-(2-(4-((S)-2-acetoxy-3-chloropropoxy)phenyl)propan-2-yl)phenoxy)-3-methoxypropan-2-yl acetate (Example 21)

Figure 9:
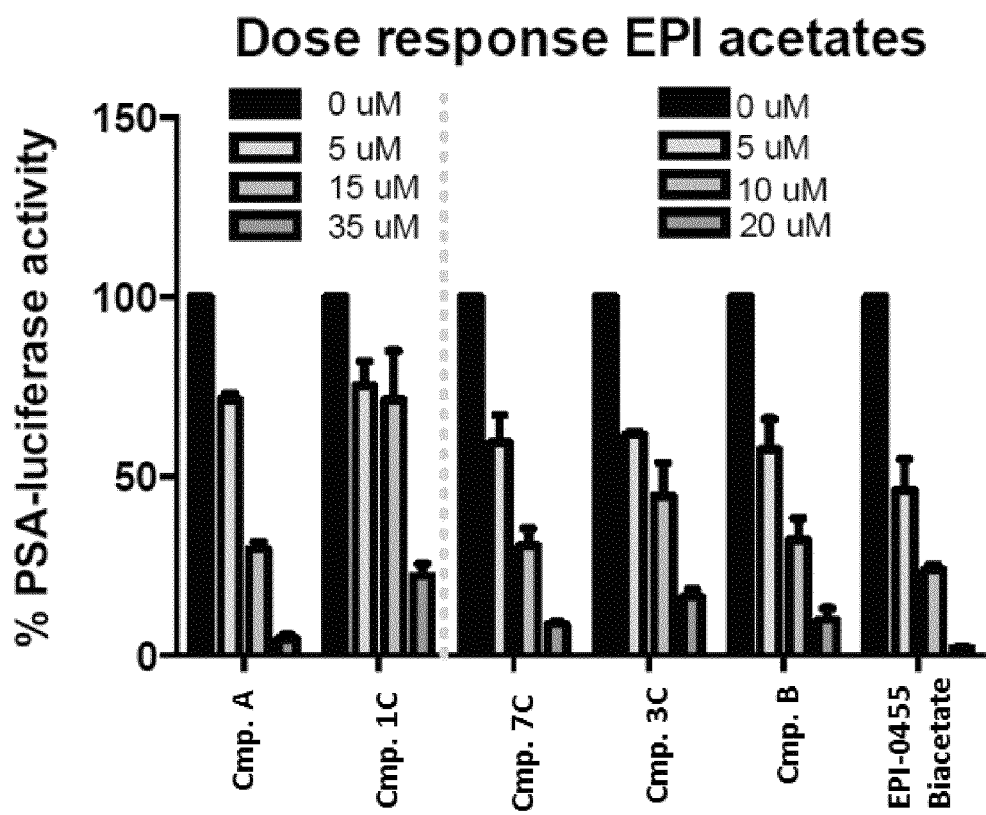
FIG. 9 illustrates dose response data for various compounds of the disclosure (1c, 3c, 7c, (S)-1-(4-(2-(4-((S)-2-acetoxy-3-chloropropoxy)phenyl)propan-2-yl)phenoxy)-3-methoxypropan-2-yl acetate (Example 21)) and comparative compounds.

FIG. 9 presents in vitro dose response of various compounds of the disclosure (1c, 3c 7c, and (S)-1-(4-(2-(4-((S)-2-acetoxy-3-chloropropoxy)phenyl)propan-2-yl)phenoxy)-3-methoxypropan-2-yl acetate (Example 21)) relative to comparative compounds A and B.

The following Table 4 also illustrates the data contained in FIG. 9 and demonstrates that the compounds of the disclosure exhibit a dose response.

TABLE 4

| Analog | IC50 (μM + Standard Deviation) |
|---|---|
| Compound A | 15.02 + 1.25 |
| Compound 1C | 25.58 + 6.89 |
| Compound 3C | 11.61 + 2.6 |
| Compound 7C | 8.81 + 0.93 |
| Compound B | 9.80 + 2.28 |
| (S)-1-(4-(2-(4-((S)-2-acetoxy-3-chloropropoxy)phenyl)propan-2-yl)phenoxy)-3-methoxypropan-2-yl acetate (Example 21) | 8.07 + 1.48 |

Example 24

Viability and proliferation assays were conducted and demonstrate that a prodrug compound of the disclosure is twice as potent as its active compound.

A compound of the disclosure:

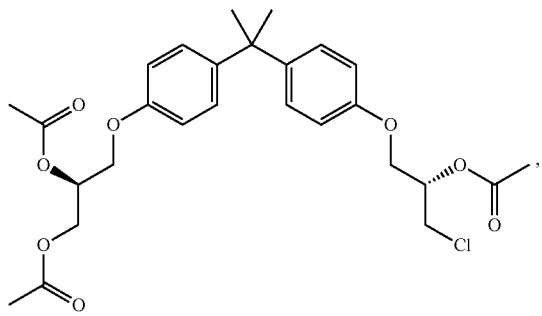 [SMILES: CC(=O)OC[C@H](COc1ccc(C(C)(C)c2ccc(OC[C@@H](CCl)OC(C)=O)cc2)cc1)OC(C)=O]

(7c)

was compared to compound A:

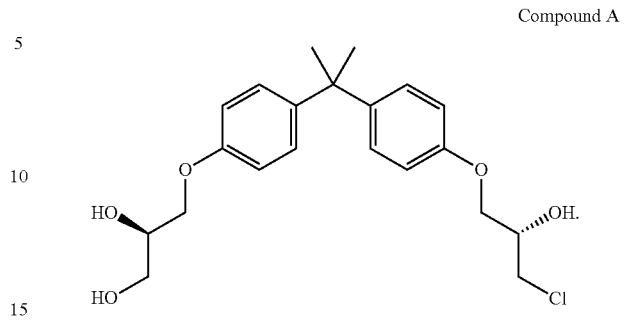

Compound A

Protocol: Proliferation assays using AlamarBlue, wherein the % androgen-dependent proliferation represents proliferation of LNCaP cells in response to R1881 compared to basal levels. PC3 cells do not express functional androgen receptor and % viability provides an indication of cytotoxicity or off-target effects unrelated to the androgen receptor.

Viability and proliferation assays. PC3 and LNCaP cells were plated in 96-well plates in respective media plus 0.5% FBS. The next day, PC3 cells were treated with vehicle and increasing concentrations of Compound A or Compound 7c for 2 days, and LNCaP cells were pretreated with vehicle and Compound A for 1 hour before treating with 0.1 nM R1881 for 3 days. Cell viability was measured using alamarBlue Cell Viability Assay (Invitrogen) following the manufacturer's protocol.

Figure 10:
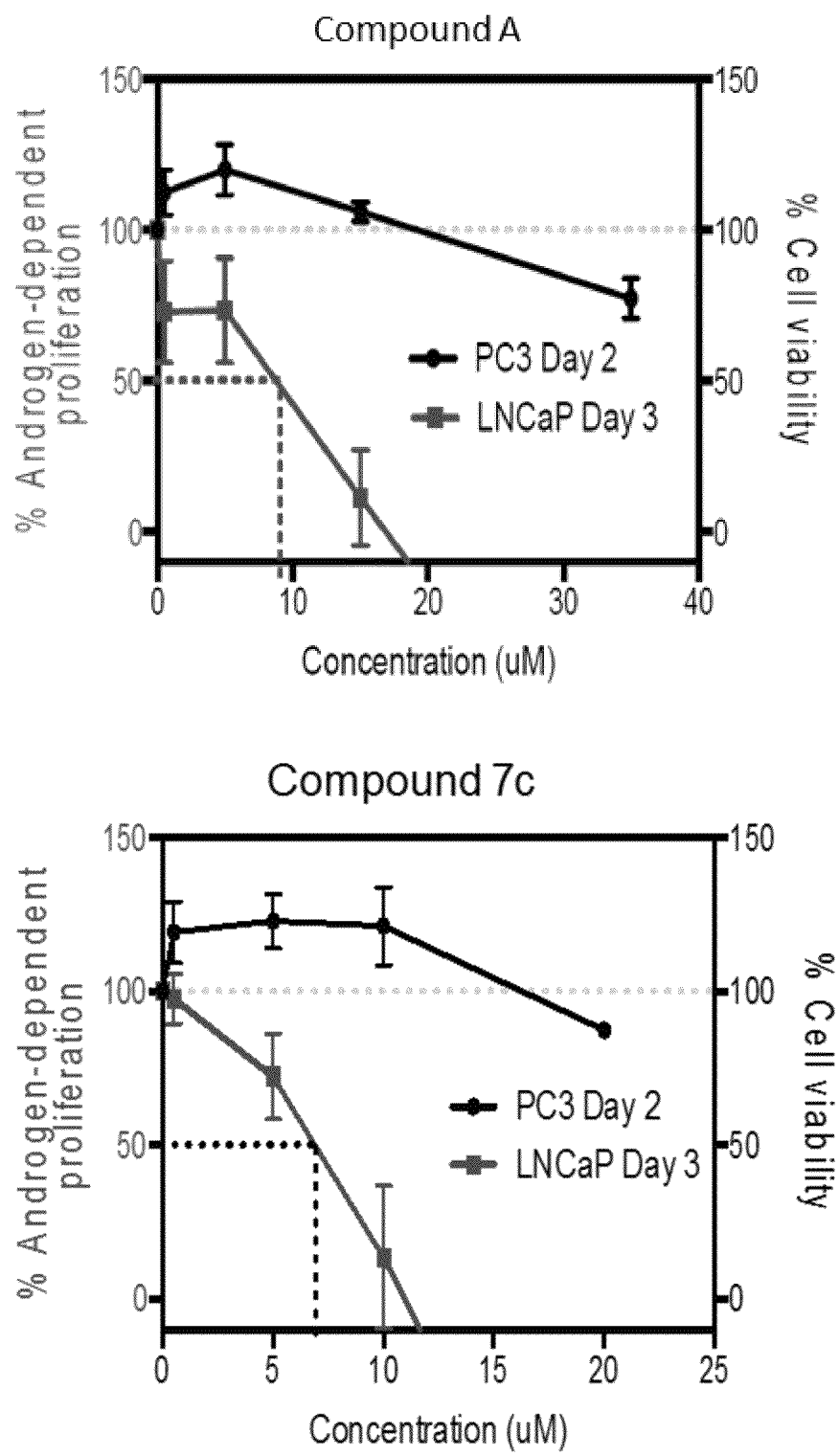
FIG. 10 depicts cell proliferation assays, which demonstrate that a compound (7c) of the disclosure is twice as potent as its active compound (compound A).

The results are illustrated in FIG. 10 and demonstrate that a prodrug compound of the disclosure (i.e. 7c) is twice as potent as its active compound (i.e. compound A).

Example 25

Xenograft Experiment

Male NOD-SCID mice bearing subcutaneous tumors were castrated when tumor volume was approximately 100 mm3

Animals bearing LNCaP xenografts were dosed daily by oral gavage with Compound 7c, Compound A, or 10% DMSO/corn oil vehicle control.

Tumors were measured using caliphers and the volume calculated by application of the formula (L×W×H)*0.5236.

Figure 11:
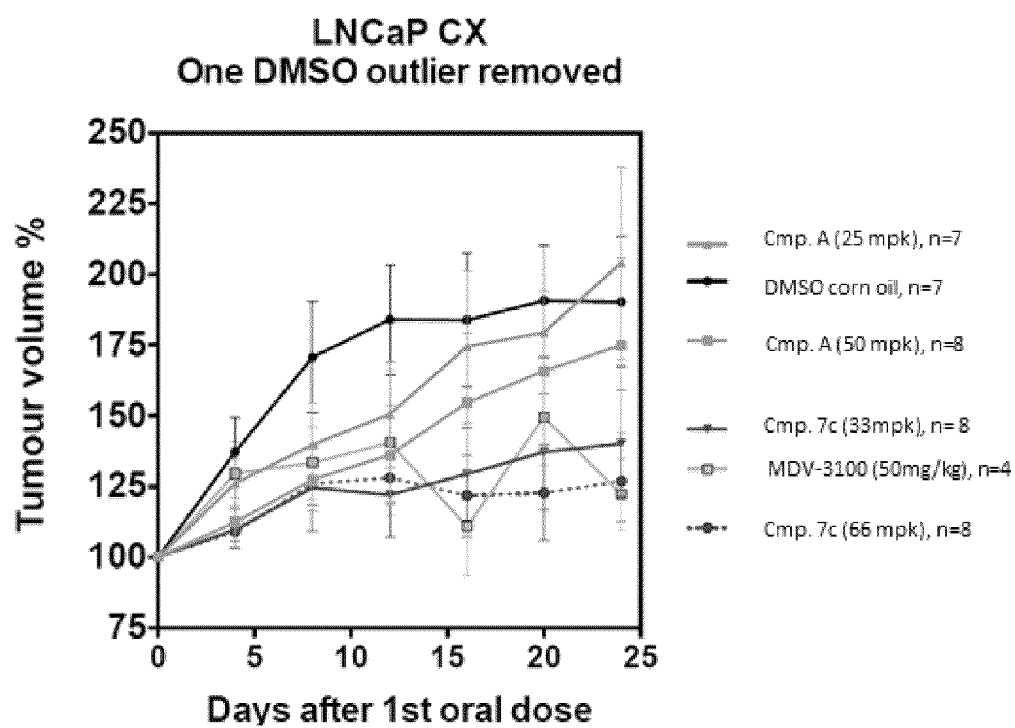
FIG. 11 illustrates that a compound of the disclosure (7c) is effective at reducing tumor volume in a xenograft model.

As can be seen from FIG. 11, a compound of the disclosure (i.e. compound 7c) is effective at reducing tumor volume.

Further, FIG. 11 demonstrates that a prodrug compound of the disclosure (i.e. compound 7c) is more effective than its active compound (i.e. compound A) at reducing tumor volume in the xenograft mouse model.

Example 26

Further Xenograft Experiment

Male NOD-SCID mice bearing subcutaneous tumors were castrated when tumor volume was approximately 100 mm3

Animals bearing LNCaP xenografts were dosed daily by oral gavage with 55.23 mg/kg body weight of Compound 7c or CMC/10% DMSO/Tween-20 vehicle control.

Figure 12:
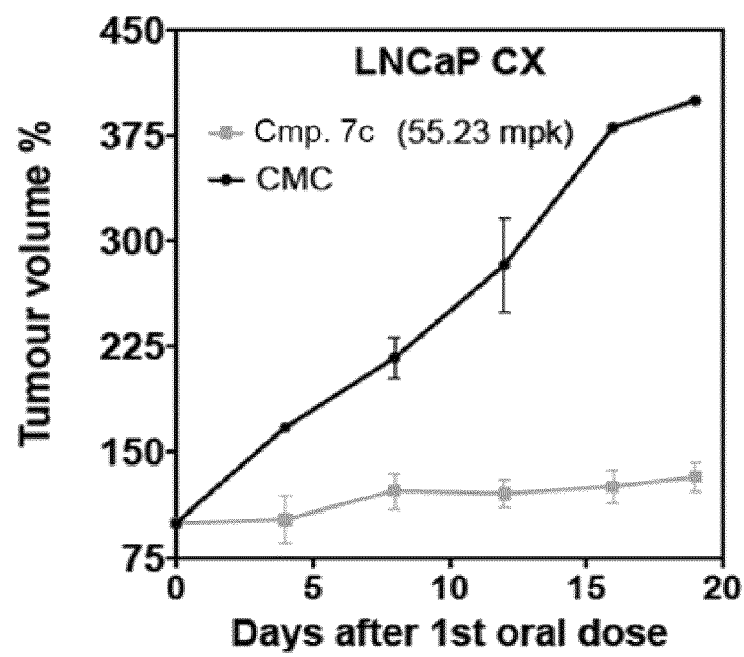
FIG. 12 illustrates that a compound of the disclosure (7c) is effective at inhibiting the growth of LNCaP xenograft tumors.

Tumors were measured using caliphers and the volume calculated by application of the formula (L×W×H)*0.5236 Male As can be seen from FIG. 12, a prodrug stereoisomer of a compound of the disclosure (i.e. compound 7c) is effective at reducing tumor volume.

Example 27

IC50's of Prodrugs of the Disclosure

Table 5 illustrates the IC50's of various prodrugs of the disclosure, as compared to Compound A.

Figure 13:
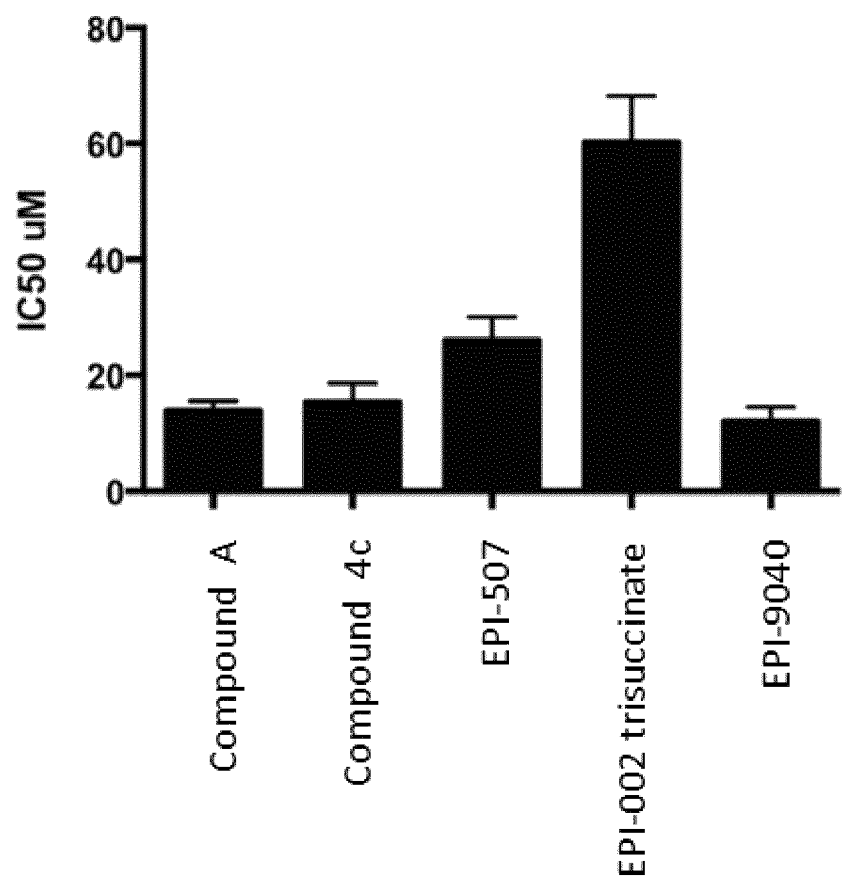
FIG. 13 illustrates the IC50's of various compounds of the disclosure.

FIG. 13 further illustrates the IC50's of various compounds of the disclosure.

TABLE 5

| COMPOUND | PSA-luc IC50s (uM) | | |
|---|---|---|---|
| | MEAN | SD | n |
| Compound A | 14.0 | 0.8 | 5 |
| Compound 4c | 15.3 | 3.4 | 4 |
| (S)-3-(4-(2-(4-((R)-oxiran-2-ylmethoxy)phenyl)propan-2-yl)phenoxy)propane-1,2-diyl diacetate | 26.0 | 4.1 | 4 |
| (S)-3-(4-(2-(4-((S)-3-chloro-2-hydroxypropoxy)phenyl)propan-2-yl)phenoxy)propane-1,2-diol trisuccinate | 60.2 | 8.1 | 2 |
| (S)-3-(4-(2-(4-((S)-3-chloro-2-hydroxypropoxy)phenyl)propan-2-yl)phenoxy)-2-hydroxypropyl 2-aminoacetate | 12.1 | 2.5 | 4 |

INCORPORATION BY REFERENCE

All of the U.S. patents, U.S. patent application publications, U.S. patent applications, foreign patents, foreign patent applications, and non-patent publications referred to in this specification and/or listed in the Application Data Sheet, are incorporated herein by reference, in their entirety for all purposes.

Aspects of the embodiments can be modified, if necessary, to employ concepts of the various patents, applications, and publications, incorporated by reference herein, to provide yet further embodiments. These and other changes can be made to the embodiments in light of the above-detailed description.

What is claimed is:

1. A compound having the following structure (Ic):

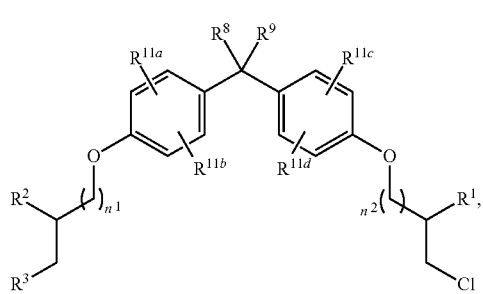

or a pharmaceutically acceptable salt, tautomer, or stereoisomer thereof, wherein:
$R^1$ is hydroxyl or —OC(=O)$R^{13}$;
$R^2$ is hydroxyl or —OC(=O)$R^{13}$;
$R^3$ is hydroxyl, halo, or —OC(=O)$R^{13}$;
wherein, halo is selected from the group consisting of F, Br, and I;
$R^8$ is methyl;
$R^9$ is methyl;
$R^{11a}$, $R^{11b}$, $R^{11c}$ and $R^{11d}$ are each independently H;
$R^{13}$ is $C_1$-$C_6$ alkyl;
$n^1$ and $n^2$ are each independently 1; and
wherein at least one of $R^1$, $R^2$, or $R^3$ is —OC(=O)$R^{13}$;
wherein $R^3$ is not —OC(=O)$CH_3$ when $R^1$ and $R^2$ are both hydroxyl;
wherein $R^1$ and $R^2$ are not both —OC(=O)CH=$CH_2$; and
wherein $R^1$ and $R^2$ are not both —OC(=O)C(CH$_1$)=CH$_2$.

2. The compound of claim 1, wherein $R^3$ is halo.

3. The compound of claim 1, wherein $R^3$ is fluoro.

4. The compound of claim 1, wherein each $R^{13}$ is independently methyl, ethyl or propyl.

5. The compound of claim 1, wherein each $R^{13}$ is methyl.

6. The compound of claim 1 selected from one or more of:

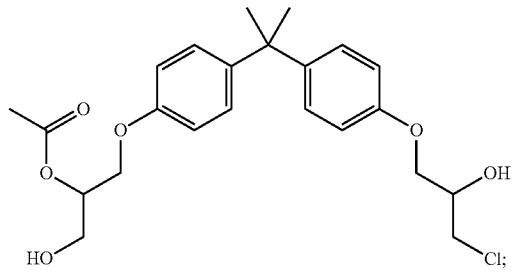

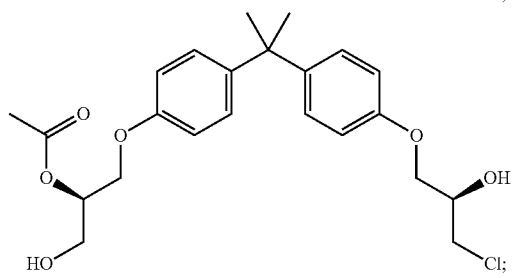

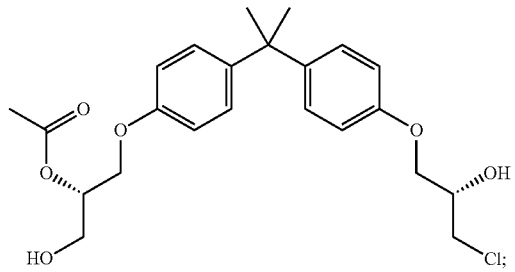

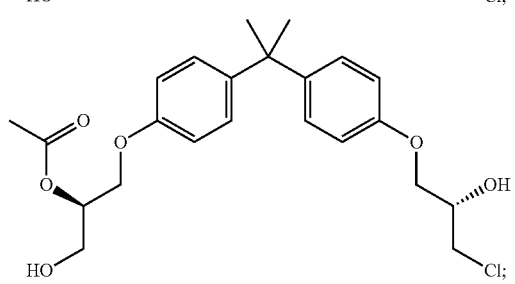

97
-continued
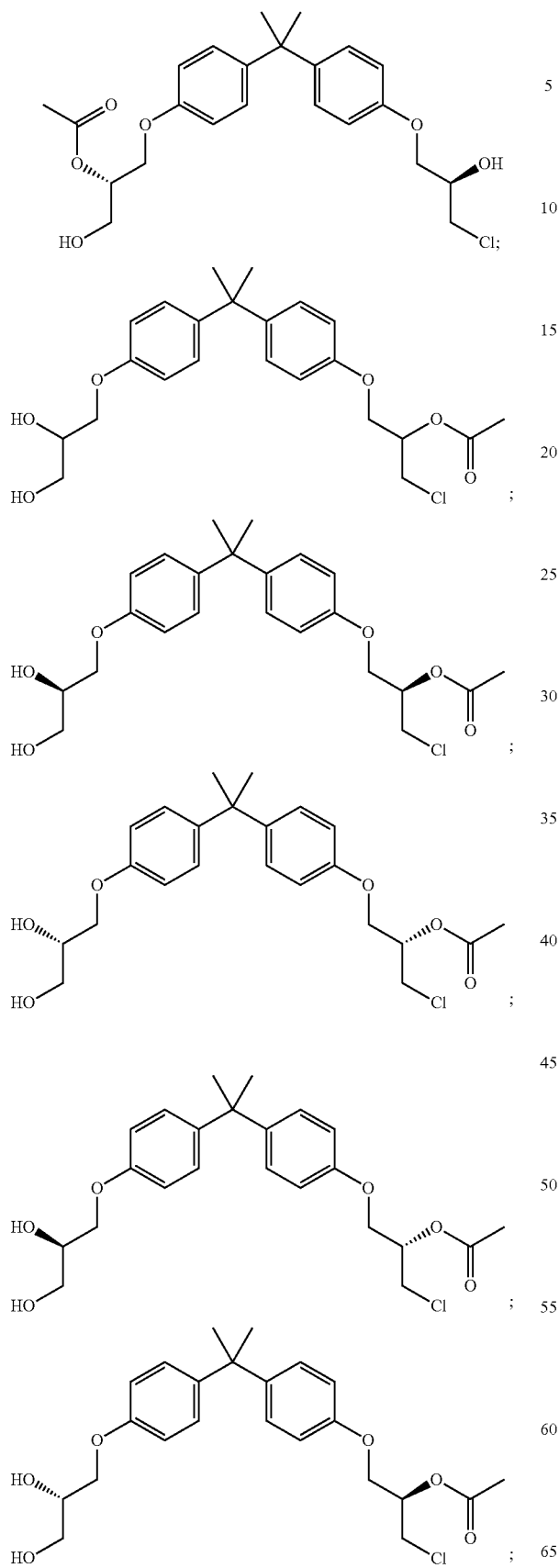
98
-continued
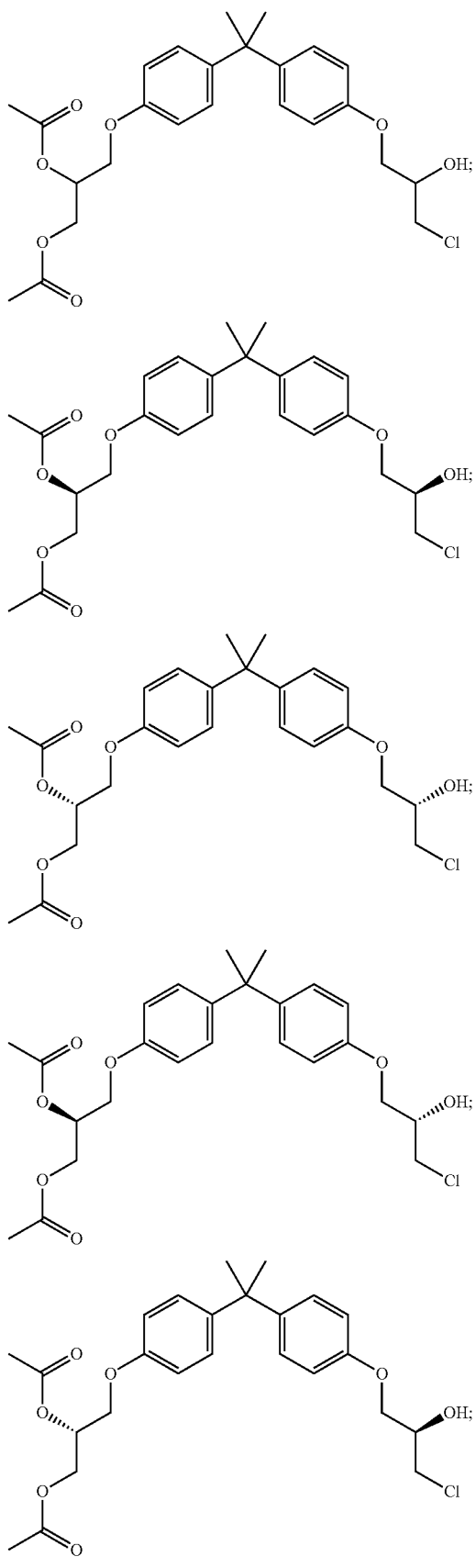

99
-continued
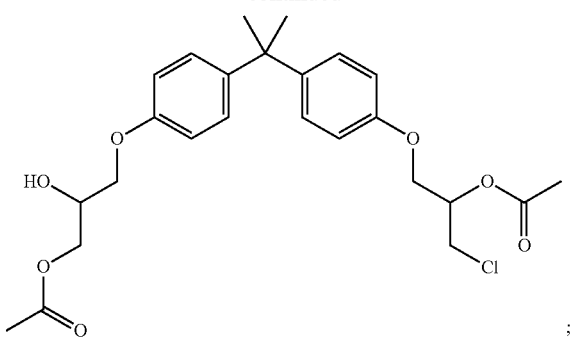
100
-continued
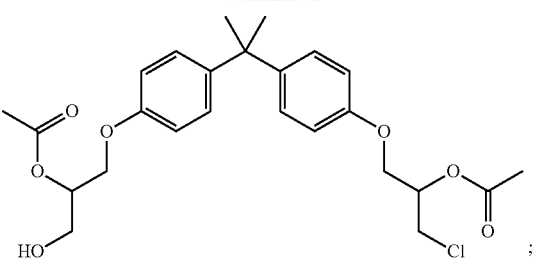
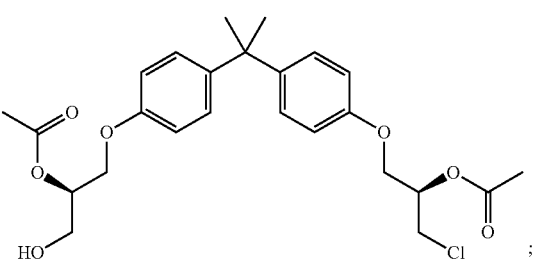
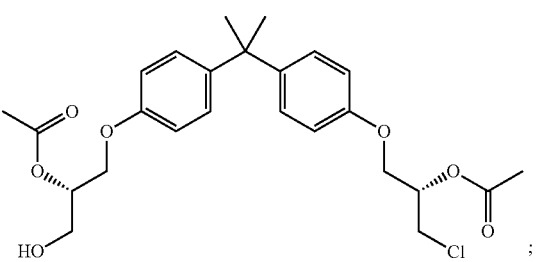
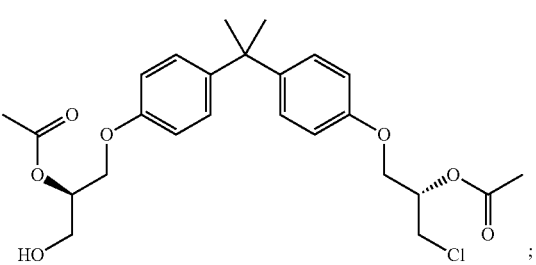
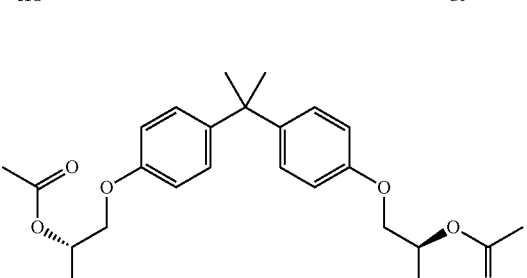
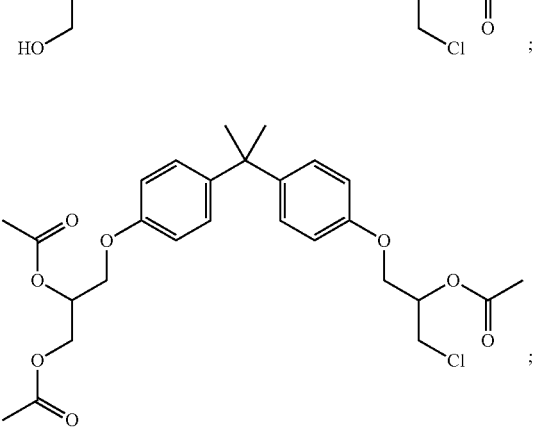

101
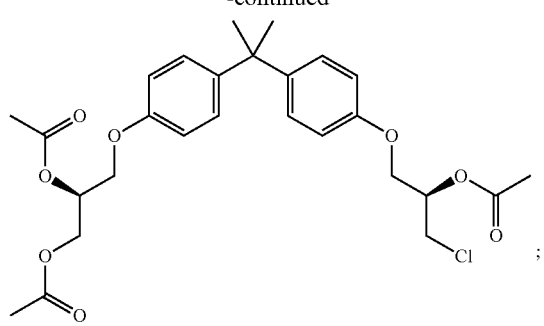
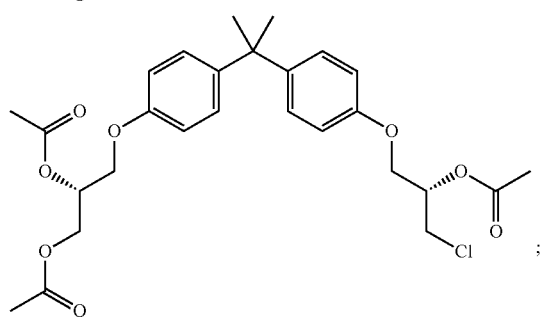
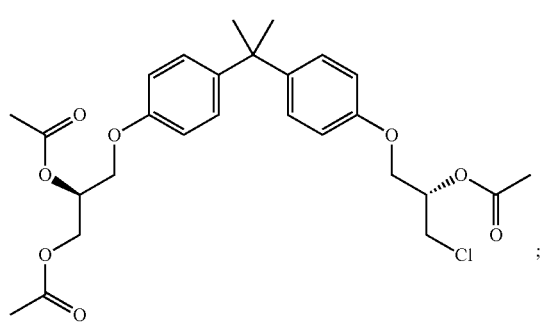 [SMILES: CC(=O)OC[C@H](COc1ccc(C(C)(C)c2ccc(OC[C@@H](CCl)OC(C)=O)cc2)cc1)OC(C)=O]
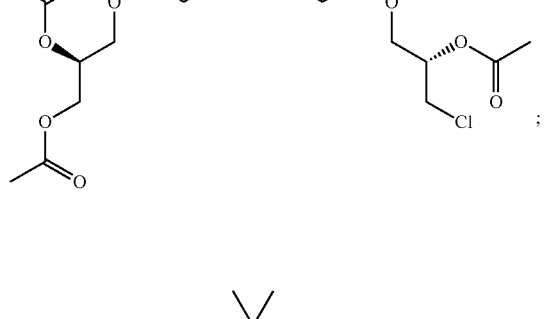
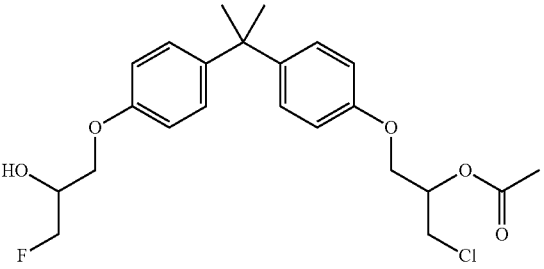
102
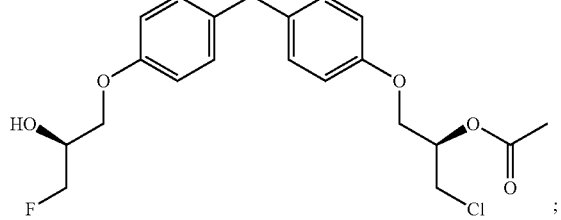
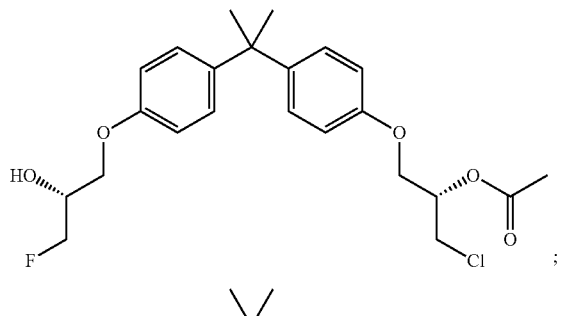
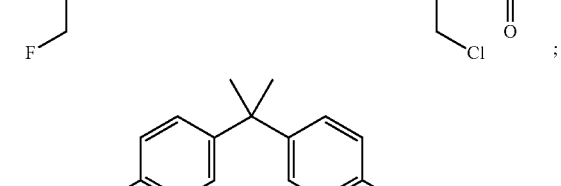
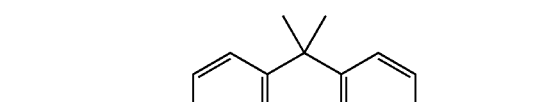
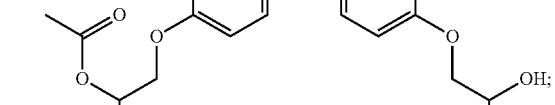
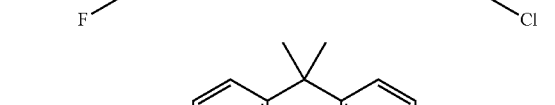
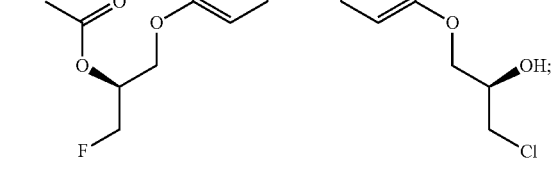

103
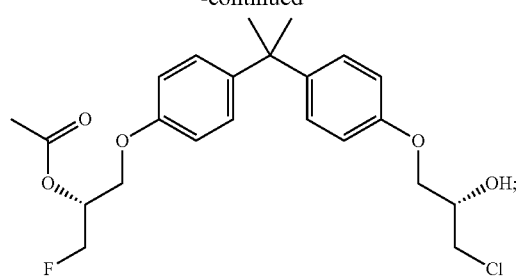
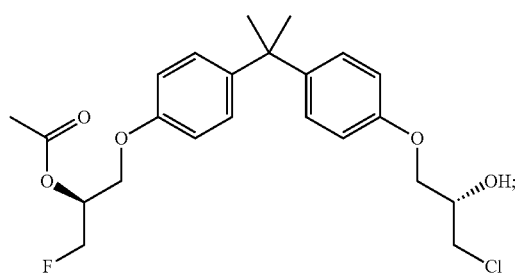
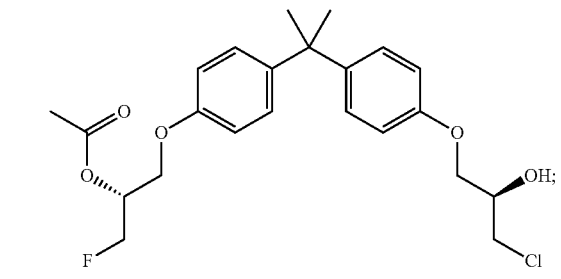
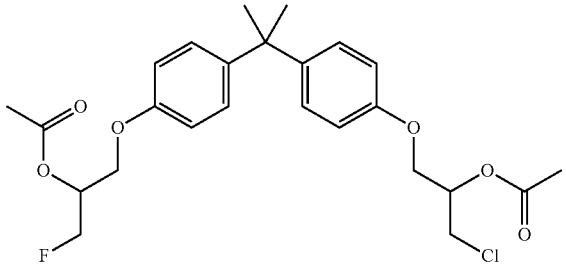
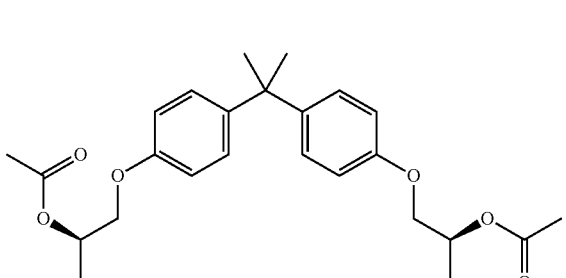
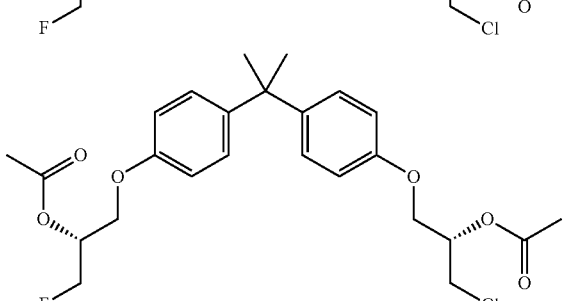
104
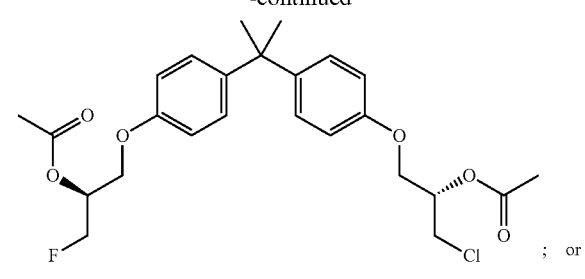
7. The compound of claim 1 selected from one or more of:
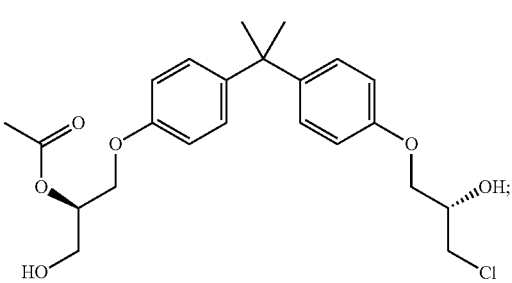
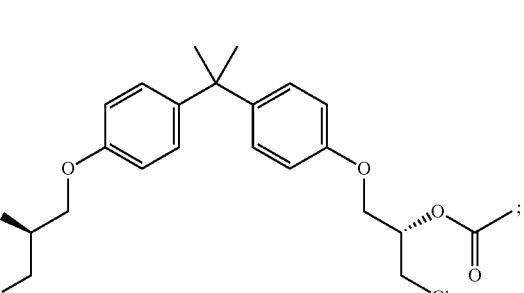
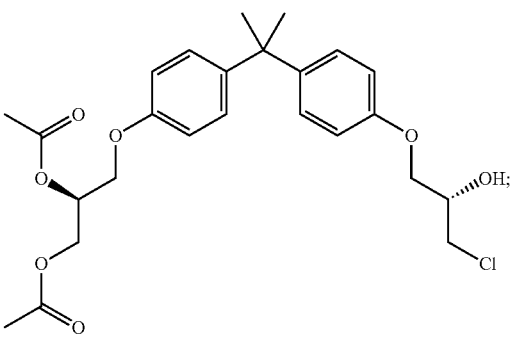

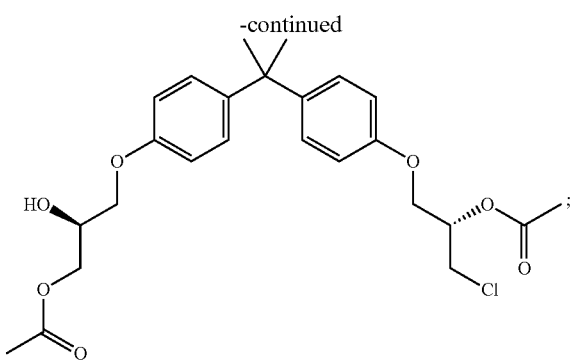

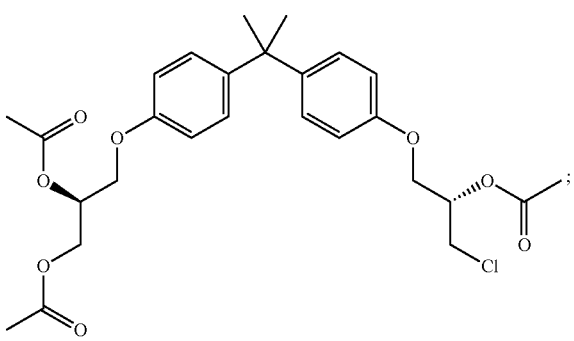

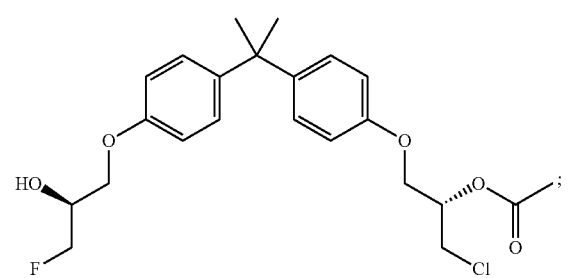

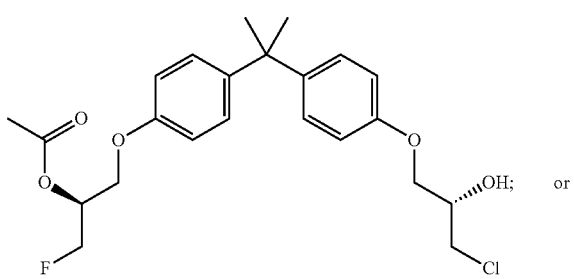

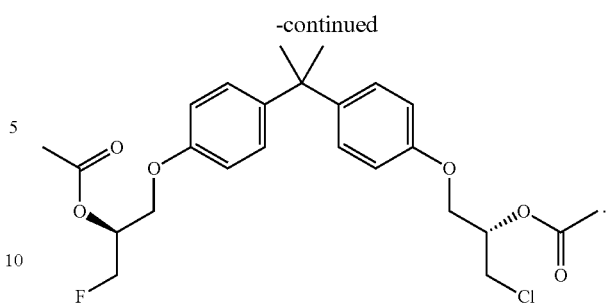

8. A pharmaceutical composition, comprising: a compound according to claim 1; and a pharmaceutically acceptable carrier.

9. A pharmaceutical composition, comprising: a compound according to claim 1; a pharmaceutically acceptable carrier; and an additional therapeutic agent selected from the group consisting of enzalutamide, galeterone, ARN-509 (4-(7-(6-cyano-5-(trifluoromethyl)pylidin-3-yl)-8-oxo-6-thioxo-5,7-diazaspiro[3,4]octan-5-yl)-2-fluoro-N-methyl-benzamide), abiraterone, bicalutamide, nilutamide, flutamide, cyproterone acetate, docetaxel, bevacizumab, OSU-HDAC42 ((S)-(+)-N-Hydroxy-4-(3-methyl-2-phenyl-butyrylamino)benzamide, monoclonal antibody against the vascular integrin αvβ3, sunitumib, ZD-4054 (zibotentan), cabazitaxel (XRP-6258), MDX-010 (ipilimumab), OGX 427 (apatorsen), OGX 011 (custirsen), finasteride, dutasteride, turosteride, bextosteride, izonsteride, PCE 28260 ((1S,3aS,3bS,5aR,9aR,9bS,11aS)-9a,11a-dimethyl-7-oxo-N-(1,1,1-trifluoro-2-phenylpropan-2-yl)-1,2,3,3a,3b,4,5,5a,6,9b,10,11-dodecahydroindeno[5,4-f]-quinoline-1-carboxamide), SKF105,111 (17β-(Di-isopropyl-aminocarbonyl)androsta-3,5-diene-3-carboxylic acid), radium 233, and related compounds thereof.

10. The pharmaceutical composition of claim 9, wherein the additional therapeutic agent is for treating prostate cancer, breast cancer, ovarian cancer, endometrial cancer, salivary gland carcinoma, hair loss, acne, hirsutism, ovarian cysts, polycystic ovary disease, precocious puberty, spinal and bulbar muscular atrophy, or age-related macular degeneration.

11. A method for modulating androgen receptor activity, comprising: administering a compound according to claim 1 to a patient in need thereof.

12. A method for treating a condition or disease that is responsive to modulation of androgen receptor activity, comprising: administering a compound according to claim 1 to a patient in need thereof, wherein said condition or disease is selected from the group consisting of: prostate cancer, breast cancer, ovarian cancer, endometrial cancer, salivary gland carcinoma, hair loss, acne, hirsutism, ovarian cysts, polycystic ovary disease, precocious puberty, spinal and bulbar muscular atrophy, and age-related macular degeneration.

13. The method of claim 12, wherein the condition or disease is prostate cancer.

14. The method of claim 12, wherein the condition or disease is castration resistant prostate cancer.

15. The method of claim 12, wherein the condition or disease is androgen-dependent prostate cancer.

16. A pharmaceutical composition, comprising: a compound having the following structure:

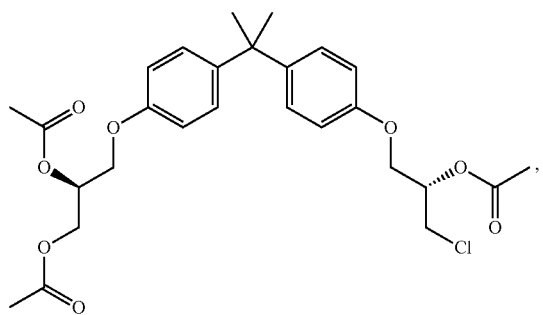

or a pharmaceutically acceptable salt thereof; and a pharmaceutically acceptable carrier.

17. The pharmaceutical composition according to claim 16, further comprising: an additional therapeutic agent selected from the group consisting of enzalutamide, galeterone, ARN-509 (4-(7-(6-cyano-5-(trifluoromethyl)pylidin-3-yl)-8-oxo-6-thioxo-5,7-diazaspiro[3,4]octan-5-yl)-2-fluoro-N-methylbenzamide), abiraterone, bicalutamide, nilutamide, flutamide, cyproterone acetate, docetaxel, bevacizumab, OSU-HDAC42 ((S)-(+)-N-Hydroxy-4-(3-methyl-2-phenyl-butyrylamino)benzamide, monoclonal antibody against the vascular integrin αvβ3, sunitumib, ZD-4054 (zibotentan), cabazitaxel (XRP-6258), MDX-010 (ipilimumab), OGX 427 (apatorsen), OGX 011 (custirsen), finasteride, dutasteride, turosteride, bextosteride, izonsteride, PCE 28260 ((1S,3aS,3bS,5aR,9aR,9bS,11aS)-9a,11a-dimethyl-7-oxo-N-(1,1,1-trifluoro-2-phenylpropan-2-yl)-1,2,3,3a,3b,4,5,5a,6,9b,10,11-dodecahydroindeno[5,4-f]-quinoline-1-carboxamide), SKF105,111 (17β-(Di-isopropyl-aminocarbonyl)androsta-3,5-diene-3-carboxylic acid), radium 233, and related compounds thereof.

18. The pharmaceutical composition of claim 17, wherein the additional therapeutic agent is for treating prostate cancer, breast cancer, ovarian cancer, endometrial cancer, salivary gland carcinoma, hair loss, acne, hirsutism, ovarian cysts, polycystic ovary disease, precocious puberty, spinal and bulbar muscular atrophy, or age-related macular degeneration.

19. A method for modulating androgen receptor activity, comprising: administering a pharmaceutical composition according to claim 16 to a patient in need thereof.

20. A method for treating a condition or disease that is responsive to modulation of androgen receptor activity, comprising: administering a pharmaceutical composition according to claim 16 to a patient in need thereof,
wherein said condition or disease is selected from the group consisting of: prostate cancer, breast cancer, ovarian cancer, endometrial cancer, salivary gland carcinoma, hair loss, acne, hirsutism, ovarian cysts, polycystic ovary disease, precocious puberty, spinal and bulbar muscular atrophy, and age-related macular degeneration.

21. The method of claim 20, wherein the condition or disease is prostate cancer.

22. The method of claim 20, wherein the condition or disease is castration resistant prostate cancer.

23. The method of claim 20, wherein the condition or disease is androgen-dependent prostate cancer.

24. A method for treating a condition or disease selected from the group consisting of: prostate cancer, breast cancer, ovarian cancer, endometrial cancer, salivary gland carcinoma, hair loss, acne, hirsutism, ovarian cysts, polycystic ovary, disease, precocious puberty, spinal and bulbar muscular atrophy, and age-related macular degeneration, comprising:
a) administering to a patient in need thereof a compound having the following structure:

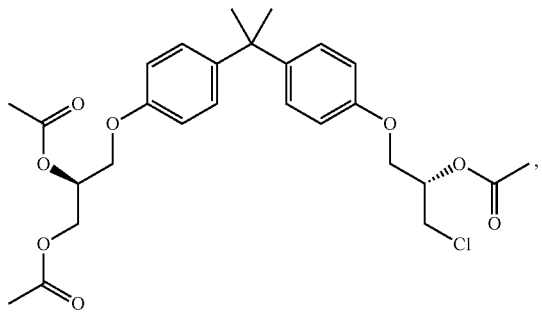

or a pharmaceutically acceptable salt of said compound.

25. The method of claim 24, wherein the condition or disease is prostate cancer.

26. The method of claim 24, wherein the condition or disease is castration resistant prostate cancer or androgen-dependent prostate cancer.

27. The compound of claim 1 selected from one or more of:

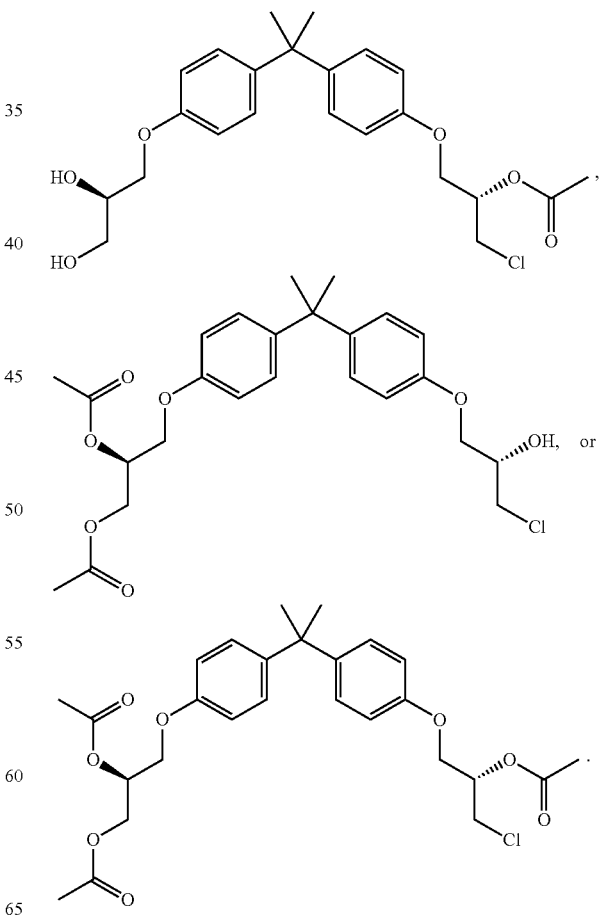

28. The compound of claim 1, wherein the compound has the following structure:
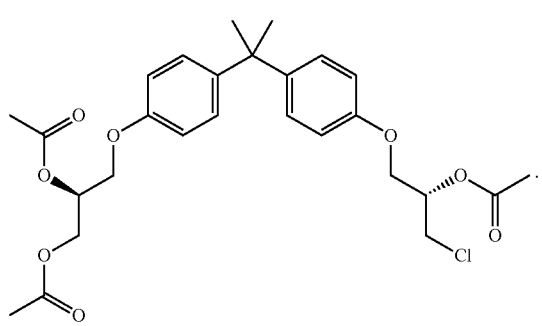 [SMILES: CC(=O)OC[C@H](COc1ccc(C(C)(C)c2ccc(OC[C@@H](CCl)OC(C)=O)cc2)cc1)OC(C)=O]
-continued
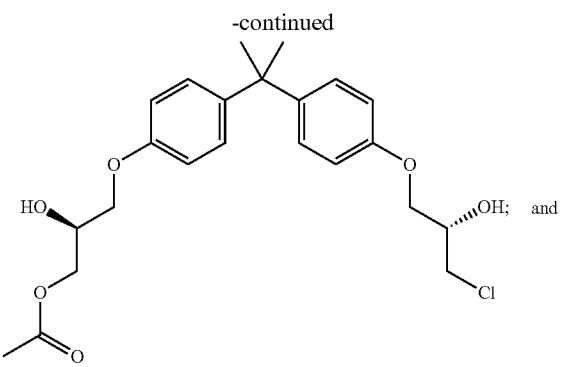
29. A compound selected from one of the following:
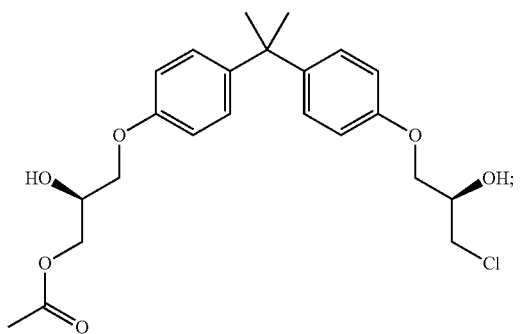
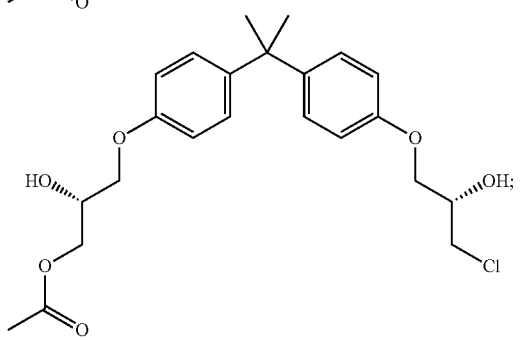
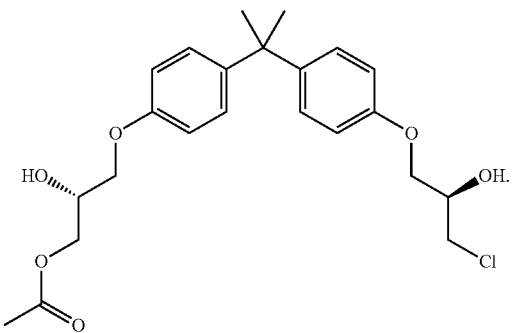
* * * * *